(12) United States Patent
Rogers et al.

(10) Patent No.: US 12,042,120 B2
(45) Date of Patent: Jul. 23, 2024

(54) METHODS AND APPARATUS TO SHAPE FLEXIBLE ENTRY GUIDES FOR MINIMALLY INVASIVE SURGERY

(71) Applicant: Intuitive Surgical Operations, Inc., Sunnyvale, CA (US)

(72) Inventors: Theodore W. Rogers, Alameda, CA (US); David Q. Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 93 days.

(21) Appl. No.: 17/190,936

(22) Filed: Mar. 3, 2021

(65) Prior Publication Data

US 2021/0228063 A1 Jul. 29, 2021

Related U.S. Application Data

(60) Continuation of application No. 15/660,673, filed on Jul. 26, 2017, now Pat. No. 10,959,607, which is a
(Continued)

(51) Int. Cl.
*A61B 1/005* (2006.01)
*A61B 1/00* (2006.01)
(Continued)

(52) U.S. Cl.
CPC ...... *A61B 1/00042* (2022.02); *A61B 1/00087* (2013.01); *A61B 1/00128* (2013.01);
(Continued)

(58) Field of Classification Search
CPC ..... A61B 1/00154; A61B 1/0016; A61B 1/31; A61B 1/00087; A61B 1/00128;
(Continued)

(56) References Cited

U.S. PATENT DOCUMENTS 3,096,962 A 7/1963 Meijs
3,546,961 A 12/1970 Marton
(Continued)

FOREIGN PATENT DOCUMENTS

CN 1155833 A 7/1997
CN 1486667 A 4/2004
(Continued)

OTHER PUBLICATIONS

Extended European Search Report for Application No. EP21201271, dated May 30, 2022, 9 pages.
(Continued)

*Primary Examiner* — Ryan N Henderson
(74) *Attorney, Agent, or Firm* — Haynes & Boone, LLP

(57) ABSTRACT

An apparatus for performing surgical procedures is disclosed including a flexible entry guide tube and a first steering device. The guide tube has one or more lumens extending along its length from a proximal end to substantially at or near a distal end. At least one of the one or more lumens is an instrument lumen with open ends to receive a flexible shaft of a surgical tool. The first steering device is insertable into the instrument lumen to shape the guide tube as it is inserted through an opening in a body and along a path towards a surgical site. The apparatus may further include a flexible locking device to couple to the flexible entry guide tube and selectively rigidize the guide tube to hold its shape. The guide tube may be steered by remote control with one or more actuators.

14 Claims, 34 Drawing Sheets

Related U.S. Application Data division of application No. 12/165,633, filed on Jun. 30, 2008, now Pat. No. 9,962,066, which is a continuation-in-part of application No. 11/762,165, filed on Jun. 13, 2007, now Pat. No. 9,060,678, and a continuation-in-part of application No. 11/491,384, filed on Jul. 20, 2006, now Pat. No. 7,930,065.

(60) Provisional application No. 60/813,030, filed on Jun. 13, 2006, provisional application No. 60/813,207, filed on Jun. 13, 2006, provisional application No. 60/813,029, filed on Jun. 13, 2006, provisional application No. 60/813,125, filed on Jun. 13, 2006, provisional application No. 60/813,075, filed on Jun. 13, 2006, provisional application No. 60/813,173, filed on Jun. 13, 2006, provisional application No. 60/813,198, filed on Jun. 13, 2006, provisional application No. 60/755,157, filed on Dec. 30, 2005.

(51) Int. Cl.
| | |
|---|---|
| *A61B 1/008* | (2006.01) |
| *A61B 1/01* | (2006.01) |
| *A61B 1/018* | (2006.01) |
| *A61B 34/00* | (2016.01) |
| *A61B 34/30* | (2016.01) |
| *A61B 34/37* | (2016.01) |
| *A61B 17/00* | (2006.01) |
| *A61B 17/29* | (2006.01) |
| *A61B 17/34* | (2006.01) |
| *A61B 34/20* | (2016.01) |

(52) U.S. Cl.
CPC ...... *A61B 1/00133* (2013.01); *A61B 1/00135* (2013.01); *A61B 1/005* (2013.01); *A61B 1/0051* (2013.01); *A61B 1/0052* (2013.01); *A61B 1/0057* (2013.01); *A61B 1/0058* (2013.01); *A61B 1/008* (2013.01); *A61B 1/009* (2022.02); *A61B 1/01* (2013.01); *A61B 34/30* (2016.02); *A61B 34/37* (2016.02); *A61B 34/71* (2016.02); *A61B 34/72* (2016.02); *A61B 1/00193* (2013.01); *A61B 1/0055* (2013.01); *A61B 1/018* (2013.01); *A61B 2017/003* (2013.01); *A61B 2017/00323* (2013.01); *A61B 2017/00327* (2013.01); *A61B 17/29* (2013.01); *A61B 2017/3445* (2013.01); *A61B 2017/3447* (2013.01); *A61B 2017/347* (2013.01); *A61B 2034/2061* (2016.02); *A61B 2034/301* (2016.02); *A61B 2034/306* (2016.02)

(58) Field of Classification Search
CPC . A61B 1/00133; A61B 1/00135; A61B 1/018; A61B 1/00193; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 17/29; A61B 2017/3445; A61B 2017/3447; A61B 2017/347; A61B 2017/003; A61B 2017/00323; A61B 2017/00327; A61B 34/30; A61B 34/32; A61B 34/35; A61B 34/37; A61B 34/70; A61B 34/71; A61B 34/72; A61B 2034/2061; A61B 2034/301; A61B 2034/306
See application file for complete search history.

(56) References Cited

U.S. PATENT DOCUMENTS

| | | | |
|---|---|---|---|
| 4,437,114 A | | 3/1984 | LaRussa |
| 4,601,283 A | * | 7/1986 | Chikama ................. A61B 1/31 600/151 |
| 4,673,988 A | | 6/1987 | Jansson et al. |
| 4,721,097 A | * | 1/1988 | D'Amelio .......... A61B 1/00142 600/128 |
| 4,742,817 A | * | 5/1988 | Kawashima ......... A61B 1/0052 600/128 |
| 4,792,715 A | | 12/1988 | Barsky et al. |
| 4,799,474 A | * | 1/1989 | Ueda ............... A61M 25/09033 604/291 |
| 4,809,191 A | | 2/1989 | Domeier et al. |
| 4,949,927 A | | 8/1990 | Madocks et al. |
| 5,114,403 A | | 5/1992 | Clarke et al. |
| 5,174,276 A | | 12/1992 | Crockard |
| 5,251,611 A | * | 10/1993 | Zehel ................... A61B 1/0055 600/114 |
| 5,297,536 A | | 3/1994 | Wilk |
| 5,307,437 A | | 4/1994 | Facq et al. |
| 5,345,937 A | * | 9/1994 | Middleman ....... A61M 25/0147 604/95.01 |
| 5,397,323 A | | 3/1995 | Taylor et al. |
| 5,417,210 A | | 5/1995 | Funda et al. |
| 5,429,604 A | | 7/1995 | Hammersmark et al. |
| 5,487,757 A | | 1/1996 | Truckai et al. |
| 5,554,098 A | * | 9/1996 | Yabe ..................... A61B 1/018 600/122 |
| 5,577,992 A | * | 11/1996 | Chiba .................. A61B 1/0058 600/116 |
| 5,617,515 A | | 4/1997 | Maclaren et al. |
| 5,624,380 A | | 4/1997 | Takayama et al. |
| 5,752,112 A | | 5/1998 | Paddock et al. |
| 5,755,713 A | | 5/1998 | Bilof et al. |
| 5,759,151 A | * | 6/1998 | Sturges ............... A61B 1/0051 600/146 |
| 5,785,689 A | * | 7/1998 | de Toledo .......... A61B 17/3478 604/165.01 |
| 5,792,135 A | | 8/1998 | Madhani et al. |
| 5,797,900 A | | 8/1998 | Madhani et al. |
| 5,810,880 A | | 9/1998 | Jensen et al. |
| 5,817,084 A | | 10/1998 | Jensen et al. |
| 5,855,569 A | * | 1/1999 | Komi ..................... A61B 10/04 604/103 |
| 5,855,583 A | | 1/1999 | Wang et al. |
| 5,868,760 A | | 2/1999 | McGuckin, Jr. |
| 5,876,325 A | | 3/1999 | Mizuno et al. |
| 5,892,860 A | | 4/1999 | Maron et al. |
| 5,899,425 A | | 5/1999 | Corey, Jr. et al. |
| 5,982,791 A | | 11/1999 | Sorin et al. |
| 5,999,662 A | | 12/1999 | Burt et al. |
| 6,030,130 A | | 2/2000 | Paddock et al. |
| 6,063,095 A | | 5/2000 | Wang et al. |
| 6,066,090 A | | 5/2000 | Yoon |
| 6,120,433 A | | 9/2000 | Mizuno et al. |
| 6,132,368 A | | 10/2000 | Cooper |
| 6,171,277 B1 | | 1/2001 | Ponzi |
| 6,179,776 B1 | * | 1/2001 | Adams ............... A61B 1/00078 600/146 |
| 6,191,414 B1 | | 2/2001 | Ogle et al. |
| 6,246,200 B1 | | 6/2001 | Blumenkranz et al. |
| 6,275,628 B1 | | 8/2001 | Jones et al. |
| 6,331,181 B1 | | 12/2001 | Tierney et al. |
| 6,332,089 B1 | | 12/2001 | Acker et al. |
| 6,347,892 B1 | | 2/2002 | Paddock et al. |
| 6,352,503 B1 | | 3/2002 | Matsui et al. |
| 6,366,722 B1 | | 4/2002 | Murphy et al. |
| 6,371,952 B1 | | 4/2002 | Madhani et al. |
| 6,389,187 B1 | | 5/2002 | Greenaway et al. |
| 6,396,574 B1 | | 5/2002 | Lee et al. |
| 6,436,107 B1 | | 8/2002 | Wang et al. |
| 6,441,577 B2 | | 8/2002 | Blumenkranz et al. |
| 6,451,027 B1 | | 9/2002 | Cooper et al. |
| 6,454,702 B1 | * | 9/2002 | Smith ................... A61B 17/29 600/130 |

(56) References Cited

U.S. PATENT DOCUMENTS

| | | |
|---|---|---|
| 6,470,205 B2 | 10/2002 | Bosselmann et al. |
| 6,471,710 B1 | 10/2002 | Bucholtz |
| 6,478,028 B1 | 11/2002 | Paolitto et al. |
| 6,487,352 B1 | 11/2002 | Sobiski et al. |
| 6,537,205 B1* | 3/2003 | Smith ............... A61B 1/015 600/130 |
| 6,554,793 B1 | 4/2003 | Pauker et al. |
| 6,569,084 B1 | 5/2003 | Mizuno et al. |
| 6,571,639 B1 | 6/2003 | May et al. |
| 6,572,629 B2 | 6/2003 | Kalloo et al. |
| 6,574,355 B2 | 6/2003 | Green |
| 6,575,644 B2 | 6/2003 | Paddock et al. |
| 6,578,967 B1 | 6/2003 | Paddock et al. |
| 6,645,196 B1 | 11/2003 | Nixon et al. |
| 6,648,816 B2 | 11/2003 | Irion et al. |
| 6,671,055 B1 | 12/2003 | Wavering et al. |
| 6,671,581 B2 | 12/2003 | Niemeyer et al. |
| 6,728,599 B2 | 4/2004 | Wang et al. |
| 6,743,239 B1 | 6/2004 | Kuehn et al. |
| 6,758,843 B2 | 7/2004 | Jensen et al. |
| 6,783,491 B2 | 8/2004 | Saadat et al. |
| 6,790,173 B2* | 9/2004 | Saadat ............... A61B 1/00135 600/129 |
| 6,800,056 B2* | 10/2004 | Tartaglia ............... A61B 1/0053 600/114 |
| 6,817,974 B2 | 11/2004 | Cooper et al. |
| 6,837,847 B2 | 1/2005 | Ewers et al. |
| 6,839,612 B2 | 1/2005 | Sanchez et al. |
| 6,840,900 B2* | 1/2005 | Smith ............... A61B 1/018 600/130 |
| 6,866,671 B2 | 3/2005 | Tierney et al. |
| 6,881,186 B2* | 4/2005 | Smith ............... A61B 1/015 600/104 |
| 6,902,560 B1 | 6/2005 | Morley et al. |
| 6,936,042 B2 | 8/2005 | Wallace et al. |
| 6,942,613 B2 | 9/2005 | Ewers et al. |
| 6,960,162 B2 | 11/2005 | Saadat et al. |
| 6,960,163 B2 | 11/2005 | Ewers et al. |
| 6,974,411 B2* | 12/2005 | Belson ............... A61B 1/00154 600/114 |
| 6,984,203 B2* | 1/2006 | Tartaglia ............... A61B 1/0014 600/114 |
| 6,991,602 B2 | 1/2006 | Nakazawa et al. |
| 6,994,703 B2 | 2/2006 | Wang et al. |
| 6,997,870 B2 | 2/2006 | Couvillon, Jr. |
| 6,999,852 B2 | 2/2006 | Green |
| 7,033,315 B2* | 4/2006 | Smith ............... A61B 1/018 600/153 |
| 7,041,052 B2 | 5/2006 | Saadat et al. |
| 7,042,573 B2 | 5/2006 | Froggatt |
| 7,052,489 B2* | 5/2006 | Griego ............... A61B 17/29 606/1 |
| 7,090,637 B2 | 8/2006 | Danitz et al. |
| 7,090,683 B2 | 8/2006 | Brock et al. |
| 7,128,708 B2 | 10/2006 | Saadat et al. |
| 7,158,860 B2 | 1/2007 | Wang et al. |
| 7,194,118 B1 | 3/2007 | Harris et al. |
| 7,222,000 B2 | 5/2007 | Wang et al. |
| 7,252,660 B2 | 8/2007 | Kunz |
| 7,320,700 B2 | 1/2008 | Cooper et al. |
| 7,371,028 B2 | 5/2008 | Gordon et al. |
| 7,386,365 B2 | 6/2008 | Nixon |
| 7,594,912 B2 | 9/2009 | Cooper et al. |
| 7,725,214 B2 | 5/2010 | Diolaiti |
| 7,854,109 B2* | 12/2010 | Zubiate ............... B25J 9/06 604/524 |
| 7,918,783 B2* | 4/2011 | Maseda ............... A61B 1/00108 600/125 |
| 7,918,785 B2* | 4/2011 | Okada ............... A61B 10/04 600/128 |
| 7,930,065 B2 | 4/2011 | Larkin et al. |
| 7,951,072 B2* | 5/2011 | Adams ............... A61B 1/00073 600/114 |
| 8,075,498 B2 | 12/2011 | Leo et al. |
| 8,281,670 B2 | 10/2012 | Larkin et al. |
| 8,419,717 B2 | 4/2013 | Diolaiti et al. |
| 8,663,096 B2* | 3/2014 | Viola ............... A61B 1/0055 600/141 |
| 8,758,228 B2* | 6/2014 | Kura ............... A61B 1/00082 600/114 |
| 8,784,435 B2 | 7/2014 | Cooper et al. |
| 8,864,752 B2 | 10/2014 | Diolaiti et al. |
| 9,039,685 B2 | 5/2015 | Larkin et al. |
| 9,060,678 B2 | 6/2015 | Larkin et al. |
| 9,060,793 B2 | 6/2015 | Larkin et al. |
| 9,066,739 B2 | 6/2015 | Larkin et al. |
| 9,084,624 B2 | 7/2015 | Larkin et al. |
| 9,101,380 B2 | 8/2015 | Larkin et al. |
| 9,125,679 B2 | 9/2015 | Larkin et al. |
| 9,241,769 B2 | 1/2016 | Larkin et al. |
| 9,283,049 B2 | 3/2016 | Diolaiti et al. |
| 9,526,583 B2 | 12/2016 | Larkin et al. |
| 9,757,149 B2 | 9/2017 | Cooper et al. |
| 9,883,914 B2 | 2/2018 | Larkin et al. |
| 9,962,066 B2 | 5/2018 | Rogers et al. |
| 9,980,630 B2 | 5/2018 | Larkin et al. |
| 10,398,520 B2 | 9/2019 | Larkin et al. |
| 10,448,812 B2 | 10/2019 | Yoon et al. |
| 10,456,166 B2 | 10/2019 | Cooper et al. |
| 10,588,711 B2 | 3/2020 | DiCarlo et al. |
| 10,791,908 B2 | 10/2020 | Au |
| 10,799,308 B2 | 10/2020 | Wang et al. |
| 10,856,770 B2 | 12/2020 | Prisco et al. |
| 10,888,248 B2 | 1/2021 | Zhao et al. |
| 10,912,523 B2 | 2/2021 | Chopra et al. |
| 10,932,877 B2 | 3/2021 | Devengenzo et al. |
| 10,959,607 B2 | 3/2021 | Rogers et al. |
| 11,013,567 B2 | 5/2021 | Wu et al. |
| 11,135,023 B2 | 10/2021 | Larkin et al. |
| 11,166,646 B2 | 11/2021 | Allenby et al. |
| 11,202,680 B2 | 12/2021 | Donhowe et al. |
| 11,219,490 B2 | 1/2022 | Barbagli et al. |
| 11,266,387 B2 | 3/2022 | Walters et al. |
| 11,278,354 B2 | 3/2022 | Duindam et al. |
| 11,278,364 B2 | 3/2022 | Cooper et al. |
| 11,298,505 B2 | 4/2022 | Bailey et al. |
| 11,445,988 B2 | 9/2022 | Chopra |
| 11,464,411 B2 | 10/2022 | Barbagli et al. |
| 11,478,138 B2 | 10/2022 | Hazelton et al. |
| 11,659,978 B2 | 5/2023 | Larkin et al. |
| 11,666,204 B2 | 6/2023 | Larkin et al. |
| 2001/0049509 A1* | 12/2001 | Sekine ............... A61B 1/018 600/104 |
| 2001/0055462 A1 | 12/2001 | Seibel |
| 2002/0007110 A1 | 1/2002 | Irion |
| 2002/0055795 A1 | 5/2002 | Niemeyer et al. |
| 2002/0058929 A1 | 5/2002 | Green |
| 2002/0087169 A1 | 7/2002 | Brock et al. |
| 2002/0099293 A1 | 7/2002 | Fontenot et al. |
| 2002/0120252 A1 | 8/2002 | Brock et al. |
| 2002/0143319 A1 | 10/2002 | Brock |
| 2002/0173786 A1 | 11/2002 | Kortenbach et al. |
| 2003/0050649 A1 | 3/2003 | Brock et al. |
| 2003/0114732 A1* | 6/2003 | Webler ............... A61B 1/00096 600/121 |
| 2003/0167061 A1 | 9/2003 | Schlegel et al. |
| 2003/0171650 A1* | 9/2003 | Tartaglia ............... A61B 1/31 600/114 |
| 2003/0228039 A1 | 12/2003 | Green |
| 2003/0233026 A1* | 12/2003 | Saadat ............... A61B 1/0055 600/114 |
| 2003/0233056 A1* | 12/2003 | Saadat ............... A61B 1/00078 600/585 |
| 2003/0236505 A1 | 12/2003 | Bonadio et al. |
| 2004/0054355 A1 | 3/2004 | Gerbi et al. |
| 2004/0083808 A1 | 5/2004 | Rambow et al. |
| 2004/0092794 A1* | 5/2004 | Chin ............... A61B 1/0684 600/179 |
| 2004/0138525 A1* | 7/2004 | Saadat ............... A61B 1/0055 600/104 |
| 2004/0138529 A1* | 7/2004 | Wiltshire ............... A61B 1/0055 600/144 |

(56) References Cited

U.S. PATENT DOCUMENTS

| | | |
|---|---|---|
| 2004/0153191 A1 | 8/2004 | Grimm et al. |
| 2004/0186350 A1* | 9/2004 | Brenneman ............ A61M 25/09 |
| | | 600/146 |
| 2004/0193146 A1 | 9/2004 | Lee et al. |
| 2004/0202400 A1 | 10/2004 | Kochergin et al. |
| 2004/0249367 A1 | 12/2004 | Saadat et al. |
| 2005/0004431 A1 | 1/2005 | Kogasaka et al. |
| 2005/0043718 A1 | 2/2005 | Madhani et al. |
| 2005/0059960 A1 | 3/2005 | Simaan et al. |
| 2005/0065397 A1* | 3/2005 | Saadat ............... A61B 17/00234 |
| | | 600/104 |
| 2005/0065398 A1 | 3/2005 | Adams |
| 2005/0075536 A1 | 4/2005 | Otsuka et al. |
| 2005/0096502 A1 | 5/2005 | Khalili |
| 2005/0096694 A1 | 5/2005 | Lee |
| 2005/0102062 A1 | 5/2005 | Green |
| 2005/0107663 A1 | 5/2005 | Saadat et al. |
| 2005/0131343 A1* | 6/2005 | Abrams ............. A61M 25/0662 |
| | | 606/41 |
| 2005/0137454 A1* | 6/2005 | Saadat ................ A61B 1/00078 |
| | | 600/129 |
| 2005/0137456 A1* | 6/2005 | Saadat ................ A61B 1/00078 |
| | | 600/114 |
| 2005/0215983 A1 | 9/2005 | Brock |
| 2005/0222554 A1* | 10/2005 | Wallace ................. A61B 5/283 |
| | | 606/1 |
| 2005/0234293 A1* | 10/2005 | Yamamoto ........ A61B 1/00149 |
| | | 600/102 |
| 2005/0250990 A1* | 11/2005 | Le ............................ A61B 1/31 |
| | | 600/114 |
| 2005/0251176 A1 | 11/2005 | Swanstrom et al. |
| 2005/0251177 A1* | 11/2005 | Saadat ................ A61B 17/0401 |
| | | 606/153 |
| 2005/0272977 A1 | 12/2005 | Saadat et al. |
| 2005/0273084 A1 | 12/2005 | Hinman et al. |
| 2005/0284221 A1 | 12/2005 | Danisch et al. |
| 2006/0013523 A1 | 1/2006 | Childers et al. |
| 2006/0025652 A1* | 2/2006 | Vargas ................. A61B 1/0055 |
| | | 600/114 |
| 2006/0095022 A1 | 5/2006 | Moll et al. |
| 2006/0149130 A1* | 7/2006 | Bob ..................... A61B 1/00154 |
| | | 600/114 |
| 2006/0149418 A1 | 7/2006 | Anvari |
| 2006/0161136 A1 | 7/2006 | Anderson et al. |
| 2006/0178562 A1* | 8/2006 | Saadat ................. A61B 1/0055 |
| | | 600/142 |
| 2006/0200049 A1 | 9/2006 | Leo et al. |
| 2006/0258938 A1 | 11/2006 | Hoffman et al. |
| 2006/0287666 A1* | 12/2006 | Saadat ............... A61M 25/1011 |
| | | 606/198 |
| 2007/0021738 A1 | 1/2007 | Hasser et al. |
| 2007/0043338 A1 | 2/2007 | Moll et al. |
| 2007/0055291 A1 | 3/2007 | Birkmeyer et al. |
| 2007/0065077 A1 | 3/2007 | Childers et al. |
| 2007/0089557 A1 | 4/2007 | Solomon et al. |
| 2007/0135683 A1* | 6/2007 | Bob ..................... A61B 1/00082 |
| | | 600/114 |
| 2007/0135803 A1 | 6/2007 | Belson |
| 2007/0137371 A1 | 6/2007 | Devengenzo et al. |
| 2007/0149852 A1* | 6/2007 | Noguchi ............ A61B 1/00082 |
| | | 600/152 |
| 2007/0151391 A1 | 7/2007 | Larkin et al. |
| 2007/0156020 A1 | 7/2007 | Foley et al. |
| 2007/0197896 A1 | 8/2007 | Moll et al. |
| 2007/0225554 A1* | 9/2007 | Maseda ................... A61B 1/018 |
| | | 600/128 |
| 2007/0265503 A1 | 11/2007 | Schlesinger et al. |
| 2007/0283970 A1 | 12/2007 | Mohr et al. |
| 2007/0287884 A1 | 12/2007 | Schena |
| 2007/0287889 A1 | 12/2007 | Mohr |
| 2008/0039690 A1* | 2/2008 | Zubiate .............. A61B 1/00071 |
| | | 600/141 |
| 2008/0058861 A1 | 3/2008 | Cooper et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin et al. |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065106 A1 | 3/2008 | Larkin |
| 2008/0065107 A1 | 3/2008 | Larkin et al. |
| 2008/0065109 A1 | 3/2008 | Larkin et al. |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0091170 A1 | 4/2008 | Vargas et al. |
| 2008/0119872 A1 | 5/2008 | Brock et al. |
| 2008/0147089 A1 | 6/2008 | Loh et al. |
| 2008/0151041 A1 | 6/2008 | Shafer et al. |
| 2008/0156971 A1 | 7/2008 | Ogisu et al. |
| 2008/0171908 A1 | 7/2008 | Okada et al. |
| 2008/0188890 A1 | 8/2008 | Weitzner et al. |
| 2008/0212082 A1 | 9/2008 | Froggatt et al. |
| 2008/0249357 A1* | 10/2008 | Soetermans ........ A61B 1/00105 |
| | | 600/114 |
| 2008/0262300 A1* | 10/2008 | Ewers ................. A61B 1/00142 |
| | | 600/114 |
| 2008/0269559 A1* | 10/2008 | Miyamoto ......... A61B 1/00148 |
| | | 600/116 |
| 2008/0287963 A1* | 11/2008 | Rogers .................... A61B 1/009 |
| | | 606/130 |
| 2009/0054728 A1* | 2/2009 | Trusty ................ A61B 1/00135 |
| | | 600/114 |
| 2009/0124857 A1* | 5/2009 | Viola ................... A61B 1/0055 |
| | | 600/141 |
| 2009/0149710 A1* | 6/2009 | Stefanchik ......... A61B 1/00078 |
| | | 600/146 |
| 2009/0192524 A1 | 7/2009 | Itkowitz et al. |
| 2009/0248040 A1 | 10/2009 | Cooper et al. |
| 2009/0253961 A1* | 10/2009 | Le ...................... A61B 1/00071 |
| | | 600/121 |
| 2009/0314131 A1 | 12/2009 | Bailey |
| 2009/0322001 A1 | 12/2009 | Luke et al. |
| 2009/0326322 A1 | 12/2009 | Diolaiti |
| 2009/0326552 A1 | 12/2009 | Diolaiti |
| 2009/0326553 A1 | 12/2009 | Mustufa et al. |
| 2010/0170519 A1 | 7/2010 | Romo et al. |
| 2010/0256446 A1* | 10/2010 | Raju ..................... A61B 1/0091 |
| | | 600/114 |
| 2010/0274087 A1 | 10/2010 | Diolaiti et al. |
| 2010/0332030 A1 | 12/2010 | Larkin et al. |
| 2010/0332033 A1 | 12/2010 | Diolaiti et al. |
| 2011/0040305 A1 | 2/2011 | Gomez et al. |
| 2011/0040404 A1 | 2/2011 | Diolaiti et al. |
| 2011/0082365 A1 | 4/2011 | McGrogan et al. |
| 2011/0152613 A1* | 6/2011 | Zubiate .............. A61B 1/00016 |
| | | 600/109 |
| 2011/0152879 A1 | 6/2011 | Williams et al. |
| 2011/0184241 A1* | 7/2011 | Zubiate ..................... B25J 9/104 |
| | | 600/141 |
| 2011/0196419 A1 | 8/2011 | Cooper |
| 2011/0201883 A1 | 8/2011 | Cooper et al. |
| 2011/0202068 A1 | 8/2011 | Diolaiti et al. |
| 2011/0213202 A1* | 9/2011 | Maseda ................... A61B 1/018 |
| | | 600/104 |
| 2011/0277576 A1 | 11/2011 | Cooper |
| 2011/0277579 A1 | 11/2011 | Anderson et al. |
| 2011/0277580 A1 | 11/2011 | Cooper et al. |
| 2011/0277775 A1 | 11/2011 | Holop et al. |
| 2011/0277776 A1 | 11/2011 | McGrogan et al. |
| 2011/0282356 A1 | 11/2011 | Solomon et al. |
| 2011/0282357 A1 | 11/2011 | Rogers et al. |
| 2011/0282358 A1 | 11/2011 | Gomez et al. |
| 2011/0282359 A1 | 11/2011 | Duval |

(56) References Cited

U.S. PATENT DOCUMENTS

| | | |
|---|---|---|
| 2012/0010628 A1 | 1/2012 | Cooper et al. |
| 2013/0041214 A1* | 2/2013 | Maahs ................. A61B 1/0051 600/104 |
| 2015/0265368 A1 | 9/2015 | Chopra et al. |
| 2016/0183841 A1 | 6/2016 | Duindam et al. |
| 2017/0265952 A1 | 9/2017 | Donhowe et al. |
| 2017/0354318 A1 | 12/2017 | Rogers et al. |
| 2018/0193100 A1 | 7/2018 | Larkin et al. |
| 2019/0206004 A1 | 7/2019 | Shelton, IV et al. |
| 2019/0365202 A1 | 12/2019 | Larkin et al. |
| 2019/0374293 A1 | 12/2019 | Larkin et al. |
| 2020/0106937 A1 | 4/2020 | Cooper et al. |
| 2020/0146754 A1 | 5/2020 | Row et al. |
| 2022/0047341 A1 | 2/2022 | Larkin et al. |
| 2022/0183780 A1 | 6/2022 | Cooper et al. |
| 2023/0054233 A1 | 2/2023 | Millman et al. |
| 2023/0181264 A1 | 6/2023 | Kang et al. |
| 2023/0277175 A1 | 9/2023 | Shelton, IV et al. |
| 2023/0309793 A1 | 10/2023 | Larkin et al. |
| 2023/0320730 A1 | 10/2023 | Viola et al. |
| 2023/0338101 A1 | 10/2023 | Hasser et al. |
| 2023/0371780 A1 | 11/2023 | Butte et al. |

FOREIGN PATENT DOCUMENTS

| | | |
|---|---|---|
| EP | 0776738 A2 | 6/1997 |
| EP | 1334700 A1 | 8/2003 |
| JP | S57190549 A | 11/1982 |
| JP | H06285009 A | 10/1994 |
| JP | H07504363 A | 5/1995 |
| JP | 2000093522 A | 4/2000 |
| JP | 2000166936 A | 6/2000 |
| JP | 2001327460 A | 11/2001 |
| JP | 2002537884 A | 11/2002 |
| JP | 2003275223 A | 9/2003 |
| KR | 19990087101 A | 12/1999 |
| WO | WO-9313916 A1 | 7/1993 |
| WO | WO-9729690 A1 | 8/1997 |
| WO | WO-0051486 A1 | 9/2000 |
| WO | WO-0217810 A2 | 3/2002 |
| WO | WO-2004052171 A2 | 6/2004 |
| WO | WO-2005087128 A1 | 9/2005 |
| WO | WO-2005115226 A2 | 12/2005 |
| WO | WO-2006039092 A2 | 4/2006 |
| WO | WO-2007120329 A2 | 10/2007 |
| WO | WO-2007146987 A2 | 12/2007 |
| WO | WO-2008028149 A2 | 3/2008 |
| WO | WO-2009002701 A2 | 12/2008 |

OTHER PUBLICATIONS

Bergamasco M., et al., "Advanced Interfaces for Teleoperated Biomedical Robots," IEEE Engineering in Medicine & Biology Society 11th Annual Int'l Conf., pp. 912-913, vol. 3, IEEE, Jun. 1989.

Chen M.D., et al., "A Robotics System for Stereotactic Neurosurgery and Its Clinical Application," IEEE, May 1998, pp. 995-1000.

Mack M.J., et al., "Minimally Invasive and Robotic Surgery," Opportunities for Medical Research, Feb. 2001, vol. 285 (5), pp. 568-572.

Haga Y. and Esashi M., "Biomedical Microsystems for Minimally Invasive Diagnosis and Treatment," Proceedings of the IEEE, Jan. 2004, vol. 92, No. 1, pp. 98-114.

Shapo B.M., et al., "Displacement and Strain Imaging of Coronary Arteries With Intraluminal Ultrasound," IEEE, Mar. 1996, pp. 234-246.

Tanimoto M., et al., "Micro Force Sensor for Intravascular Neurosurgery," IEEE, Apr. 1997, pp. 1561-1566.

Tanimoto M., et al., "Micro Force Sensor for Intravascular Neurosurgery and in Vivo Experiment," IEEE, Jan. 1998, pp. 504-509.

Payne C.J., et.al., "A Hand-Held Flexible Mechatronic Device for Arthroscopy," IEEE/RSJ International Conference on Intelligent Robots and Systems (IROS), 2015, pp. 817-823.

Russo et.al., "A Novel Robotic Platform for Laser-Assisted Transurethral Surgery of the Prostate," IEEE Transactions on Biomedical Engineering, Feb. 2015, vol. 62 (2), pp. 489-500.

Sareh S., et.al., "A 7.5mm Steiner Chain Fibre-Optic System for Multi-Segment Flex Sensing," IEEE/RSJ International Conference on Intelligent Robots and Systems (IROS), 2015, 2336-2341.

Searle T.C., et.al., "An Optical Curvature Sensor for Flexible Manipulators," IEEE International Conference on Robotics and Automation, May 2013, pp. 4415-4420.

Abbott, Daniel J. et al., "Design of an Endoluminal NOTES Robotic System," Conference on Intelligent Robots and Systems, 2007, pp. 410-416.

Anisfield, Nancy; "Ascension Technology Puts Spotlight on DC Field Magnetic Motion Tracking," HP Chronicle, Aug. 2000, vol. 17, No. 9, 3 Pages.

Ascari, Luca et al., "A New Active Microendoscope for Exploring the Sub-Arachnoid Space in the Spinal Cord," Proc. IEEE International Conference on Robotics and Automation, 2003, pp. 2657-2662, vol. 2, IEEE.

Barnes Industries, Inc., "How a Ball Screw Works," 4 pages, Copyright 2007; Internet: http://www.barnesballscrew.com/ball.htm.

Berthold III, John W., "Historical Review of Microbend Fiber-Optic Sensors," Journal of Lightwave Technology, vol. 13, No. 7, Jul. 1995, pp. 1193-1199.

Blue Road Research, "Overview of Fiber Optic Sensors," 40 pages, first posted Dec. 8, 2004. Internet www.bluerr.com/papers/Overview_of_FOS2.pdf.

Cao, Caroline G.L., "Designing Spatial Orientation in Endoscopic Environments," Proceedings of the Human Factors and Ergonomics Society 45th Annual Meeting, 2001, pp. 1259-1263.

Cao, Caroline G.L., "Disorientation in Minimal Access Surgery: A Case Study," Proceedings of the IEA 2000/HFES 2000 Congress, pp. 4-169-4-172.

Childers, Brooks A., et al., "Use of 3000 Bragg grating strain sensors distributed on four eight-meter optical fibers during static load tests of a composite structure," SPIE 8th International Symposium on Smart Structures and Materials, Mar. 4-8, 2001, Newport Beach, California, 10 Pages.

Choi, Dong-Geol et al., "Design of a Spring Backbone Micro Endoscope," Conference on Intelligent Robots and Systems, 2007, pp. 1815-1821.

Co-pending U.S. Appl. No. 11/762,185, inventor Thomas; G. Cooper, filed Jun. 13, 2007.

Cowie, Barbara M., et al., "Distributive Tactile Sensing Using Fibre Bragg Grating Sensors for Biomedical Applications," 1st IEEE / RAS-EMBS International Conference on Biomedical Robotics and Biomechatronics (BioRob 2006), Feb. 2006, pp. 312-317.

Danisch, Lee et al., "Spatially continuous six degree of freedom position and orientation sensor," Sensor Review, 1999, vol. 19, Issue 2, pp. 106-112.

Dario, Paolo et al., "A Miniature Device for Medical Intracavitary Intervention," Micro Electro Mechanical Systems '91 Proc IEEE 'An Investigation of Micro Structures, Sensors, Actuators, Machines and Robots', 1991, pp. 171-175, IEEE.

Duncan, Roger, "Sensing Shape: Fiber-Bragg-grating sensor arrays monitor shape at a high resolution," 2005, pp. 18-21, SPIE.

Extended European Search Report for Application No. EP20070798487, dated Jan. 30, 2015, 8 pages.

Gagarina, T. et al., "Modeling and experimental analysis of a new bellow type actuators for active catheter end-effector," Proc. 10th IEEE International Workshop on Robot and Human Interactive Communication, 2001, pp. 612-617, IEEE.

Gander, M.J. et al., "Bend measurement using Bragg gratings in multicore fibre," Electronics Letter, Jan. 20, 2000, vol. 36, No. 2, 2 Pages.

Hill, Kenneth O., "Fiber Bragg grating technology fundamentals and overview," IEEE Journal of Lightwave Technology, vol. 15, Issue 8, Aug. 1997, pp. 1263-1276.

Ikuta, Koji et al., "Development of remote microsurgery robot and new surgical procedure for deep and narrow space," Proc. IEEE International Conference on Robotics & Automation, 2003, pp. 1103-1108, vol. 1, IEEE.

(56) References Cited

OTHER PUBLICATIONS

Ikuta, Koji et al., "Shape memory alloy servo actuator system with electric resistance feedback and application for active endoscope," Proc. IEEE International Conference on Robotics and Automation, 1988, pp. 427-430, vol. 1, IEEE.
International Search Report for application No. PCT/US07/71085, dated Sep. 17, 2008, 2 pages.
Jin, Long et al., "Two-dimensional bend sensing with a cantilever-mounted FBG [Fiber Bragg Grating]," Meas. Sci. Technol., 2006, pp. 168-172, vol. 17, Institute of Physics Publishing.
Kreger, Stephen et al., "Optical Frequency Domain Reflectometry for High Density Multiplexing of Multi-Axis Fiber Bragg Gratings," 16th International Conference on Optical Fiber Sensors (OFS-16), Oct. 2003, Nara, Japan, pp. 526-529.
Lertpiriyasuwat, Vatchara et al., "Extended Kalman Filtering Applied to a Two-Axis Robotic Arm with Flexible Links," International Journal of Robotics Research, 2000, vol. 19., No. 3, pp. 254-270.
Lunwei Z., et al., "FBG Sensor Devices for Spatial Shape Detection of Intelligent Colonoscope," IEEE International Conference on Robotics and Automation, Apr. 2004, New Orleans, Louisiana, pp. 835-840.
Martinez, A. et al., "Vector Bending Sensors Based on Fibre Bragg Gratings Inscribed by Infrared Femtosecond Laser," Electronics Letters, 2005, pp. 472-474, vol. 41—Issue 8.
Measurand, "ShapeTape Overview," Measurand ShapeTape Advantage, pp. 1-3, first posted Nov. 3, 2004. Internet www.measurand.com/products/ShapeTape_overview.html.
Meltz, Gerald, "Overview of Fiber Grating-Based Sensors," Proceedings of SPIE Distributed Multiplexed Fiber Optic Sensors VI, Nov. 27, 1996, Eds. Kersey et al., vol. 2838, pp. 2-22.
Office Action dated Jun. 17, 2014 for Japanese Application No. 20130179563 filed Aug. 30, 2013, 7 pages.
PCT/US07/71085 Written Opinion, dated Sep. 17, 2008, 5 pages.
PCT/US09/46446 International Search Report and Written Opinion of the International Searching Authority, dated Dec. 14, 2009, 21 pages.
PCT/US09/46446 Partial International Search Report and Invitation to Pay Additional Fees, dated Sep. 18, 2009, 9 pages.
PCT/US2011/035113 International Search Report and Written Opinion of the International Searching Authority, dated Aug. 4, 2011, 13 pages.
Stieber, Michael E. et al., "Vision-Based Sensing and Control for Space Robotics Applications," IEEE Transactions on Instrumentation and Measurement, Aug. 1999, vol. 48, No. 4, pp. 807-812.
Sturges, Robert H. et al., "A Flexible, Tendon-Controlled Device for Endoscopy," The International Journal of Robotics Research, 1993, vol. 12(2), pp. 121-131.
Szewczyk, Jerome et al., "An active tubular polyarticulated microsystem for flexible endoscope," Lecture Notes in Control and Information Sciences, vol. 271, Experimental Robotics VII, 2000, pp. 179-188, Springer-Verlag.
U.S. Appl. No. 60/813,028, inventor Thomas Cooper; Menlo Park, Ca, filed Jun. 13, 2006.
U.S. Appl. No. 60/813,029, inventor David Q. Larkin; Menlo Park, Ca, filed Jun. 13, 2006.
U.S. Appl. No. 60/813,030, inventor David Q. Larkin; Menlo Park, Ca, filed Jun. 13, 2006.
U.S. Appl. No. 60/813,075, inventor David Q. Larkin; Menlo Park, Ca, filed Jun. 13, 2006.
U.S. Appl. No. 60/813,125, inventor David Q. Larkin; Menlo Park, Ca, filed Jun. 13, 2006.
U.S. Appl. No. 60/813,126, inventor Thomas G. Cooper; Menlo Park, Ca, filed Jun. 13, 2006.
U.S. Appl. No. 60/813,129, inventor Thomas G. Cooper; Menlo Park, Ca, filed Jun. 13, 2006.
U.S. Appl. No. 60/813,131, inventor Eugene Duval; Menlo Park, Ca, filed Jun. 13, 2006.
U.S. Appl. No. 60/813,172, inventor Thomas G. Cooper; Menlo Park, Ca, filed Jun. 13, 2006.
U.S. Appl. No. 60/813,173, inventor David Larkin; Menlo Park, Ca, filed Jun. 13, 2006.
U.S. Appl. No. 60/813,198, inventor David Q. Larkin; Menlo Park, Ca, filed Jun. 13, 2006.
U.S. Appl. No. 60/813,207, inventor Nicola Diolaiti; Palo Alto, Ca, filed Jun. 13, 2006.
U.S. Appl. No. 60/813,328, inventor Catherine Moore; Menlo Park, Ca, filed Jun. 13, 2006.
U.S. Appl. No. 61/334,978, inventor McGrogan; Anthony, filed May 14, 2010.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Wang, Yi-Ping et al., "A novel long period fiber grating sensor measuring curvature and determining bend-direction simultaneously," IEEE Sensors Journal, 2005, pp. 839-843, vol. 5—Issue: 5, IEEE.
Webster, Robert J. III et al., "Toward Active Cannulas: Miniature Snake-Like Surgical Robots," 2006, 7 pages.
Wong, Allan C. L. et al., "Multiplexed fibre Fizeau interferometer and fibre Bragg grating sensor system for simultaneous measurement of quasi-static strain and temperature using discrete wavelet transform," Measurement Science and Technology, 2006, pp. 384-392, vol. 17—Issue 2, Institute of Physics Publishing.
Dattamajumbar A.K., et al., "A Low-cost Fiber-Optic Instrument to Colorimetrically Detect Patients With Barrett's Esophagus for Early Detection of Esophageal Adenocarcinoma," IEEE Transactions on Bio-medical Engineering, Jun. 2001, vol. 48(6), pp. 695-705.
Kamiya M., et al., "Analog Data Transmission Through Plastic Optical Fiber in Robot With Compensation of Errors Caused by Optical Fiber Bending Loss," IEEE Transactions on Industrial Electronics, Oct. 2001, vol. 48(5), pp. 1034-1037.
Kamiya M., et al., "Measurement of Dimensions Using Robot Constructed Utilizing Optical Fiber Signal Transmission System Having Reference Capability," Proceedings of the IEEE International Conference on Industrial Technology, Dec. 1996, pp. 204-208.
Kassim I., et al., "Locomotion Techniques for Robotic Colonoscopy," IEEE Engineering in Medicine and Biology Magazine, Jun. 2006, vol. 25, pp. 49-56.
Larson B.T., et al., "Robotic Device for Minimally Invasive Breast Inerventions With Real-time MRI Guidance," IEEE Symposium on Bioinformatics and Bioengineering (BIBE), Mar. 2003, pp. 1-8.
Puangmali P., et al., "State-of-the-Art in Force and Tactile Sensing for Minimally Invasive Surgery," IEEE Sensors Journal, Apr. 2008, vol. 8 (4), pp. 371-381.
Seibold U., et al., Prototype of Instrument for Minimally Invasive Surgery with 6-Axis Force Sensing Capability, Proceedings of the 2005 IEEE International Conference on Robotics and Automation Barcelona, Spain, Apr. 2005, pp. 498-503.
Walt D.r., "Fiber-optic Sensors for Continuous Clinical Monitoring," Proceedings of the IEEE, Jun. 1992, vol. 80(6), pp. 903-911.

* cited by examiner

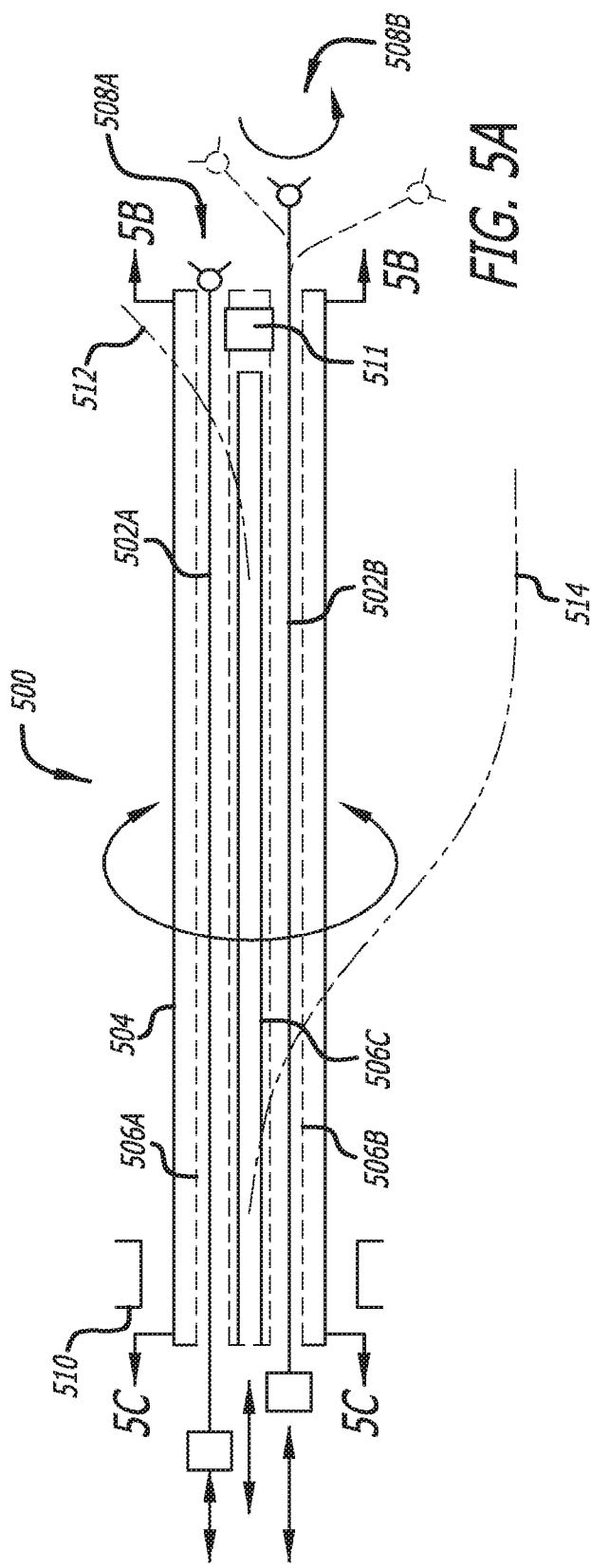
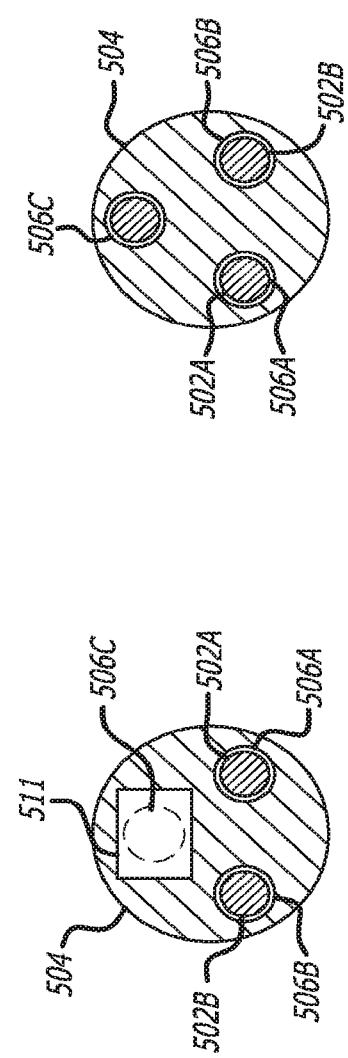

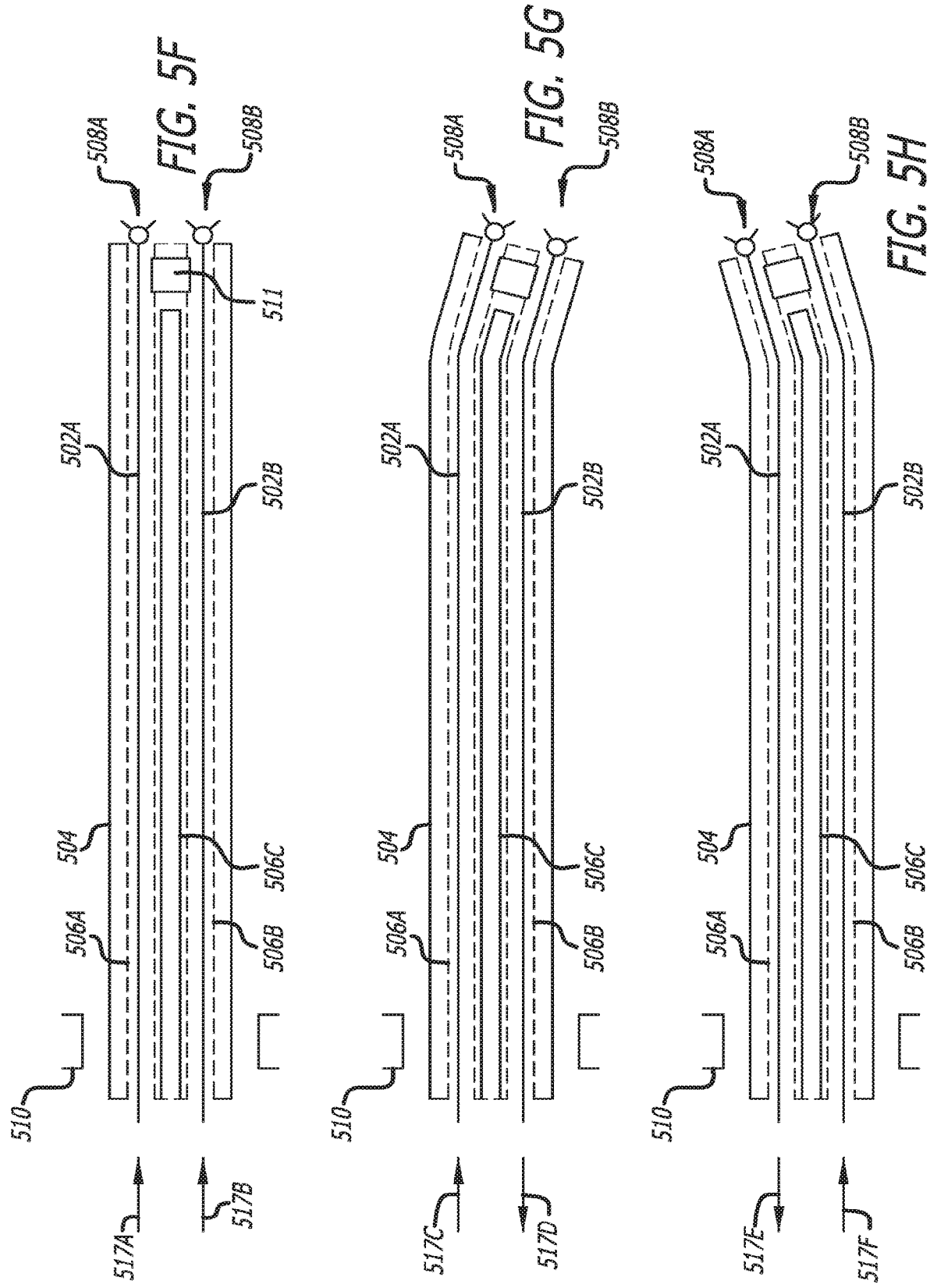

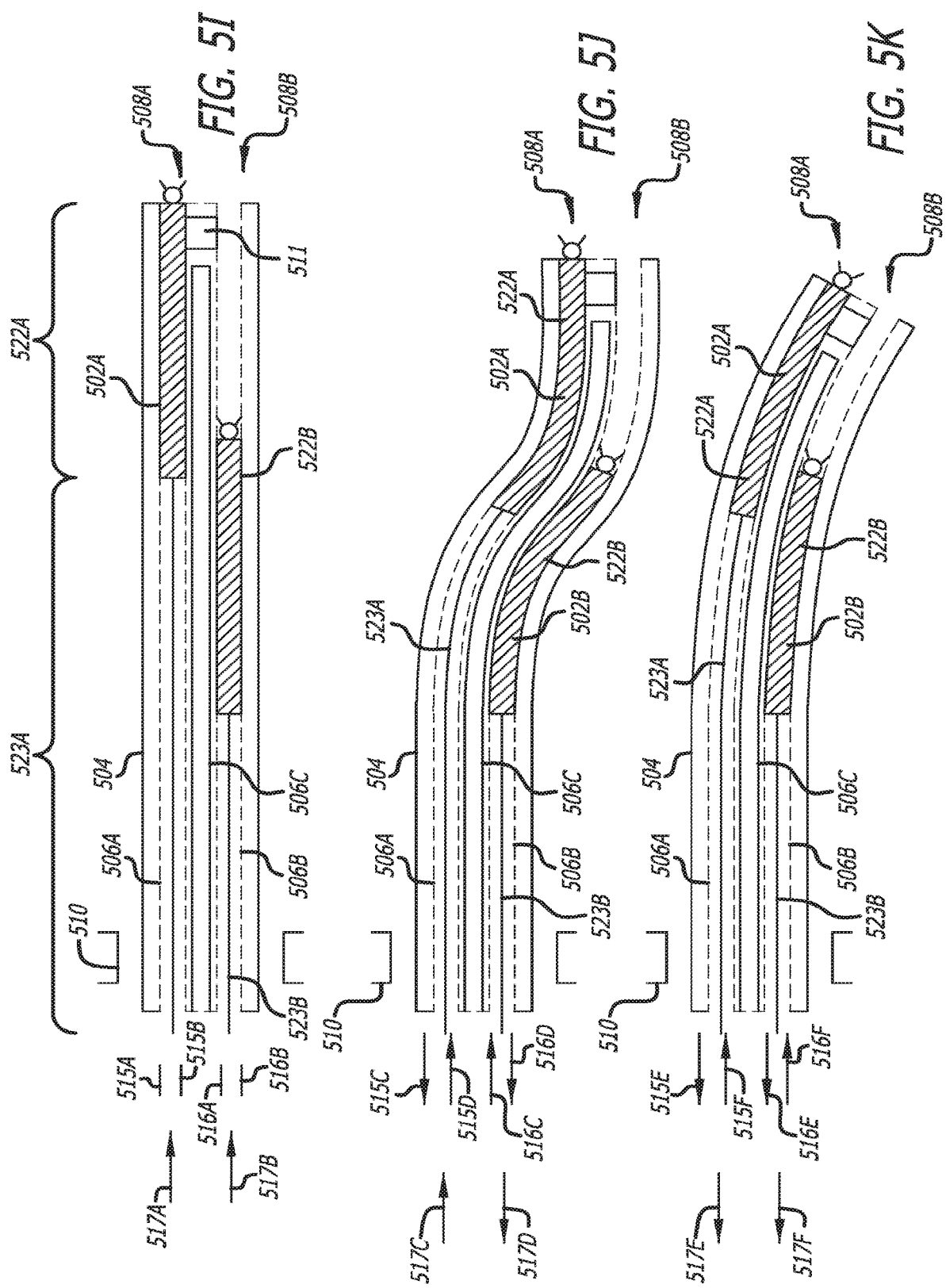

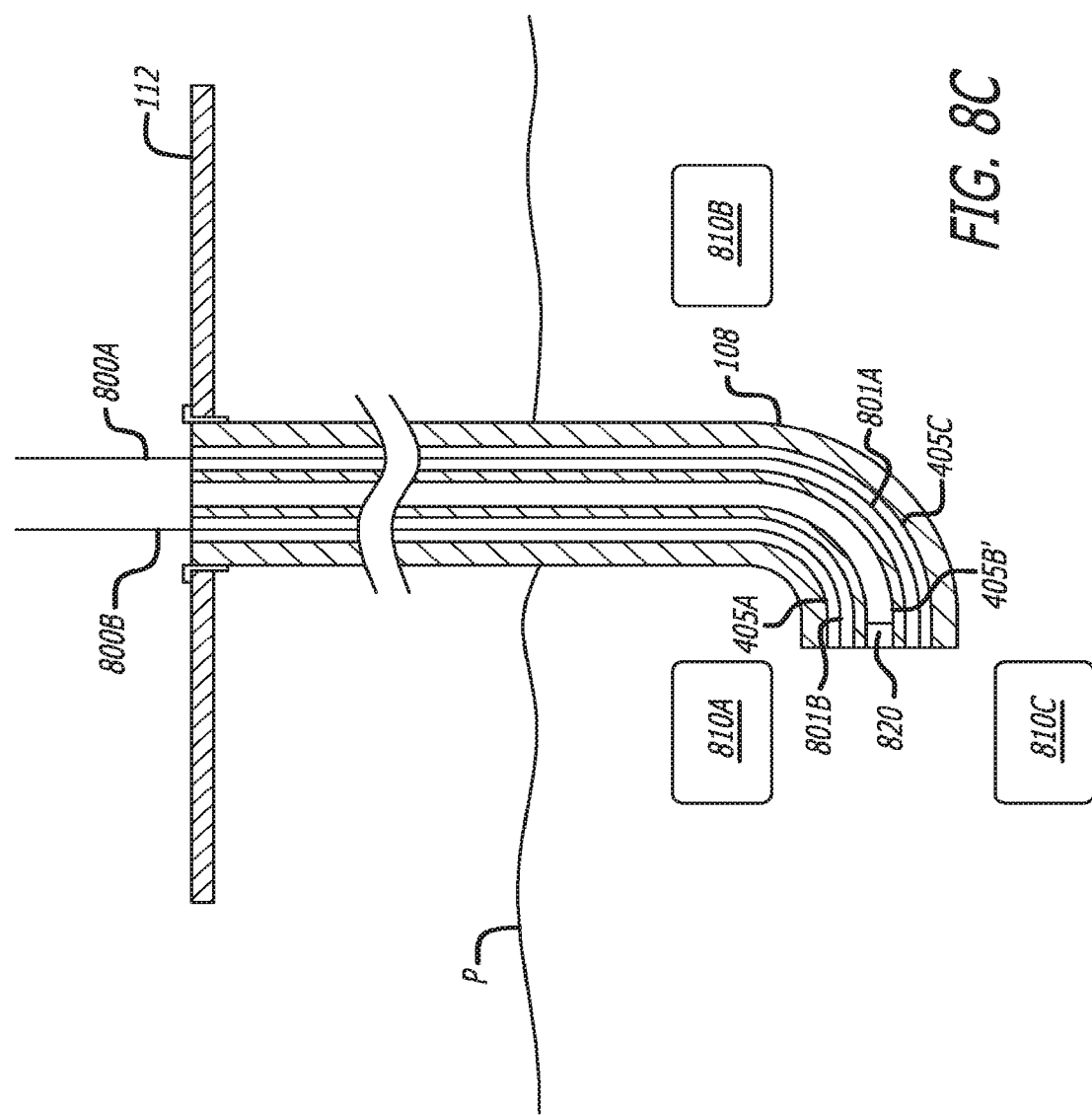

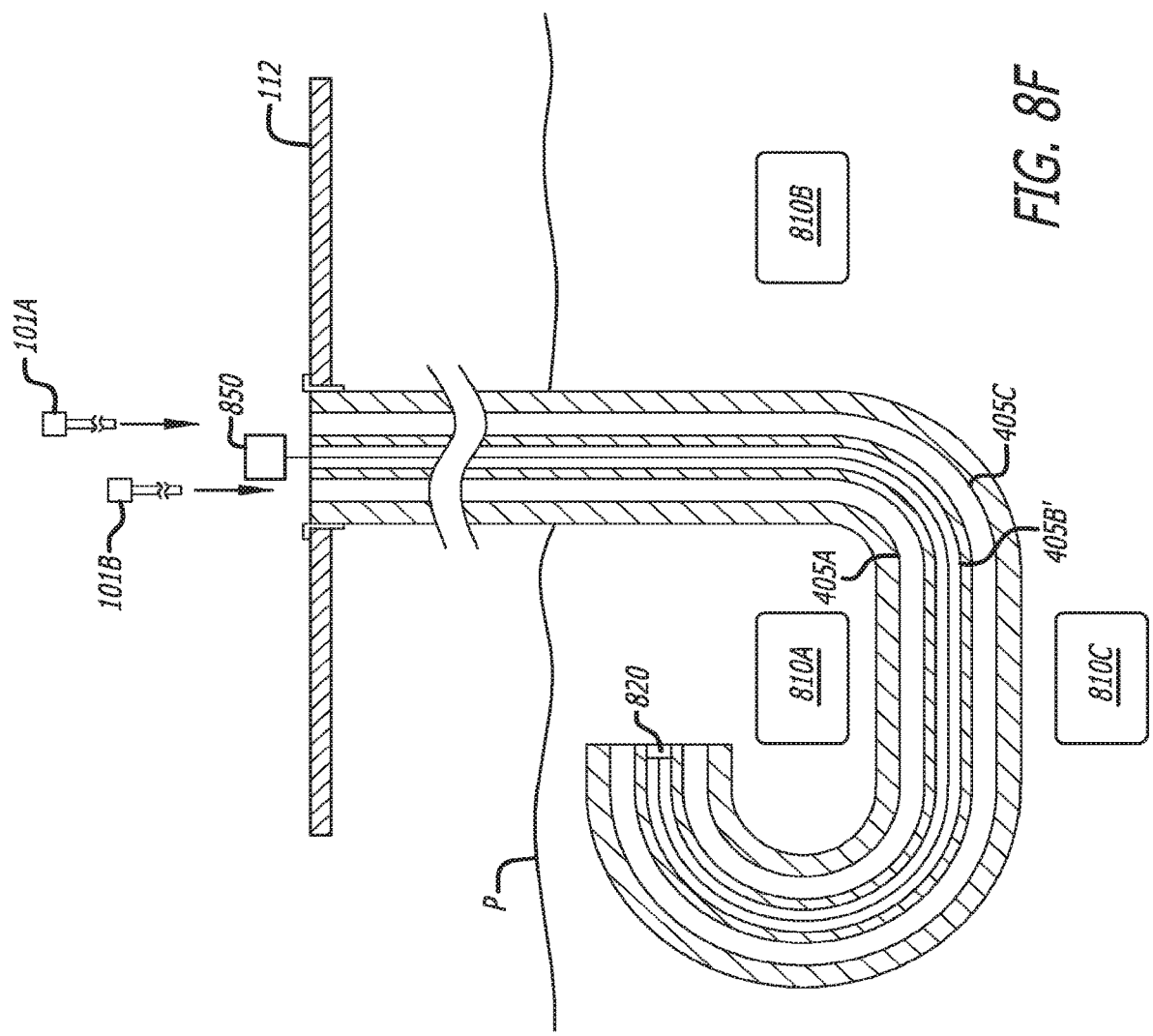

METHODS AND APPARATUS TO SHAPE FLEXIBLE ENTRY GUIDES FOR MINIMALLY INVASIVE SURGERY

CROSS REFERENCE TO RELATED APPLICATIONS

This non-provisional United States (U.S.) patent application is a continuation of U.S. Patent application Ser. No. 15/660,673, filed Jul. 26, 2017, which is a divisional application of and claims the benefit of U.S. patent application Ser. No. 12/165,633 entitled "METHODS AND APPARATUS TO SHAPE FLEXIBLE ENTRY GUIDES FOR MINIMALLY INVASIVE SURGERY," filed on Jun. 30, 2008, now U.S. Pat. No. 9,962,066, which in turn claims the benefit of and is a continuation-in-part of U.S. patent application Ser. No. 11/762,165, entitled "MINIMALLY INVASIVE SURGICAL SYSTEM," filed on Jun. 13, 2007, now U.S. Pat. No. 9,060,678, and also claims the benefit of and is a continuation-in-part of U.S. patent application Ser. No. 11/491,384, entitled "ROBOTIC SURGERY SYSTEM INCLUDING POSITION SENSORS USING FIBER BRAGG GRATINGS," filed on Jul. 20, 2006, now U.S. Pat. No. 7,930,065, all of which are incorporated herein by reference in their entirety. U.S. Patent application Ser. No. 11/762,165 further claims priority to and the benefit of U.S. Provisional Patent Application Nos. 60/813,075, 60/813,207, 60/813,198, 60/813,173, 60/813,125, and 60/813,029, all filed on Jun. 13, 2006, of which this patent application also claims the benefit, and all of which are incorporated herein by reference in their entirety. U.S. patent application Ser. No. 11/491,384 further claims the benefit of U.S. Provisional Patent Application No. filed on Dec. 30, 2005, of which this application also claims the benefit, and which is incorporated herein by reference in its entirety.

FIELD

The embodiments of the invention relate generally to guide systems for robotic tools or instruments.

BACKGROUND

Minimally invasive surgical (MIS) procedures have become more common using robotic (e.g., telerobotic) surgical systems. Even still, a number of minimally invasive surgical procedures are performed using a plurality of surgical tools which are inserted through a plurality of openings in a patient's body. If openings into a patient's body are formed by cutting, they must be closed and allowed to heal. If the openings through which the surgical procedures are performed are reduced to a single opening, the time for recovery and risks of infection for a patient may be reduced. Moreover if the size of the one or more openings into the body can be reduced, it may be easier to close after the minimally invasive surgical procedure.

Additionally, the human body has a number of natural orifices through which surgical tools may be inserted. For example, the nostrils in the nose or the throat in the mouth of a patient may be used to perform some minimally invasive surgical procedures. The use of a natural orifice for some minimally invasive surgical procedures may permit a quicker recovery with little to no visible scarring.

Moreover, some surgical procedures must traverse long distances and/or open spaces within a human body to reach the surgical site from an opening. While endoscopes are often used to access such surgical sites, they are often limited in their ability to reach sites in an open space that lie substantially away from their direction of insertion. And while many endoscopes are capable of retroflexing one hundred eighty degrees, the short length of their articulated tips generally limits their maximum radius of curvature when so bent, which thus limits their reach within the abdomen. An exemplary surgical procedure is a trans-gastric cholysystectomy. For this surgical procedure, an endoscope may be inserted via the esophagus, through the wall of the stomach, and into the peritoneum far enough to reach into the lower abdomen and then, because of the limitations of its articulation, must follow the edges of the cavity around and back up to the gall bladder. Thus, an endoscope, capable of being articulated over long portions of its length to reach a surgical site that does not lie in the direction of initial insertion, is desired.

BRIEF SUMMARY

The embodiments of the invention are summarized by the claims that follow below.

BRIEF DESCRIPTIONS OF THE DRAWINGS

FIG. 2 is a perspective view of a distal end portion of the flexible guide tube with a plurality of robotic surgical tools extending out there-from.

FIGS. 5A, 5B, and 5C are schematic drawings of an entry guide system including a pair of robotic surgical tools.

Figure 5D:
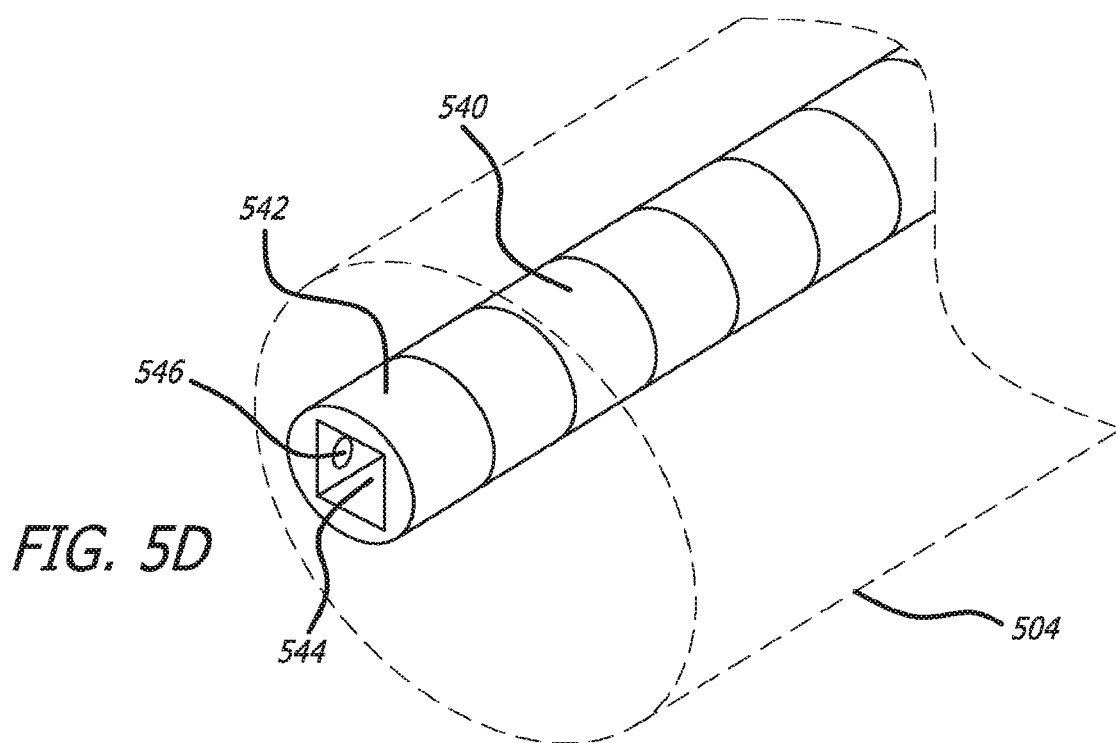
Figure 5E:
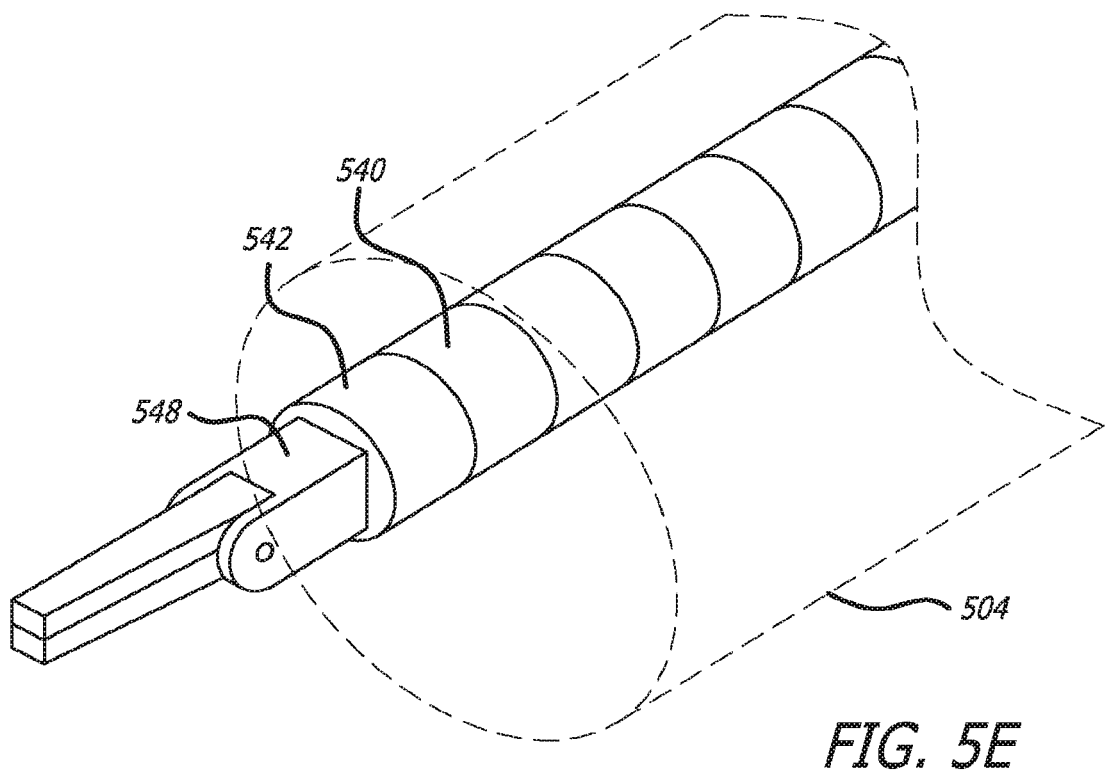

FIGS. 5D and 5E are perspective views of the distal end of the entry guide.

FIGS. 5F, 5G, 5H are schematic views to illustrate how robotic surgical tools may be used to steer the distal end of the entry guide.

FIGS. 5I, 5J, and 5K are schematic views of an entry guide system to illustrate how robotic surgical tools may be used in series within lumens to steer the distal end of the entry guide.

Figure 6A:
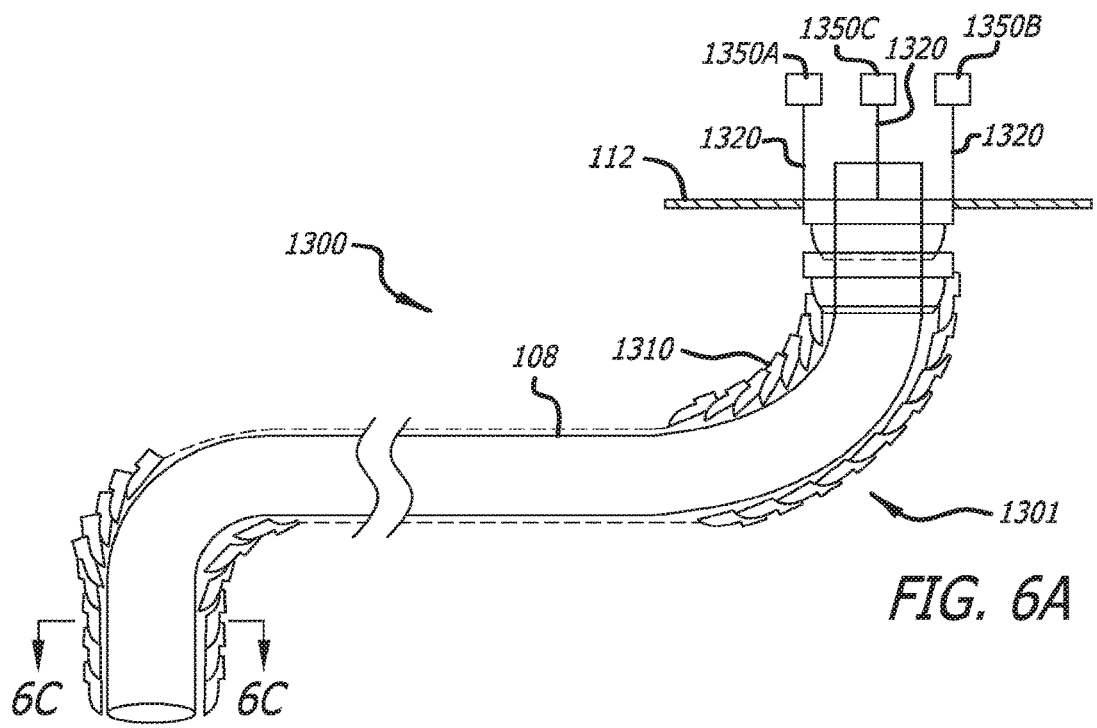
Figure 6C:
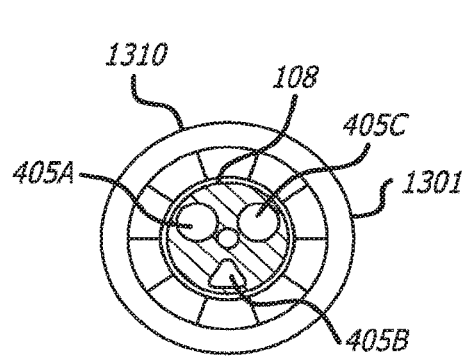
Figure 6B:
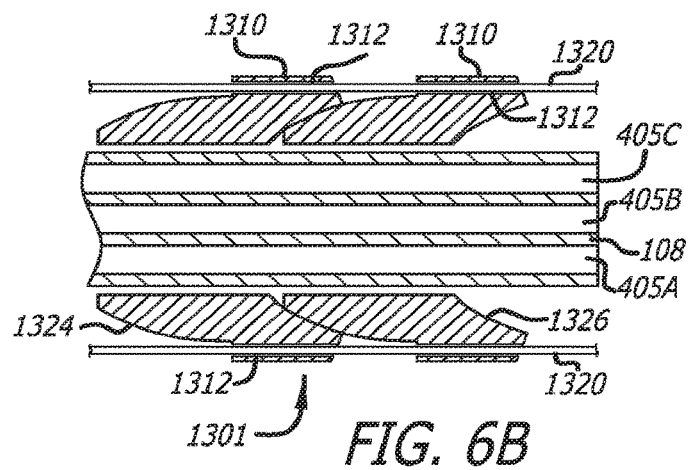

FIGS. 6A, 6B, and 6C illustrate cut-away views of a robotically controlled flexible locking sleeve.

Figure 7A:
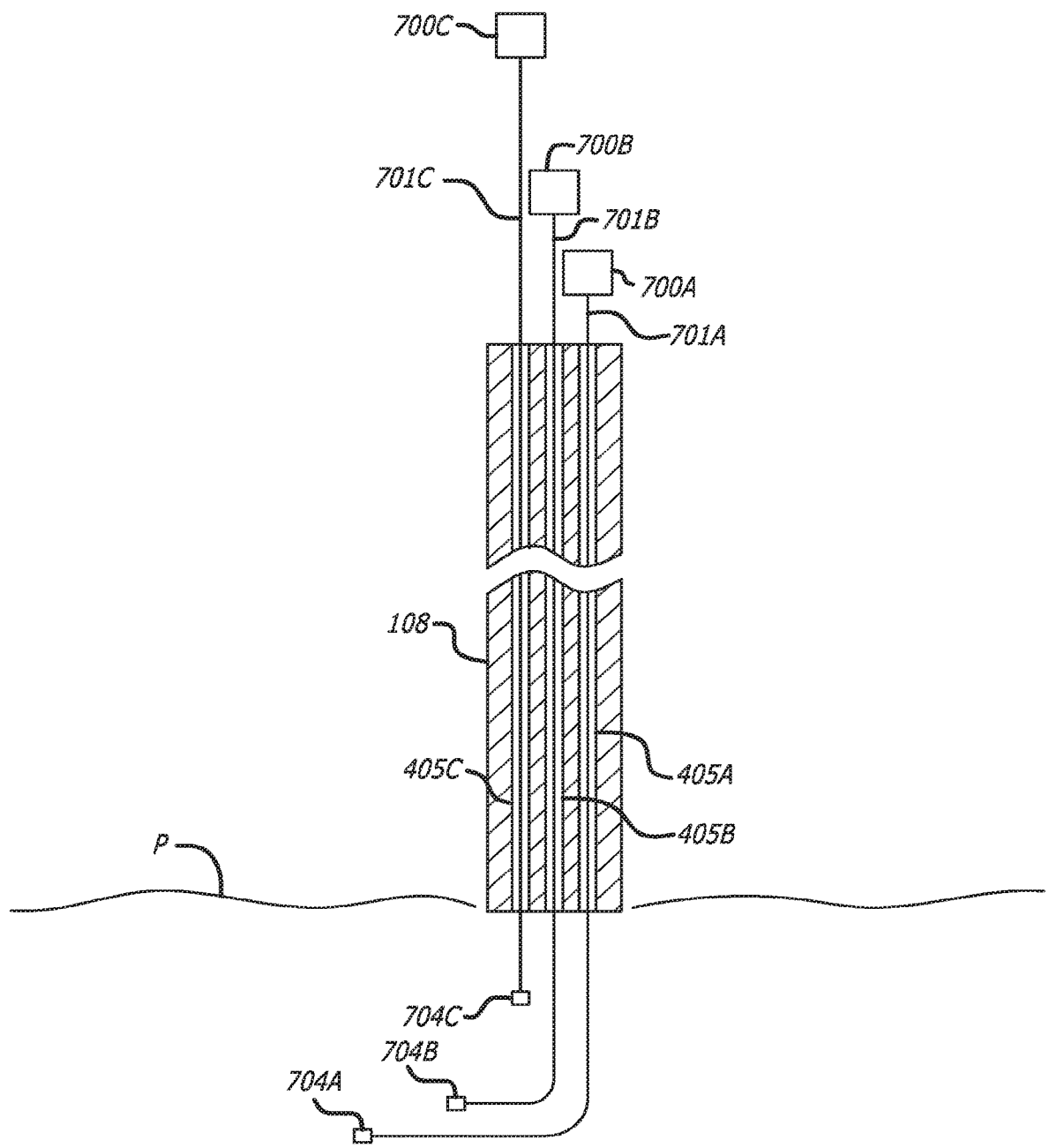
Figure 7B:
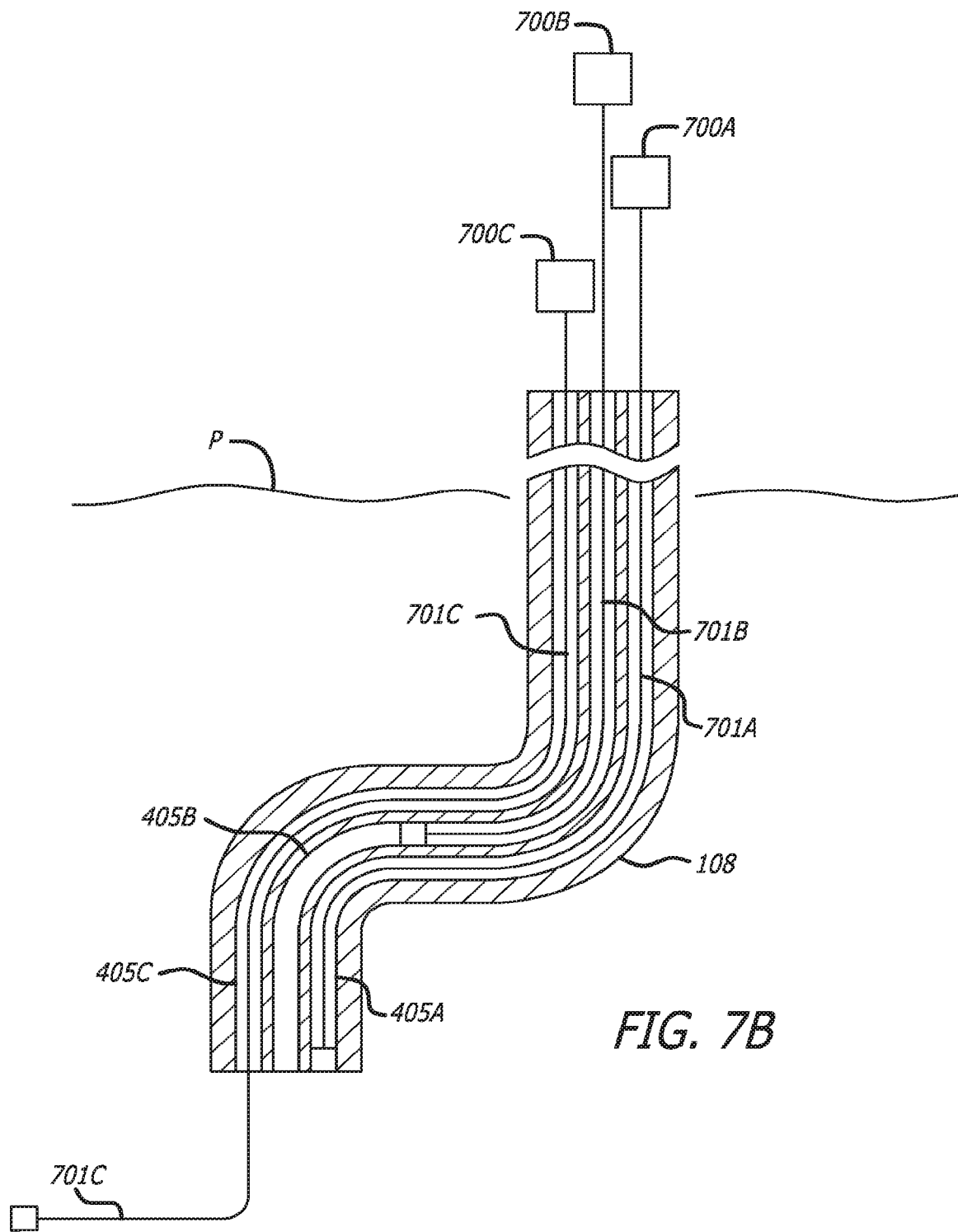
Figure 7C:
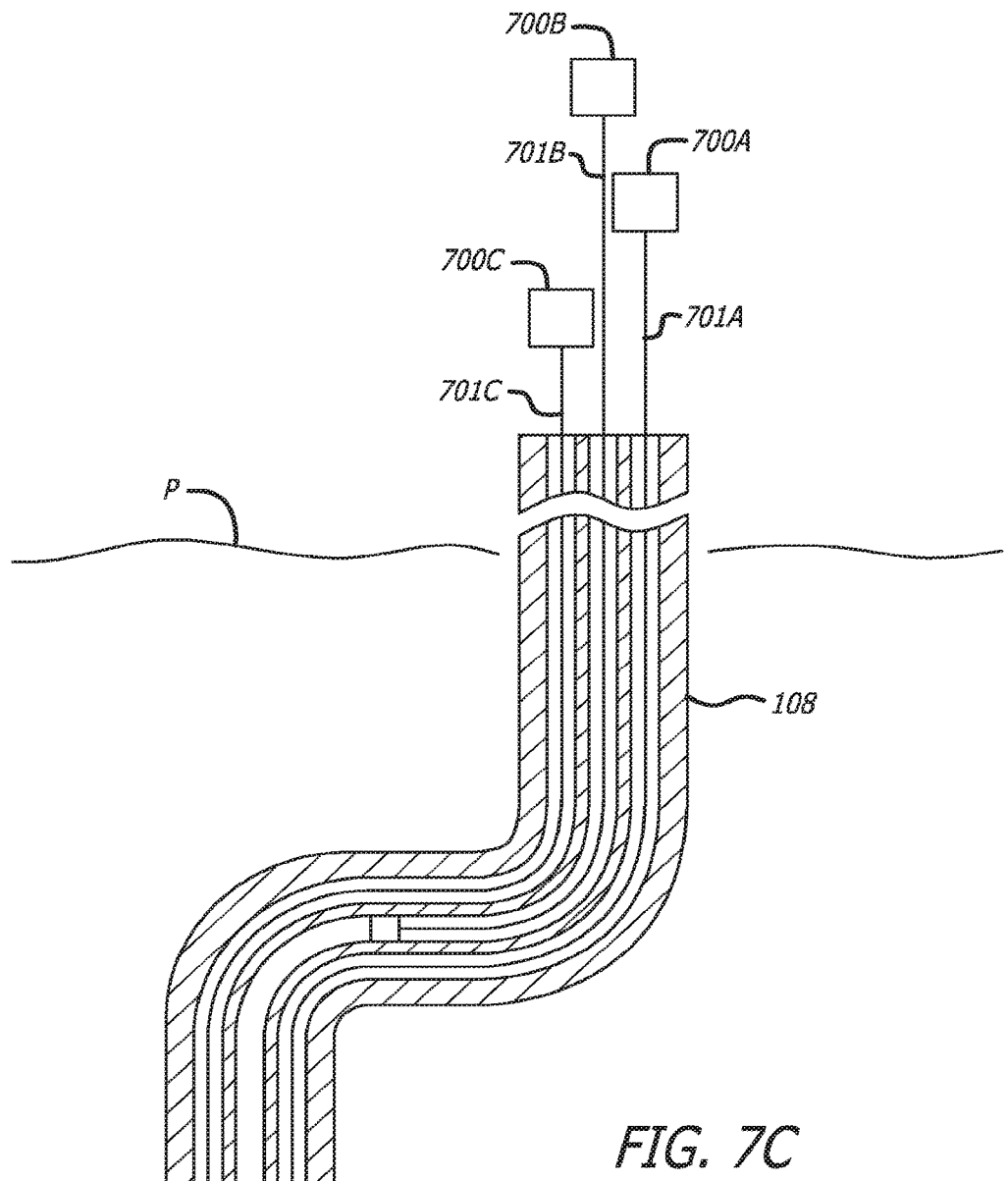

FIGS. 7A, 7B, and 7C are schematic views of an entry guide system including a plurality of steering tools that extend out of a lumen to shape and steer the entry guide to the surgical site.

FIGS. 8A, 8B, 8C, 8D, 8E, and 8F are schematic views of an entry guide system including a plurality of pre-curved rods that extend out of the lumens at the distal end to scout out and select the path of the entry guide to shape and steer the entry guide to the surgical site.

FIGS. 9A, 9B, 9C, 9D, 9E, and 9F are schematic views of an entry guide system to illustrate how robotic surgical tools may be used in series to steer the distal end of the entry guide.

Figure 10:
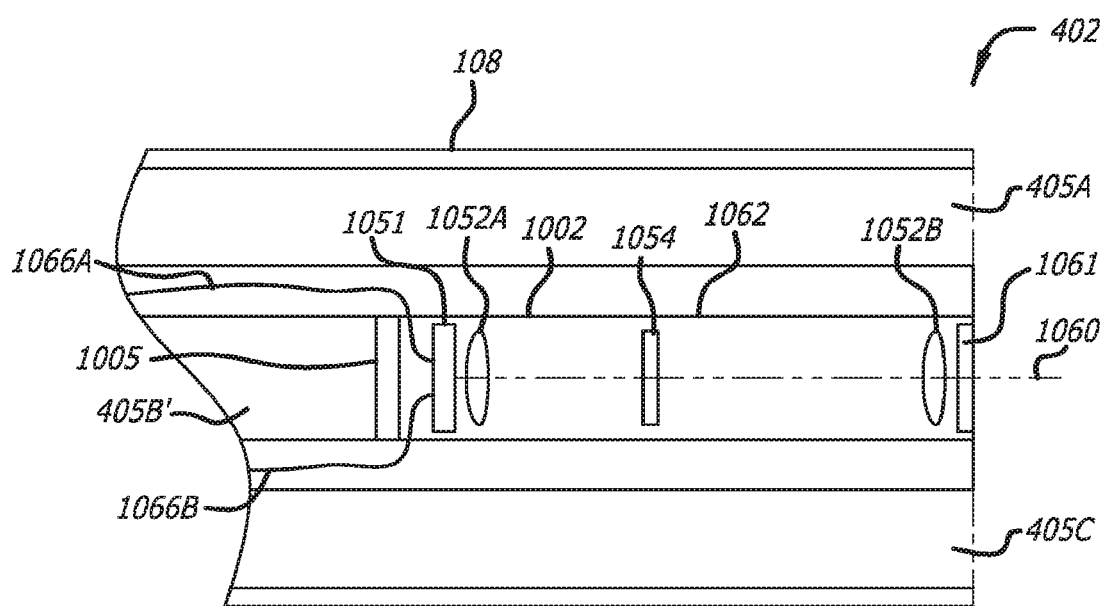

FIG. 10 is a cutaway side view of the distal end of the entry guide to illustrate an integrated camera tool aligned with a closed end of a lumen.

DETAILED DESCRIPTION

In the following detailed description of the embodiments of the invention, numerous specific details are set forth in order to provide a thorough understanding of the present invention. However, the embodiments of the invention may be practiced without these specific details. In other instances well known methods, procedures, components, and circuits have not been described in detail so as not to unnecessarily obscure aspects of the embodiments of the invention.

Introduction

Methods and apparatus for influencing the behavior (e.g. shape, stiffness, range of motion, bend radius, etc) of a flexible entry guide are disclosed. A flexible entry guide is a flexible tube-shaped device with one or more interior lumens to guide shafts of one or more endoscopic robotic surgical instruments to a surgical site and/or support such instruments and react to surgical forces once at the surgical site. A typical entry guide may have two to four lumens sized to accommodate instruments or tools which may be inserted down a lumen for any purpose. For example, an instruments or tools which may be inserted down a lumen may be endoscopic cameras, graspers, scissors, cautery tools, etc. A tube to provide suction or irrigation is a simple instrument that may be inserted down a lumen. An inflatable device to retract or displace tissue is likewise an instrument that may be inserted down a lumen.

It may be advantageous to change robotic surgical tools during a surgical procedure for several reasons. A different tool may be needed at different steps within a procedure. A tool may be withdrawn from a surgical site to remove a tissue sample. A tool may be withdrawn for cleaning. A tool may be withdrawn for replacement because of a functional failure.

Numerous control cables may be used actuate lengthy entry guides and can utilize a significant portion of the cross-sectional area of the entry guide. The control cables may be used to actuate the entry guide by providing either steering or locking functions, or both. The instrument lumens take up some cross-sectional area of the entry guide as well. If fewer control cables are used to actuate the flexible entry guide, cross sectional area may be reduced or additional and/or larger lumens may be provided within the entry guide. The force that a cable-driven surgical instrument can exert and the stiffness provided by the instrument in response to imposed external forces, are both roughly proportional to the cube of the diameter of the body of the surgical instrument. Thus, providing a larger portion of the cross section of the flexible entry guide for instrument lumens allows for a substantial increase in the performance of those instruments.

Instead of using control cables alone to actuate the entry guide, one or more devices may be inserted into the one or more lumens to influence the behavior of the entry guide. The methods and apparatus disclosed herein may enhance the performance (e.g. stiffness, range of motion, minimum achievable bend radius, etc) of the entry guide, reduce its complexity, and/or diameter by transferring some or all of its actuation means to devices that may be temporarily inserted into the lumens.

Given the competing constraints on the cross-sectional area of the entry guide, the embodiments of the invention make use of the space required by the instrument lumens to accomplish some or all of the entry guide actuation functions using fewer control cables. Instead, rigid stiffening devices may be inserted into the instrument lumens to modify the flexibility of an entry guide such that a larger workspace of surgical sites may be reached with little interaction to the surrounding tissue. Alternatively, steering devices may be inserted into the instrument lumens to steer or assist in steering all or portions of the entry guide.

Robotic Surgical System

Figure 1A:
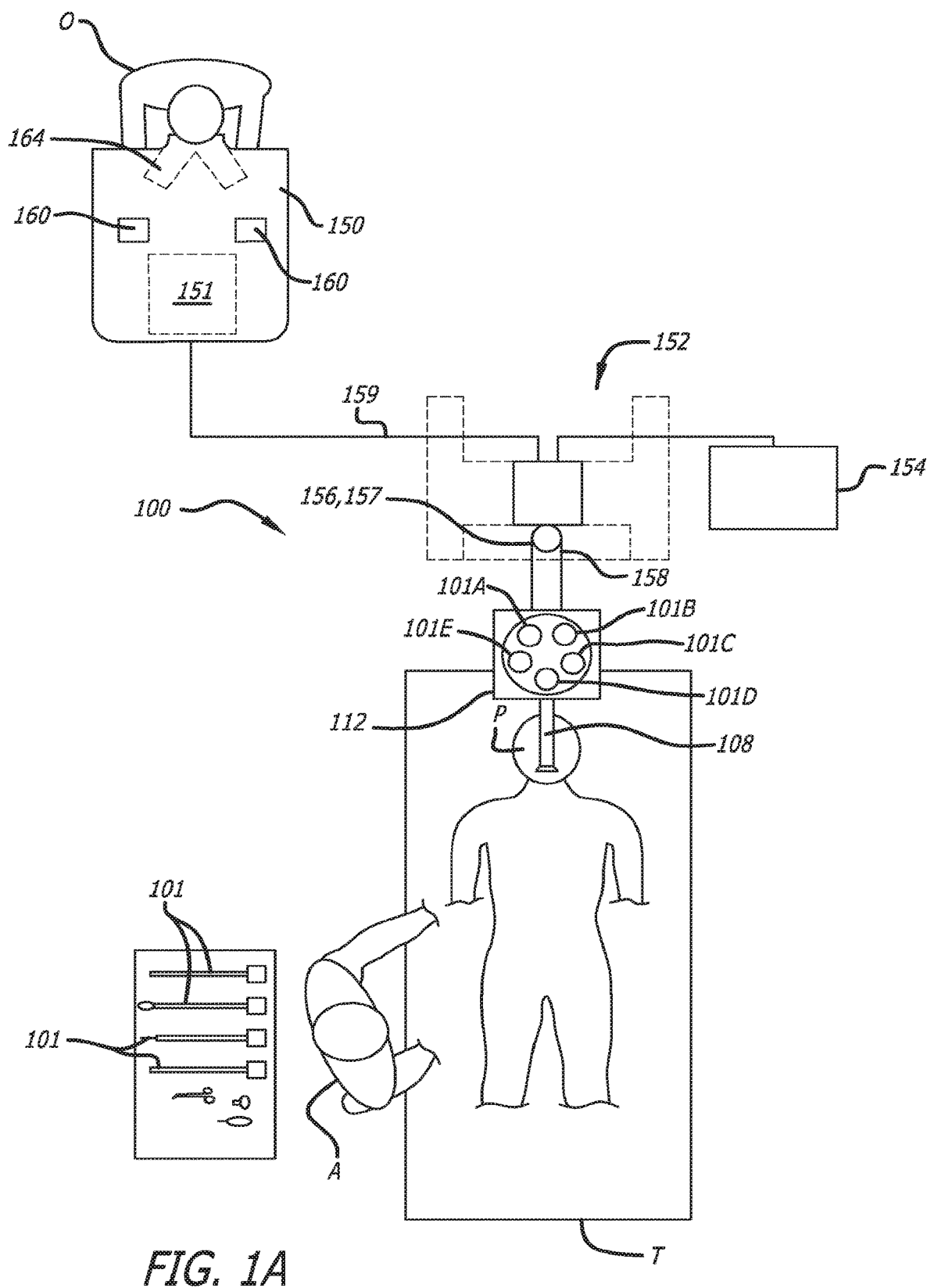
FIG. 1A is a block diagram of a robotic medical system including an entry guide system for one or more robotic surgical tools.

Referring now to FIG. 1A, a block diagram of a robotic surgery system 100 is illustrated to perform minimally invasive robotic surgical procedures using a master control console 150 and a patient side cart 152. Aspects of system 100 include telerobotic and autonomously operating features. Robotic surgery may be used to perform a wide variety of surgical procedures, including but not limited to open surgery, neurosurgical procedures (e.g., stereotaxy), endoscopic procedures (e.g., laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101E via control lines 159, effecting movement of the instruments using the robotic patient-side system 152 (also referred to as a patient-side cart). The patient side cart 152 includes a robotic arm 158 that can be manipulated by a surgeon O at the master control console 150. The robotic arm 158 is coupled to a platform 112 to support an entry guide 108 and a plurality of robotic surgical tools 101A-101E inserted into the entry guide 108. As the platform 112 is a moveable platform that moves with the robotic arm 158, it may raise and lower the entry guide 108 as it is inserted through an opening in the patient P on the table T. The robotic arm 158 and the platform 112 may also twist, turn, and angle the proximal end of the entry guide 108 as it is inserted. The platform 112 may also support actuators (See FIG. 4A) coupled to control cables to robotically steer the distal end and portions of the body of the entry guide 108 within the patient to a surgical site.

The entry guide 108 may include a camera as part of its distal end. Alternatively, a stereo or three-dimensional surgical image capture device may be inserted into an instrument lumen of the entry guide 108, such as a stereo endoscope (which may be any of a variety of structures such as a stereo laparoscope, arthroscope, hysteroscope, or the like), or, optionally, some other imaging modality (such as ultrasound, fluoroscopy, magnetic resonance imaging, or the like). For example, the robotic instrument 101B may be an image capture device and the robotic instruments 101A and 101C-101E may be used to manipulate tissue.

Robotic instruments are generally referred to herein by the reference number 101. Robotic instruments 101 may be any instrument or tool that is inserted into the entry guide 108 that can be manipulated by one or more actuators under remote control of the master control console 150. Robotic instruments include, but are not limited to, surgical tools, medical tools, biomedical tools, and diagnostic instruments (ultrasound, computer tomography (CT) scanner, magnetic resonance imager (MRI)).

Generally, the robotic patient-side system 152 may include a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The driven portion of the robotic patient-side system 152 may include, but is not limited or restricted to the robotic surgical arm 158, the entry guide 108, and the robotic instruments or tools 101.

As an exemplary embodiment, the positioning portion of the robotic patient-side system 152 that is in a fixed configuration during surgery may include, but is not limited or restricted to a set-up arm 156. The set-up arm 156 may include a plurality of links and a plurality of joints 157. The set-up arm mounts via a first set-up-joint 157 to the patient side system 152.

An assistant A may assist in pre-positioning of the robotic patient-side system 152 relative to patient P as well as swapping tools or instruments 101 for alternative tools or instruments, and the like, while viewing the internal surgical site via an external display 154. The external display 154 or another external display 154 may be positioned or located elsewhere so that images of the surgical site may be displayed to students or other interested persons during a surgery. Images with additional information may be overlaid onto the images of the surgical site by the robotic surgical system for display on the external display 154.

Figure 1B:
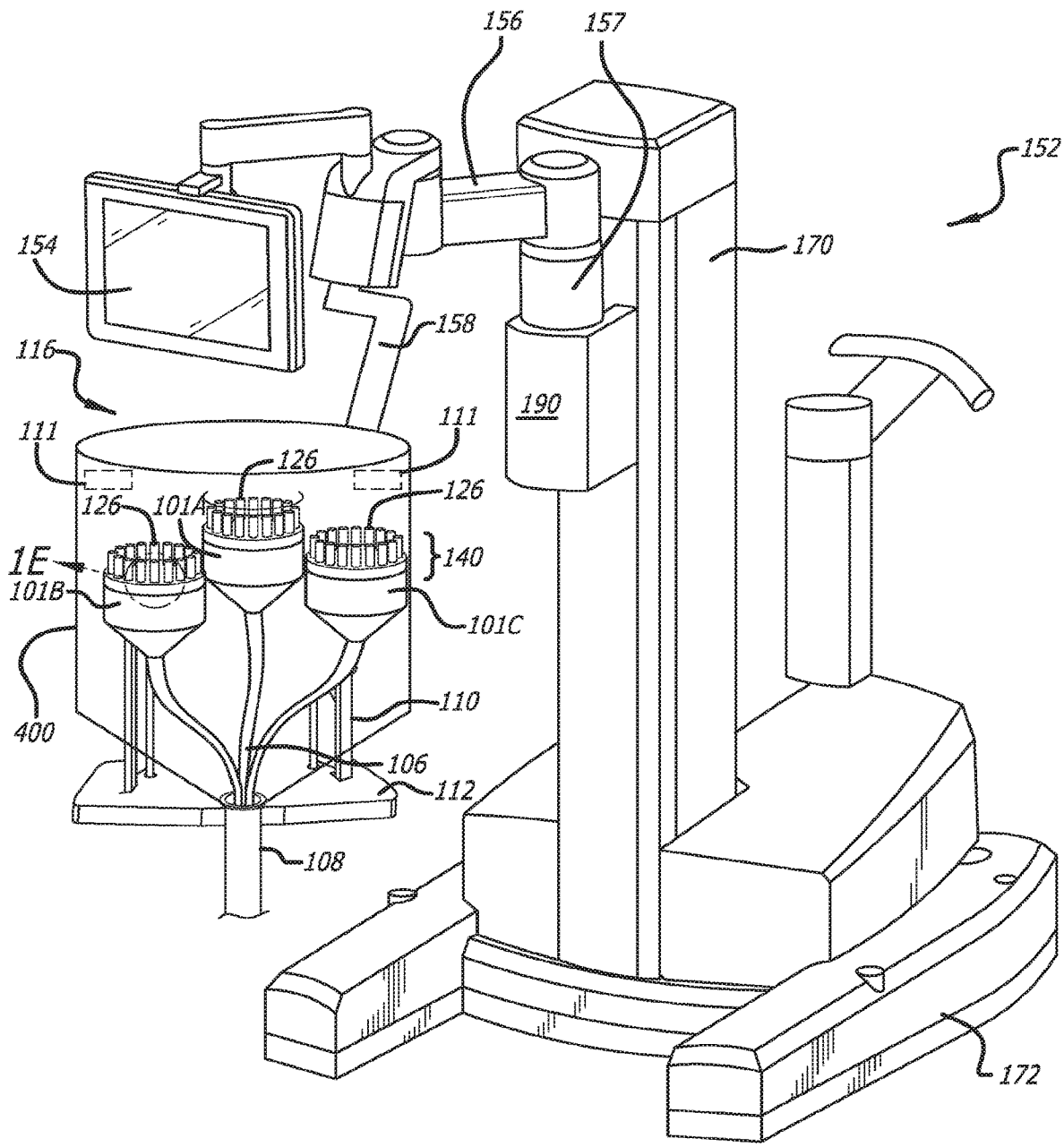
FIG. 1B is a perspective view of a patient side cart including a robotic surgical arm with a platform to support and move a proximal end of an entry guide and the robotic surgical tools that may be inserted therein.

Referring now to FIG. 1B, a perspective view of the robotic patient-side system 152 is illustrated. The robotic patient-side system 152 comprises a cart column 170 supported by a base 172. The robotic surgical arm 158 is attached to a set-up arm 156 that pivotally couples to the column 157 through a setup joint 157. The set up joint 157 is coupled to a carriage housing 190 so that the robotic surgical arm 158 may be raised and lowered and setup into position prior to surgery near the patient.

The robotic surgical arm 158 is a part of the positioning portion of robotic patient-side system 152. The robotic surgical arm 158 is used to control the actuation of the robotic instruments 101A-101C and the entry guide 108. The robotic surgical arm 158 includes an actuating end 116 with a moveable platform 112 to which the plurality of robotic instruments 101A-101C and the entry guide 108 may couple.

Figure 1C:
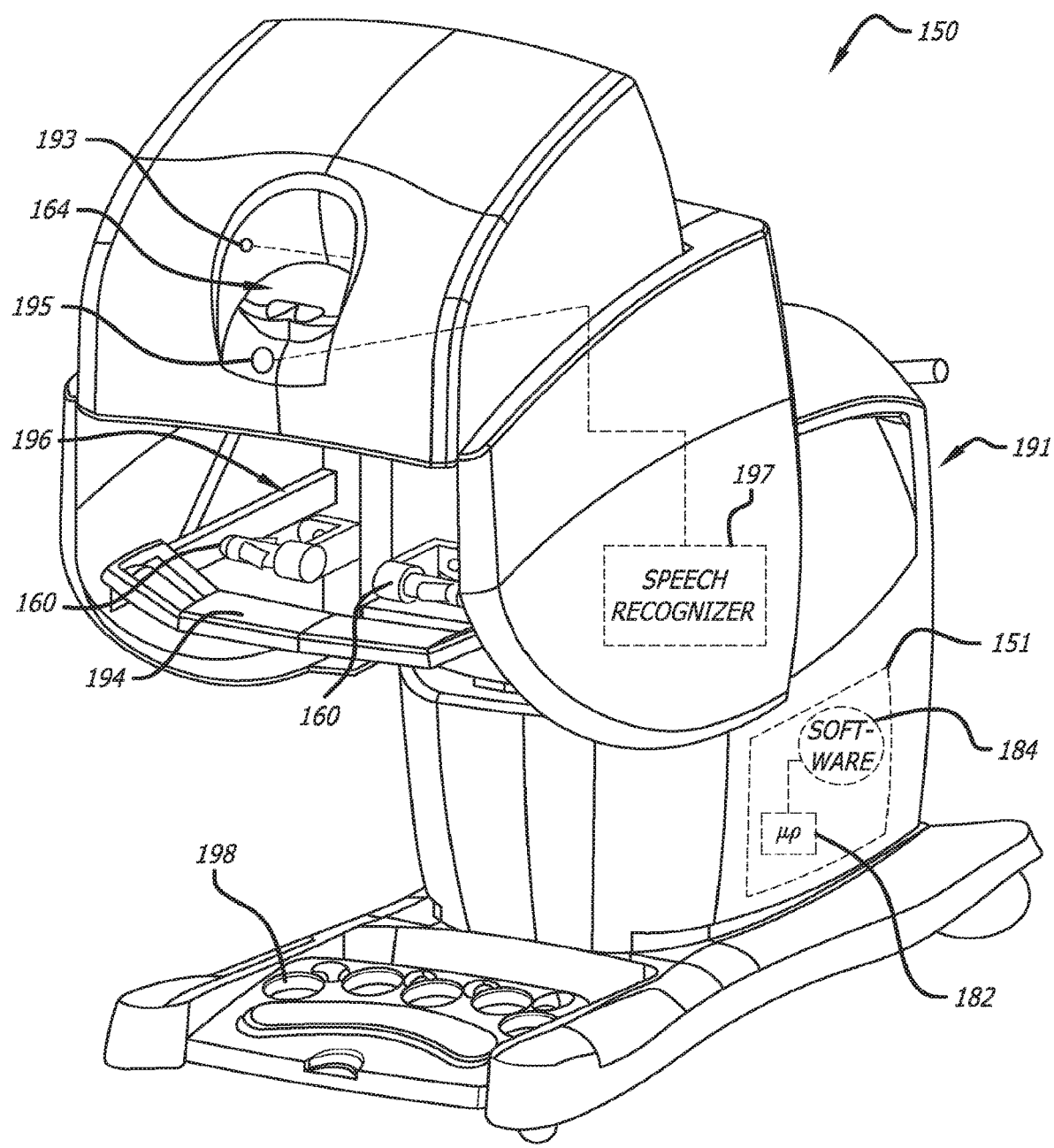
FIG. 1C is a perspective view of a robotic surgical master control console to control the robotic surgical arm and the insertion of the entry guide into a patient.

Referring now to FIG. 1C, a perspective view of the robotic surgical master control console 150 is illustrated. The master control console 150 of the robotic surgical system 100 may include the computer 151, a binocular or stereo viewer 164, an arm support 194; a pair of control input wrists, control input arms, and motion sensitive handles 160 in a workspace 196; foot pedals 198 (including foot pedals 318A-318B), and a viewing sensor 193. The master control console 150 may further include a microphone 195 and a speech recognitions system 197 coupled together and to the computer 151 for receiving audible commands and instructions.

The stereo viewer 164 has two displays where stereo three-dimensional images of the surgical site may be viewed to perform minimally invasive surgery. When using the master control console, the operator O typically sits in a chair, moves his or her head into alignment with the stereo viewer 164 to view the three-dimensional annotated images of the surgical site. To ensure that the operator is viewing the surgical site when controlling the robotic instruments 101, the master control console 150 may include the viewing sensor 193 disposed adjacent the binocular display 164. When the system operator aligns his or her eyes with the binocular eye pieces of the display 164 to view a stereoscopic image of the surgical worksite, the operator's head sets off the viewing sensor 193 to enable the control of the robotic instruments 101. When the operator's head is removed the area of the display 164, the viewing sensor 193 can disable or stop generating new control signals in response to movements of the motion sensitive handles in order to hold the state of the robotic instruments. The processing required for tool tracking and image guided surgery may be entirely performed using computer 151 given a sufficiently capable computing platform.

The arm support 194 can be used to rest the elbows or forearms of the operator O (typically a surgeon) while gripping motion sensitive handles of the control input wrists, one in each hand, in the workspace 196 to generate control signals. The motion sensitive handles are positioned in the workspace 196 disposed beyond the arm support 194 and below the viewer 164. This allows the motion sensitive handles 160 to be moved easily in the control space 196 in both position and orientation to generate control signals. Additionally, the operator O can use his feet to control the foot-pedals 198 to change the configuration of the surgical system and generate additional control signals to control the robotic instruments 101 as well as the endoscopic camera.

The computer 151 may include one or more microprocessors 182 to execute instructions and a storage device 184 to store software with executable instructions that may be used to generate control signals to control the robotic surgical system 100. The computer 151 with its microprocessors 182 interprets movements and actuation of the motion sensitive handles (and other inputs from the operator O or other personnel) to generate control signals to control the robotic surgical instruments 101 in the surgical worksite. The computer 151 and the stereo viewer 164 map the surgical site into the controller workspace 196 so it feels and appears to the operator that the motion sensitive handles 160 are working over the surgical site.

Figure 1D:
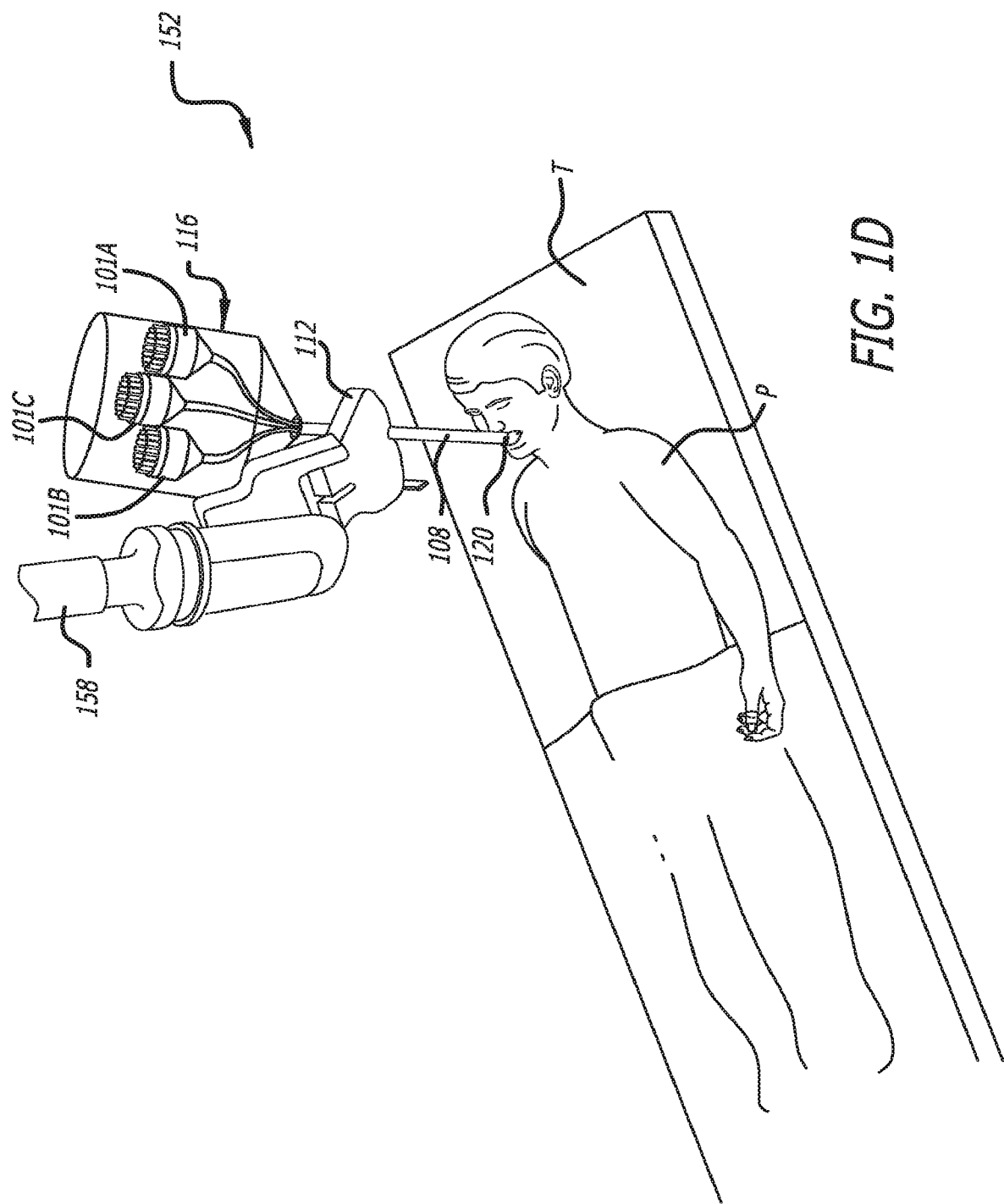
FIG. 1D is a magnified perspective view of a portion of a robotic patient-side system with a flexible guide tube for robotic surgical tools to perform minimally invasive surgery through a single port, and 1E is a magnified perspective view of an actuator assembly of a robotic patient-side system.
Figure 1E:
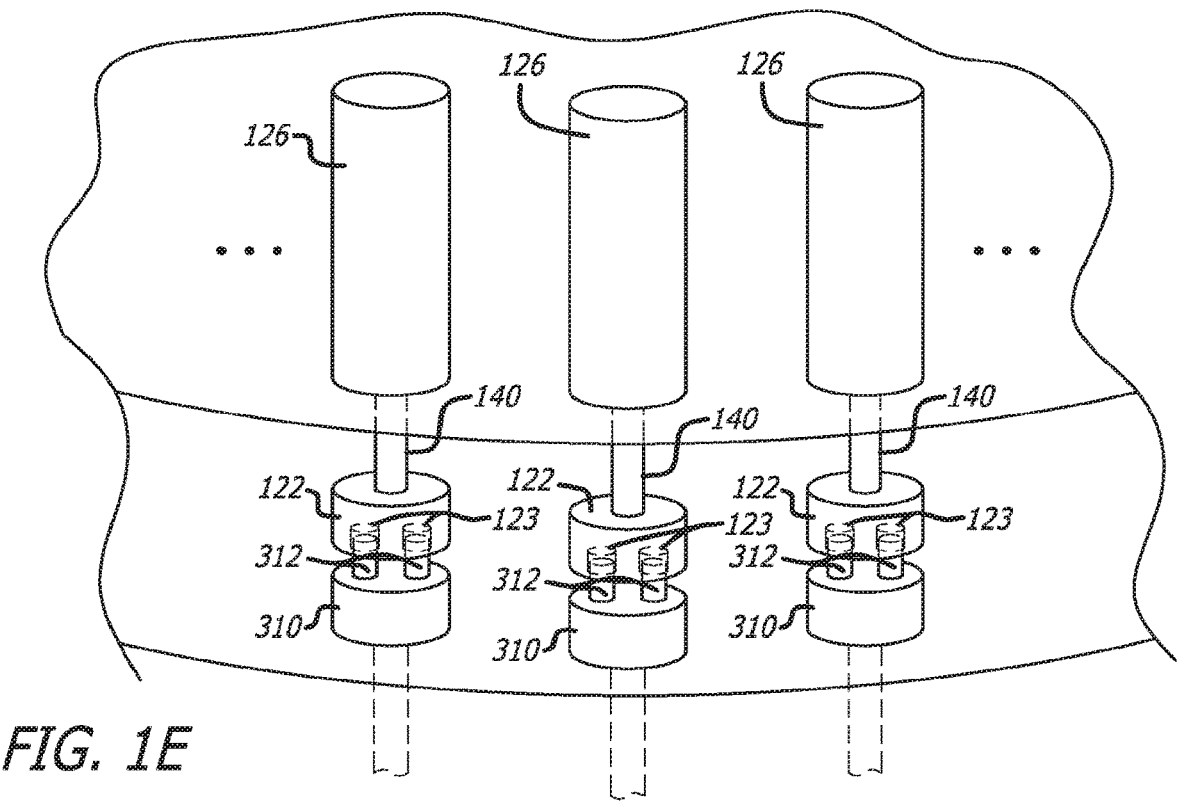

Referring now to FIG. 1D, a portion of the patient side cart 152 is illustrated with an actuating end 116 of a robotic surgical arm or manipulating arm 158. Other portions of the patient side cart 152 are illustrated in FIG. 1B to support the robotic surgical arm 158, the platform 112, the entry guide 108, and the tools or instruments 101 over a patient P.

The general function of the actuating end 116 of the robotic or manipulating arm 158 and the robotic surgical tools 101A-101C coupled thereto are described in more detail in U.S. patent application Ser. No. 11/762,165 entitled MINIMALLY INVASIVE SURGICAL SYSTEM filed by Larkin et al. on Jun. 13, 2007, which is incorporated herein by reference.

A single guide tube 108 supported by the platform 112 of the robotic arm 158 is used to insert the tools 101A-101C through an opening of the patient P, such as the patient's mouth for example. The guide tube 108 is coupled to the platform 112 which is in turn moveably coupled to the robotic arm 158. With one or more actuator mechanisms, the robotic arm can adjust the pitch, yaw, roll, and insertion along an insertion axis of the guide tube 108. The guide tube 108 may be maintained in a fixed position or rotated (e.g., pitch, yaw, and/or roll) around a remote center point 120 near the opening into the patient if permitted by the circumstances, including the tissue in the body where the tools may be located.

The robotic surgical tools 101A-101C may be inserted into the entry guide in varying degrees. For example, the robotic surgical tool 101B is illustrated as being more fully inserted into the guide tube 108 in comparison with the other robotic surgical tools 101A and 101C. The robotic surgical tools 101A and 101C are illustrated as being partially inserted into the guide tube 108 in FIG. 1D. The robotic surgical tools 101A-101B may be different types of robotic surgical tools.

Referring now to back to FIG. 1B, a proximal end of the robotic surgical tools 101A-101C are shown inserted into the guide tube 108 and coupled to a tool actuator assembly 140. Each tool 101A-101C may include a flexible body tube 106 inserted into the guide tube 108. The tool actuator assembly 140 is mounted to a linear actuator 110 (e.g., a servo-controlled lead screw and nut, or a ball screw and nut assembly) that independently controls each tool's further insertion within guide tube 108 along with its body tube's 106. The guide tube 108 may be removeably mounted to the support platform 112 as further explained herein with reference to FIGS. 4D-4F. Removable and replaceable guide tubes allow different guide tubes designed for use with different procedures to be used with the same telemanipulative system (e.g., guide tubes with different cross-sectional shapes or various numbers and shapes of working and auxiliary channels).

The actuator assembly 140 mates with and actuates components of the robotic surgical tools 101A-101C. The actuator assembly 140 includes a plurality of rotatable actuators 126 coupled to actuator disks 122. Each actuator disk 122 includes holes to interface to pins of rotatable interface disks of the robotic surgical tools. Each actuator disk 122 is rotated in response to control inputs from the master control console 150 to remotely control the robotic surgical tool.

The actuator assembly 140 may include one or more actuators 111 to actuate the entry guide 108. In one embodiment of the invention, the actuators may be the one or more servo-motors. For example, one or more actuators 111 may be used to actuate control cables to rigidize the entry guide 108 by actuating a locking tool inserted into or a part of the entry guide. In another embodiment of the invention, one or more actuators 111 may be used to actuate control cables to steer the distal end and other points along the length of the entry guide into the patient's body.

Figure 2:
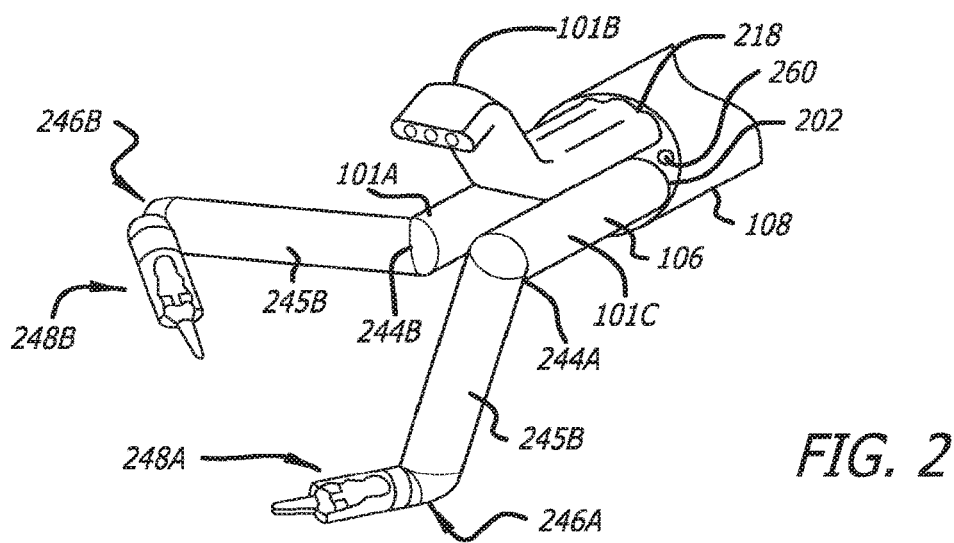

Referring now to FIG. 2, a distal end of the robotic surgical tools 101A-101C is shown extending out from the distal end of the guide tube 108. The guide tube 108 includes a plurality of channels or lumens 218, 202 through which the respective robotic surgical tools 101B, 101A-101B may be inserted and extend. The guide tube 108 may further include an auxiliary channel 260 through which other robotic surgical tools may be introduced or withdrawn, such as irrigation, suction, or cleaning devices for example. As illustrated in FIG. 2, the body tube or shaft 1006 of each respective robotic surgical tools 101A-101C may extend out from the respective channels or lumens of the guide tube 108. With the guide tube 108 entering natural orifices of a body its diameter and the diameter of each respective robotic surgical tool 101A-101C is limited.

Each of the respective robotic surgical tools 101A, 101C include end effectors 248A, 248B coupled to their respective body tubes or shafts 1006 by one or more joints 244A-244B, 246A-246B, and a parallel tube 245A-245B. In one instance, the body tubes or shafts 106 for the robotic surgical tools 101A, 101C is approximately 7 millimeters (mm) in diameter. In another instance, the body tubes or shafts 106 for the robotic surgical tools 101A, 101C is approximately 5 mm in diameter. Note larger diameter instruments can generally apply larger forces to tissue, but generally require a larger diameter entry guide, and thus the selection of instrument diameter can be procedure-specific.

Robotic Instruments with Flexible Shafts

Figure 3A:
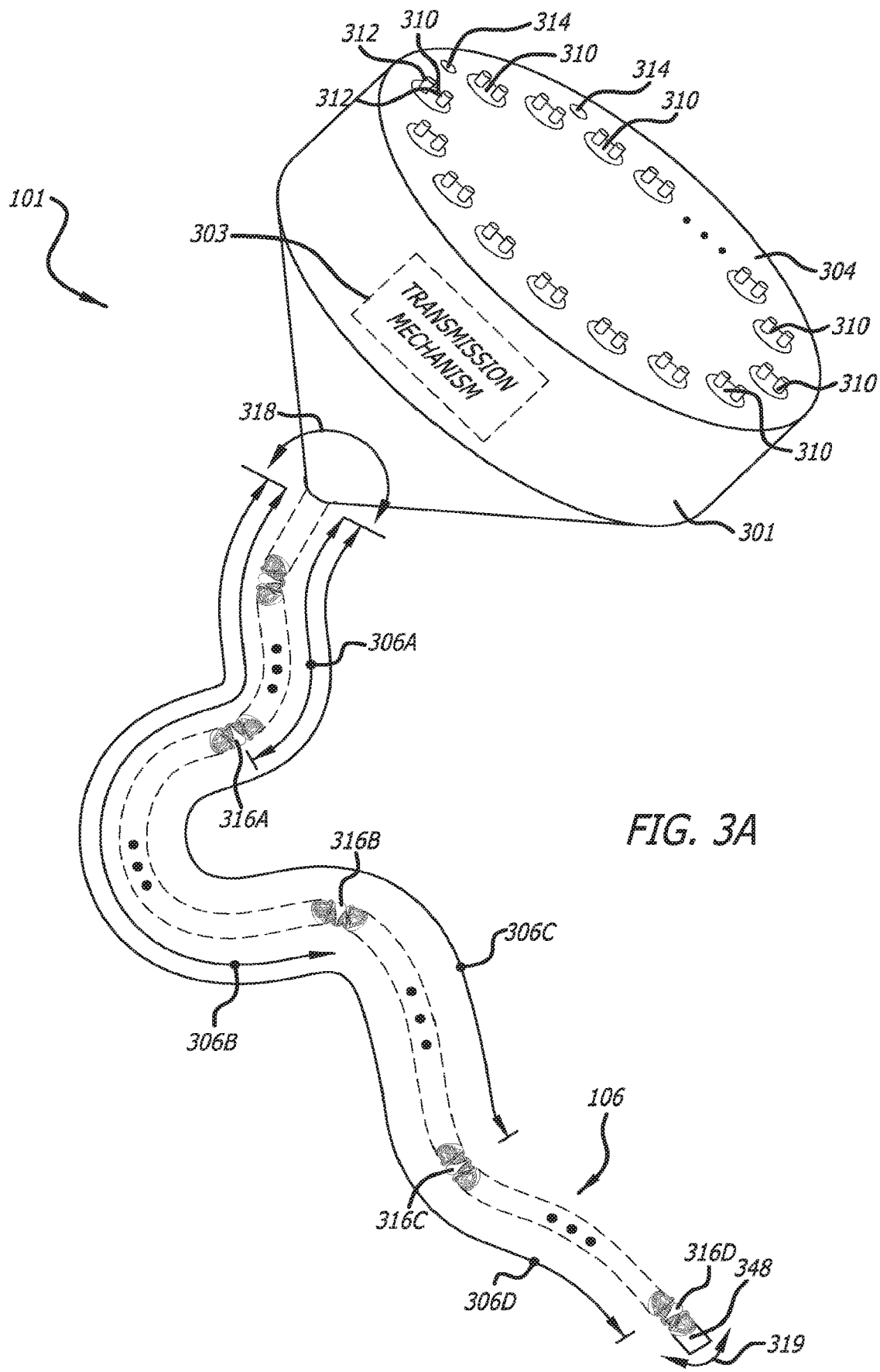
FIG. 3A is a perspective view of a robotic surgical tool with a flexible shaft for use with the flexible guide tube of the robotic surgical system.

Referring now to FIG. 3A, a perspective view of a robotic surgical tool 101 is illustrated. The robotic surgical tool 101 includes a housing 301 with a mountable base 304, a transmission mechanism 303, a body tube or shaft 106, and an end effector 348 coupled together. The housing 301 and the transmission mechanism 303 are coupled to the proximal end of the body tube 106 while the end effector 348 is coupled to the distal end of the body tube 106.

The end effector 348 is a steerable head and may be steered by control cables actuated by rotatable drivers 310. The shaft 106 may be formed of a plurality of pivotal vertebrae. The shaft 106 may include one or more steerable/lockable vertebrae 316A-316D actuated by additional control cables. Articulation of the vertebrae 316A-316D may steer sections of the shaft 106 where located. Tensioning of control cables coupled to the vertebrae 316A-316D may also lock one or more vertebrae in an articulated position to make one or more respective portions 306A-306D of the shaft rigid.

Figure 3B:
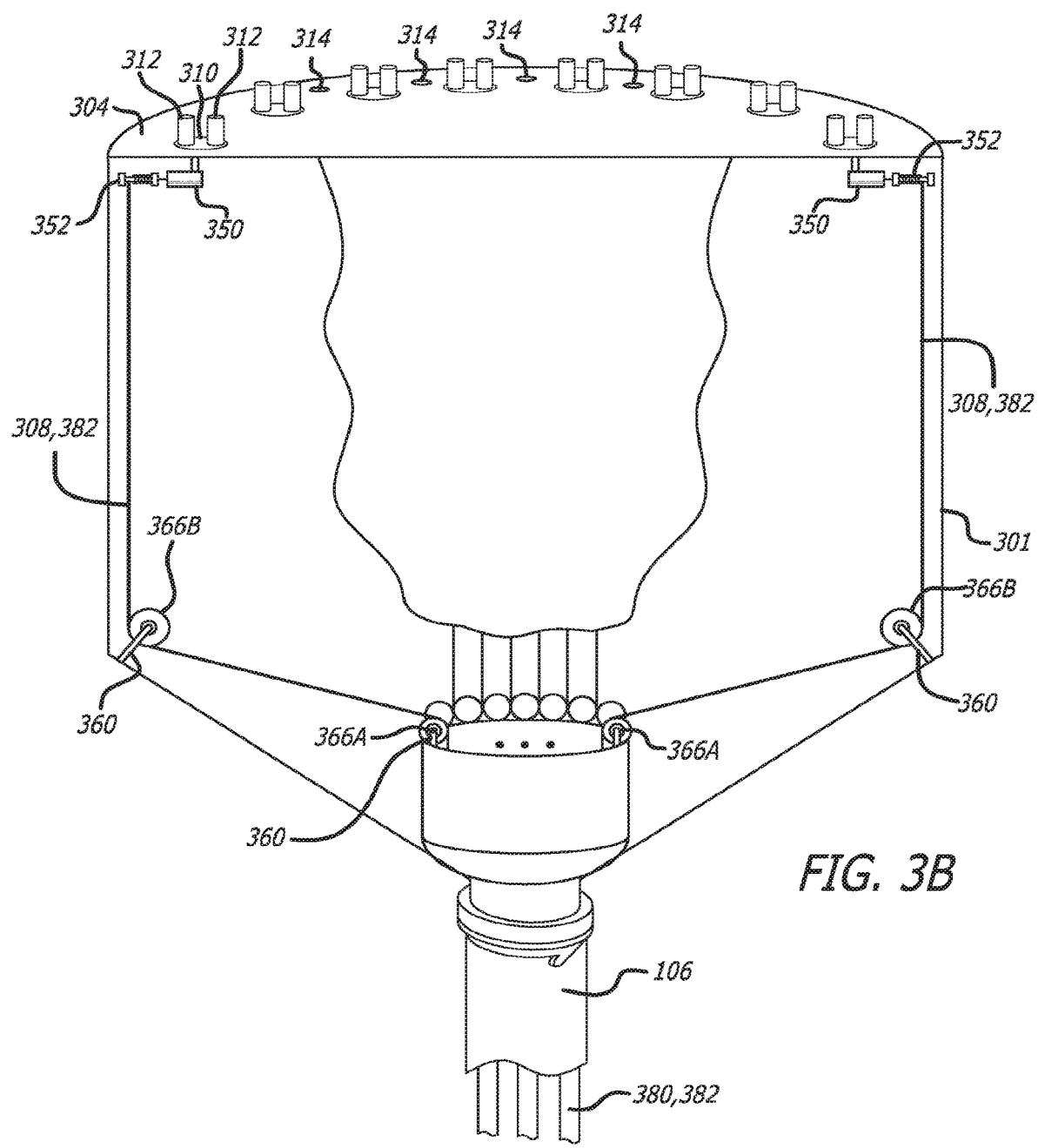
FIG. 3B is a cutaway perspective view of a proximal end of the robotic surgical tool of FIG. 3A is illustrated.
Figure 3C:
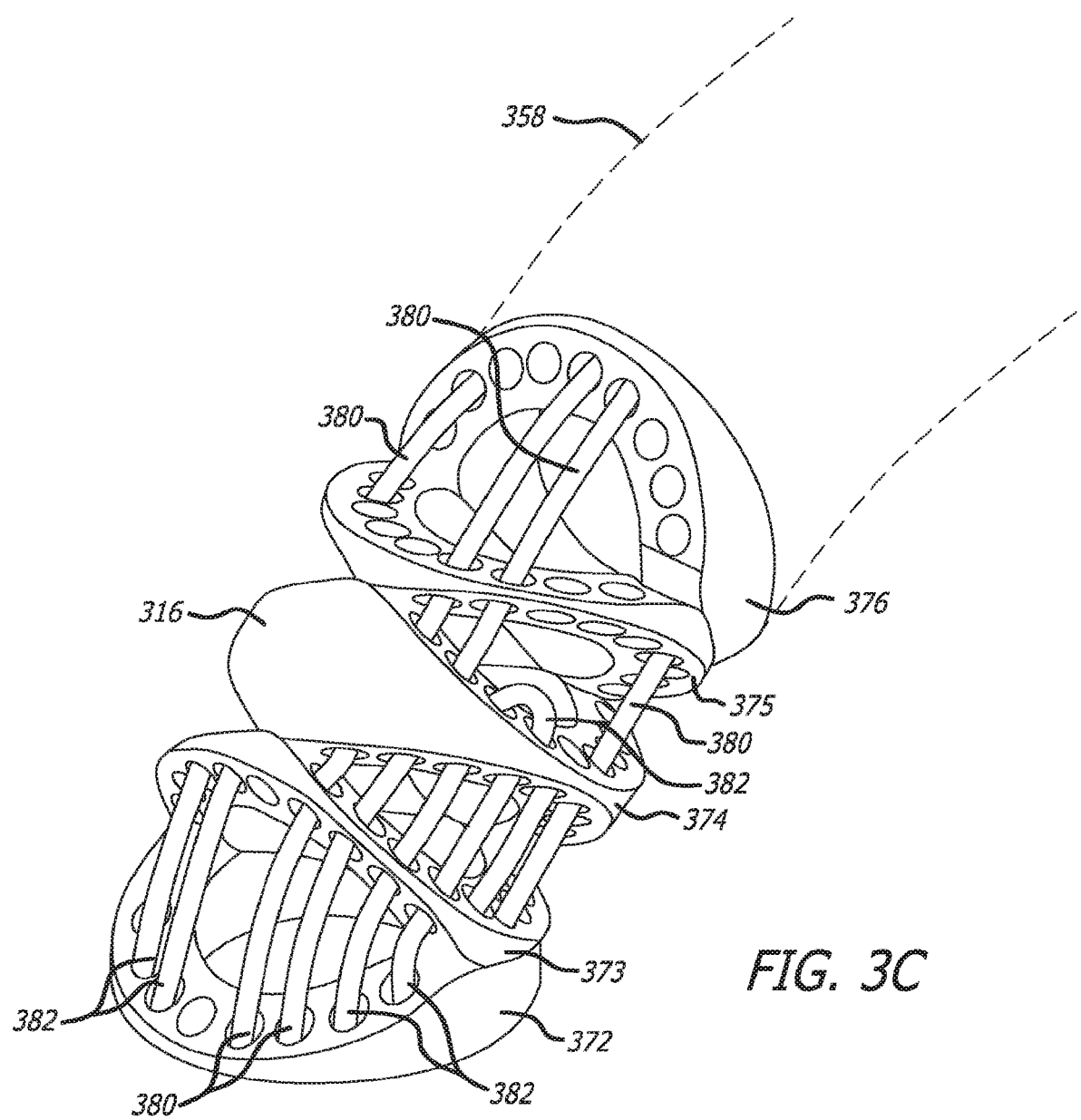
FIG. 3C is a perspective view of a portion of the flexible shaft of the robotic surgical tool.

FIG. 3C illustrates a plurality of pivotal vertebrae 372-376. The vertebrae 374 is one of the steerable/lockable vertebrae 316 that may be steered by a plurality of control cables 382 on opposing sides that extend from the proximal end of the shaft to the vertebrae 316. The end effector 358 may couple to the last vertebrae near the distal end of the shaft 106. The pivotal vertebrae 372-376 for the shaft 106 are described in further detail in U.S. Pat. No. 6,817,974 entitled SURGICAL TOOL HAVING POSITIVELY POSITIONABLE TENDON-ACTUATED MULTI-DISK WRIST JOINT filed by Thomas G. Cooper et al. on Jun. 28, 2002, which is incorporated herein by reference.

Referring back to FIG. 3A, the transmission mechanism 303 provides a mechanical interface for the tool 101 and includes a plurality of rotatable interface disks 310. One or more of the rotatable interface disks 310 are associated with a degree of freedom of the robotic surgical tool 101. For example, a rotatable interface disk 310 may be associated with instrument body roll degree of freedom illustrated by the doubled-headed arrow 318. The rotatable interface disks 310 may be arranged for compactness. Each rotatable interface disk 310 may include a pair of spaced apart raised pins 312. The raised pins 312 of each rotatable interface disk may be spaced eccentrically to provide proper disk orientation when mated with an associated actuator disk. In other embodiments of the invention, the transmission mechanisms may be directly coupled to motors or other actuators, or may be coupled by other detachable coupling means known in the art.

The transmission mechanism 303 includes a plurality of mechanical components (e.g., gears, levers, gimbals, cables, springs, etc.) to convert roll torques 320 received by the rotatable interface disks 310 and transmit the torque to control cables to actuate end effectors, to steer the end effector and portions of the shaft, and rigidize portions of the shaft. The movement of the robotic surgical tool 101 may be controlled, such as roll 318 in the body tube 106 or pitch 319 in the end effector 348, for example. One or more cables, cable loops (e.g., 380,382), hypodermic tubes, flexible push rods, and/or any combination thereof within the shaft 106 may be used to transfer the torque received by the transmission mechanism 303 to the lockable/steerable vertebrae 316 along the shaft 106, such as the vertebrae 374, to steer the end effector 348 and portions of the shaft.

The housing 301 may include one or more electronic interface connectors 314 to provide an electronic interface for the robotic surgical tool 101. The one or more of the electronic interface connectors 314 may be used to interface to one or more cameras in the end effector 348. The one or more of the electronic interface connectors 314 may be used to pass information stored in a semiconductor memory integrated circuit to the master control console regarding the tool and its end effectors. Such passed information may include instrument type identification, number of instrument uses, and the like. The control system may be used to update the stored information (e.g., to record number of uses to determine routine maintenance scheduling or to prevent using an instrument after a prescribed number of times). Other connectors for, e.g., optical fiber lasers, optical fiber distal bend or force sensors, irrigation, suction, etc. may be part of the housing 301.

Referring now to FIG. 3B, exemplary drive mechanisms and cable connections are illustrated at a proximal end of a tool 101 for steering the steerable/lockable vertebrae and end effector. The tool 101 may have one actuator per control cable 380,382. Each actuator may be coordinated by a control system to pitch and yaw the steerable vertebrae in the shaft with the control cables to follow various motion profiles.

For each control cable 380,382 the transmission mechanism may include one or more pulleys 366 to direct the cable to a spool or capstan 352 to pay in or out the cable. The proximal end of the drive cables 380,382 are wrapped around the capstan 352 to control the movement of the steerable/lockable vertebrae and end effector. The capstan 352 is coupled to a first shaft 354 of a transmission 350. A second rotatable shaft 356 of the transmission 350 extends through the base 304 and is coupled to the rotatable receiver 310. The one or more pulleys 366 are pivotally coupled to one end of a shaft 360 with the opposite end of the shaft 360 being coupled to the housing 301.

Each rotatable receiver 362 of the tool mates with a rotatable driver of the robotic surgical arm when mounted thereto. As the rotatable receivers 362 are driven by a rotatable driver of the robotic surgical arm, the transmission transfers the rotational motion to the capstan 352 to take in or pay out the control or drive cables 380,382. A plurality of rotatable receivers 362 may be simultaneous driven to move a plurality of drive cables 380,382 in the shaft 106 to obtain a mixture of pitch and yaw movement in one or more steerable vertebrae.

The drive cables 380,382 may be controllably actuated by a variety of alternative actuators and drive mechanisms, such as motor-driven linkages, hydraulic actuators, electromechanical actuators, linear motors, magnetically coupled drives and the like.

Lockable Flexible Entry Guide

Figure 4A:
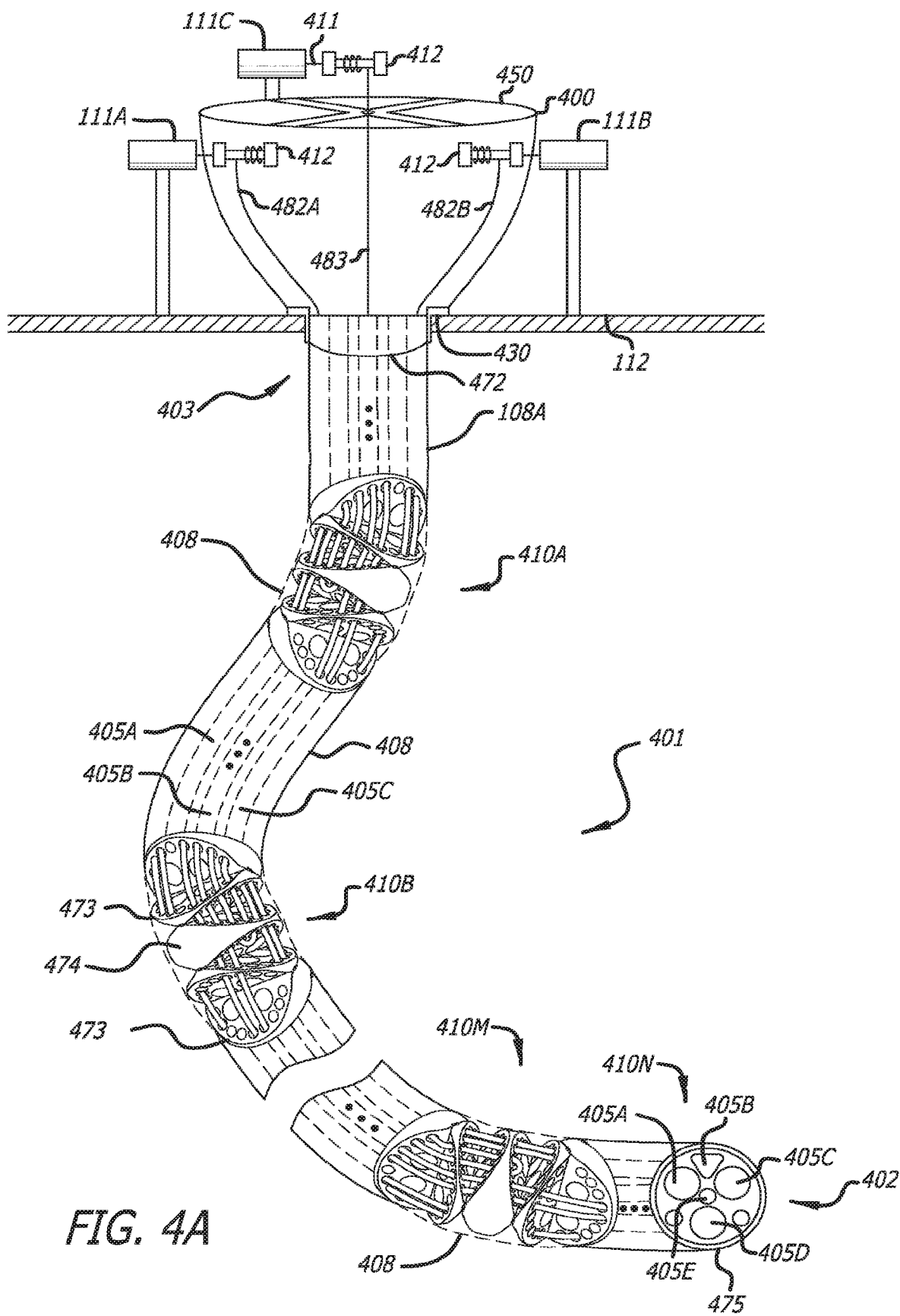
FIG. 4A is a perspective view of an entry guide having a proximal end coupled to the platform.

Referring now to FIG. 4A, a perspective view of an entry guide 108A is shown for one embodiment of the entry guide 108. The entry guide 108A has a proximal end 401 and a distal end 402. The entry guide 108A may have a cylindrically shaped cross-section which may be circular as shown or of a non-circular shape, such as a rectangular or oval shape.

The entry guide 108A may be formed of a plurality of pivotally coupled vertebrae 472-475. The vertebrae 472-475 are rigid segments that are assembled together to be flexible. Alternatively, the entry guide may be formed of a flexible material such as a high performance engineering thermoplastic (e.g., polyoxymethylene, DELRIN by Dupont, or a linear aromatic polymer PolyEtherEtherKetone (PEEK)). In this case, the entry guide may be shaped (e.g. notched or corrugated) to provide one or more regions of higher flexibility along its length by reducing the diameter or the thickness in one direction perpendicular to the major axis. The entry guide 108A may be covered by a flexible sheath or sleeve 408 to provide a smooth surface to avoid snagging tissue in the body cavity and keep out fluids and tissue to ease cleaning.

The entry guide 108A includes one or more instrument lumens 405A-405E which guide a respective one or more inserted surgical tools from the proximal end to the distal end of the entry guide. After the entry guide is inserted, the instrument lumens provide the routing for a flexible shaft of a surgical tool to reach the surgical site. During a surgical procedure, instruments may be withdrawn via these lumens and replaced with other instruments.

The instrument lumens may be hollow open ended cylindrical passages within the entry guide extending from the proximal end to the distal end. In some cases, the entry guide may have a lumen that is open at the proximal end of the entry guide but closed near the distal end. In this case, a fixed tool substantially aligned with an axis of the lumen at the closed end may be included in the distal end of the entry guide 108A (see FIG. 5A). For example, an electronic tool, such as a CCD camera for capturing video images and/or one or more light emitting diodes for lighting, may be provided in the distal end of the entry guide 108A beyond the closed lumen opening.

The instrument lumens, such as instrument lumens 405A, 405C,405D, may be of the same size and shape to receive commonly designed robotic surgical tools with the similar cross-sectional dimensions but different capabilities. In one embodiment of the invention, the robotic surgical tools have a circular cross section. Other instrument lumens, such as lumen 405B, may have a different shape (e.g., rectangular or triangular like shape) along a portion of the entry guide (such as the distal end) so that the shaft of the tool inserted therein is keyed to the lumen so that it rotates with that portion of the entry guide, such as for maintaining endoscopic camera orientation. Alternatively, a locking device may be used to couple a portion of a shaft of a tool to the lumen wall of the entry guide, such as shown and described with reference to FIGS. 5D-5E. The locking device between the tool shaft and the lumen wall may also be referred to as a lumen attachment device or mechanism for attaching a portion of the tool shaft to the lumen wall of the entry guide.

One or more locking devices may be positioned along the length of the shaft and/or lumen wall of a lumen to couple the shaft of a tool to differing positions along the entry guide. For example, intermediate portions of the entry guide may be steered by a tool attached at intermediate portions of the lumen. A plurality of attachment mechanisms may be positioned along a given lumen of the entry guide or along a given instrument/tool. The plurality of attachment mechanisms may be selectively enabled and disabled to selectively couple differing portions of the tool shaft to differing portions of a lumen wall of the entry guide. The different positions of the attaching mechanisms may allow for pushing and/or pulling on the instruments/tools to steer some intermediate or distal portion of the entry guide.

A torque applied at a proximal end of the shaft of a tool inserted into and locked or keyed to lumen 405B may be able to rotate a portion of the entry guide 108A, such as the distal end. Alternatively, rotation of the shaft of a tool inserted into and locked or keyed to the lumen 405B of the entry guide 108A may be deterred. An endoscopic camera, for example, inserted into the lumen 405B and keyed thereto will maintain its point of view with respect to the distal end of the entry guide 108A and other surgical tools extending out from the end of the entry guide. With the shaft of a tool keyed to the lumen, external torques applied to the instrument tip, resulting in rolling moments about the longitudinal axis of the instrument where it exits the lumen, may be transmitted to the entry guide, which may be locked to provide a torsionally stiff platform to react to the external torques.

Other lumens may be smaller in size, such as lumen 405E, to receive a special type of tool, such as a locking or stiffening tool and to minimize cross-section area being used. The lumens may be strategically located in the cross-section to provide maximum functional effect. For example, the lumen 405E that may be used to rigidize the entry guide, may be located along a center axis of entry guide 108A. The lumens may, for example, be positioned on opposite sides (e.g., left and right sides) so that the robotic surgical tools inserted therein may exert maximum leverage when used to assist in steering the entry guide 108A. In one embodiment of the invention, the length of the entry guide 108A may be approximately one meter to extend through a body cavity and the diameter may be approximately twenty millimeters to allow a plurality of robotic surgical tools with flexible shafts to be inserted therein.

The proximal end 401 of the entry guide 108A may be removeably coupled to the platform 112 by a fastening means 430. Embodiments of the fastening means 430 to couple the entry guide to the platform are illustrated in FIGS. 4D-4F. The platform 112 supports the entry guide 108A and its housing 400 over the patient such that gravity may assist in the insertion of the entry guide 108A into the patient's body. The platform 112 may be moved to support the entry guide at different angles. The platform 112 may be manually moved by use of the set-up arm 156, set up joint 157 and the carriage housing 190 coupled to the column 157 of the patient side cart 152. The platform 112 may be robotically moved by remote control by use of the robotic arm 158 that can be manipulated by a surgeon O at the master control console 150.

The entry guide 108A may include one or more steering cables 482A-482B that may be used to steer at steering points 410A-410N along the length of the entry guide under computer control. The steering point 410N at or near the distal end 402 is used to steer the distal end 402 of the entry guide 108A while steering points 410A-410M are used to steer the body of the entry guide 108A. The entry guide 108A or a locking tool may include one or more locking cables 483 to rigidize the flexible entry guide 108A along its spine. The steering cables 482A-482B when pulled concurrently may be used to further rigidize the flexible entry guide 108A.

The steering cables 482A-482B may be taken in and paid out by one or more actuators 111A-111B, respectively under remote control by a computer, such as the computer 151 at the master console 150. One or more locking cables 483 may be may be taken in and paid out by one or more actuators 111C under remote control by a computer, such as the computer 151 at the master console 150.

The rotating motion of a rotating actuator may be simply coupled to a cable by a spool or a capstan. For example, steering cables 482A-482B and locking cables 483 are each routed from the flexible shaft 401 into the bell shaped housing 400 and couple to a spool or capstan 412 such as by wrapping around it. The capstan 412 is coupled to one end of a rotatable shaft 411 extending through the housing 400 and coupled to an actuator. In this case, the actuators 111A-111C may be rotatable actuators.

Figure 4B:
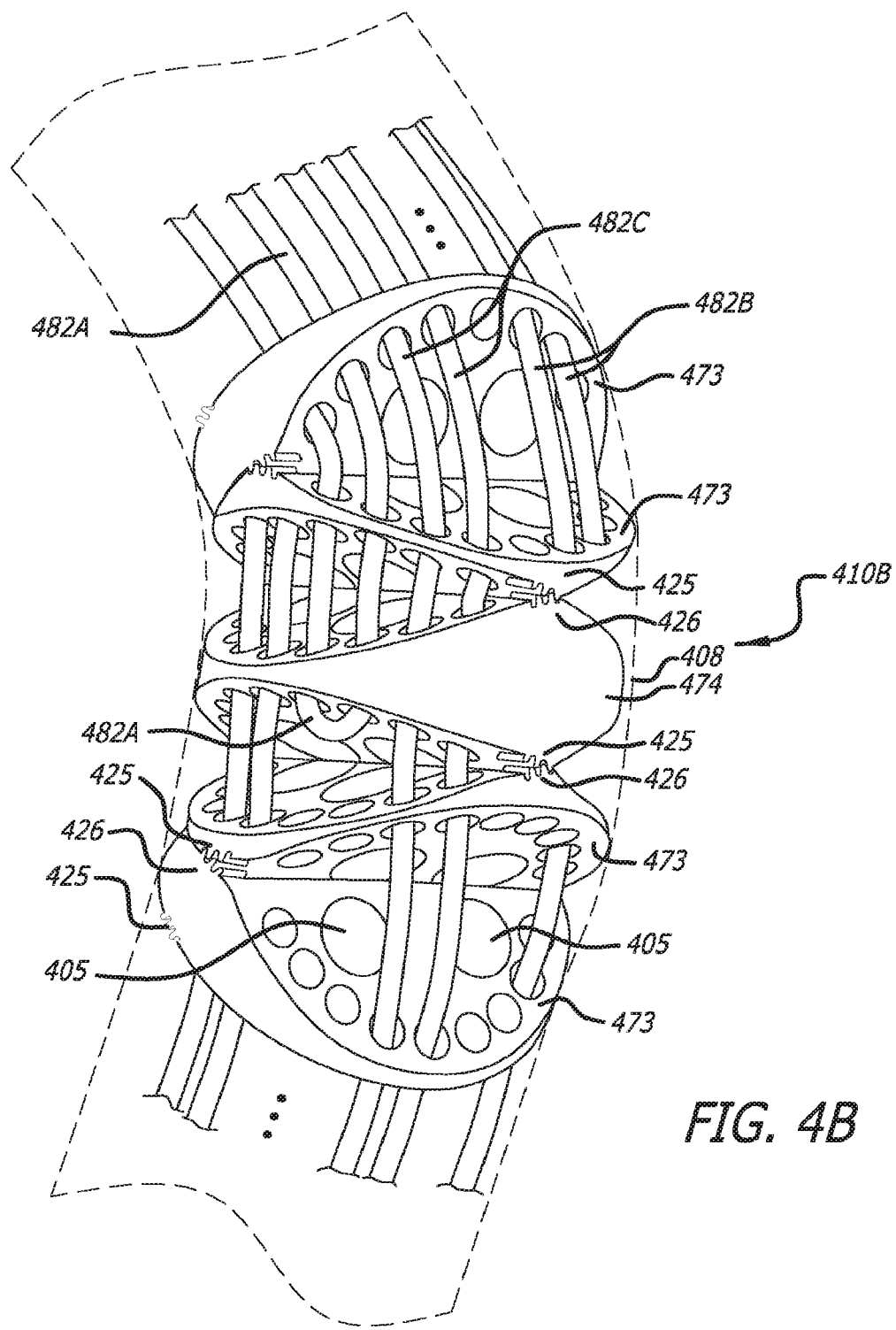
FIG. 4B is a perspective view of a portion of the flexible entry guide of FIG. 4A.

Referring now to FIG. 4B, a perspective view of a series of vertebrae 473-474 of the entry guide 108A at a body steering point 410 are illustrated. A plurality of steering cables 482A-482C are threaded through cable guide openings 421 in each of the vertebrae 473-474. The steering cables may be doubled in a cable loop such as steering cable 482A for increased strength. The steering cable 482A is coupled to the steering/lockable vertebrae 474 by a loop end so that it can actuate the entry guide at the body steering point 410. Other steering cables, such as steering cable 482C, may be routed past the body steering point 410 to actuate a more distal body steering point, such as point 410N.

The vertebrae 473-474 and adjacent vertebrae 473 can pivot against each other at the meshing of a pair of lower gear segments 425 with a pair of top gear segments 426. One or more alignment pins and alignment openings may also be used between adjacent vertebrae to retain the orientation of adjacent vertebrae.

Figure 4C:
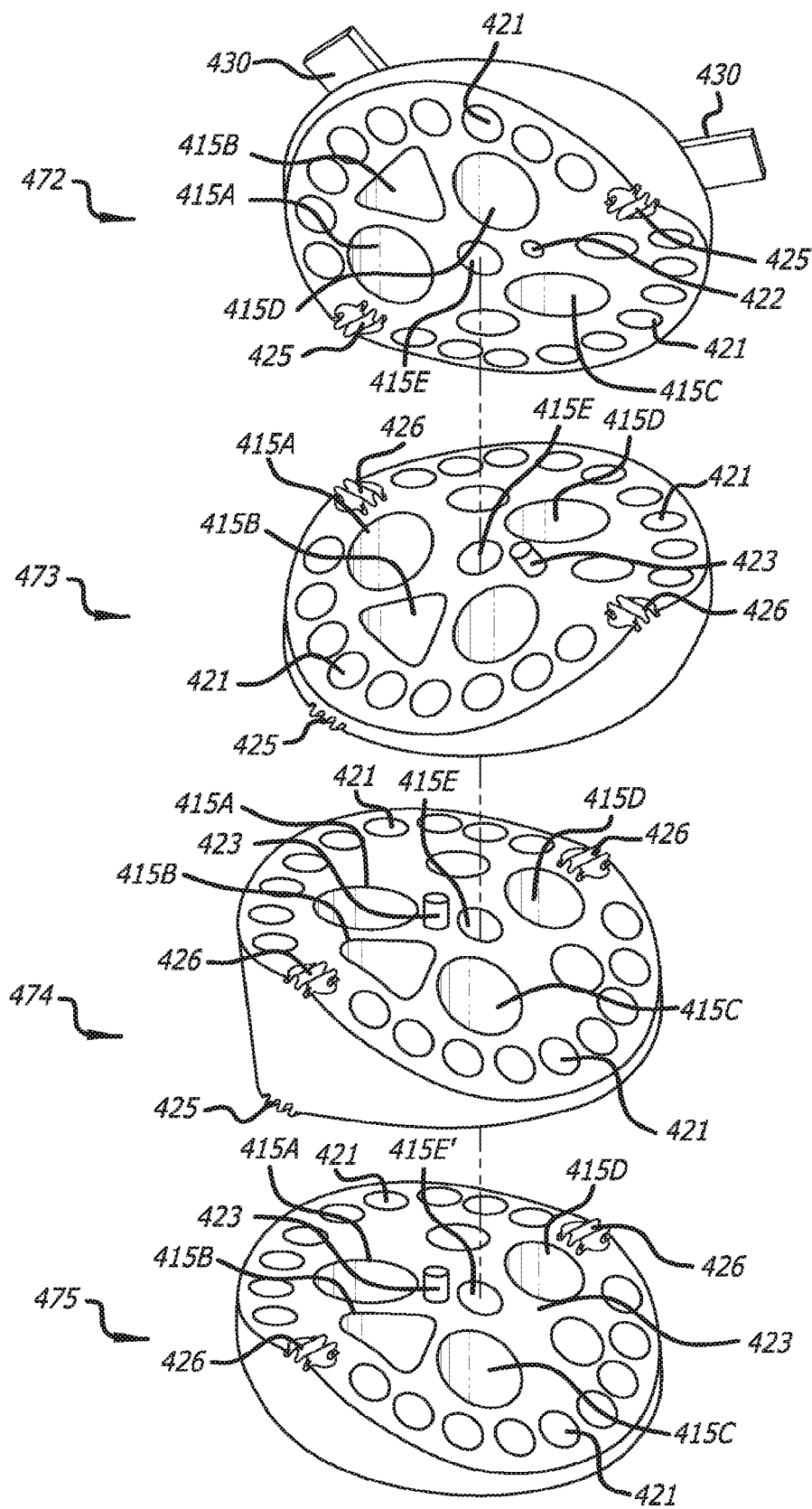
FIG. 4C is an exploded view of the various vertebrae that form flexible entry guide of FIG. 4A FIGS. 4D, 4E, and 4F are top views of how the entry guide may couple to the platform.
Figure 4D:
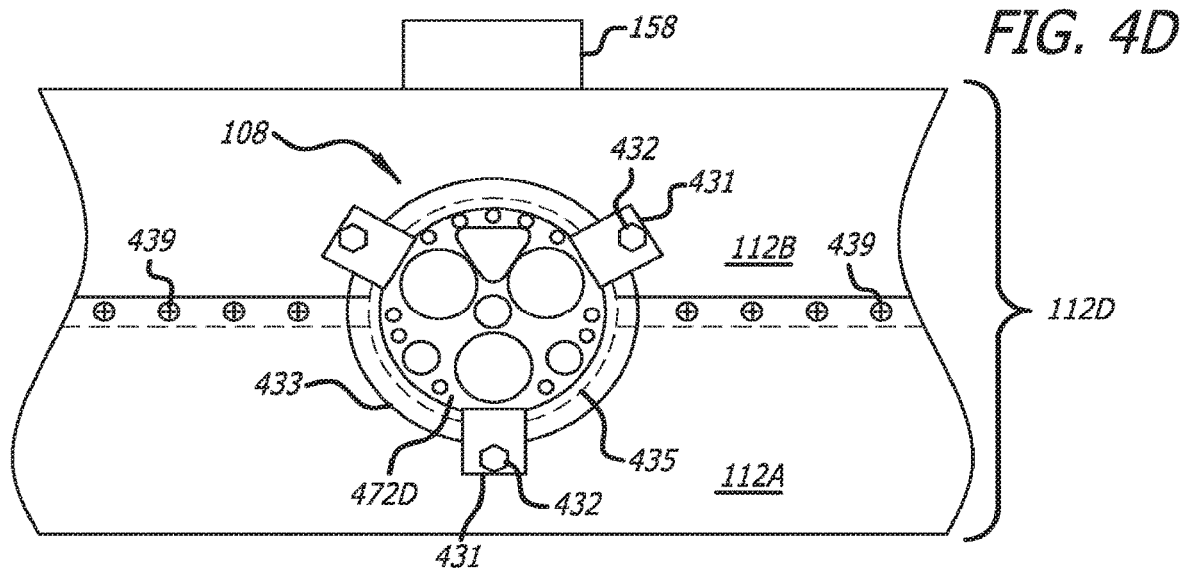
FIG. 4G is a perspective view of another entry guide having a proximal end coupled to the platform.
Figure 4E:
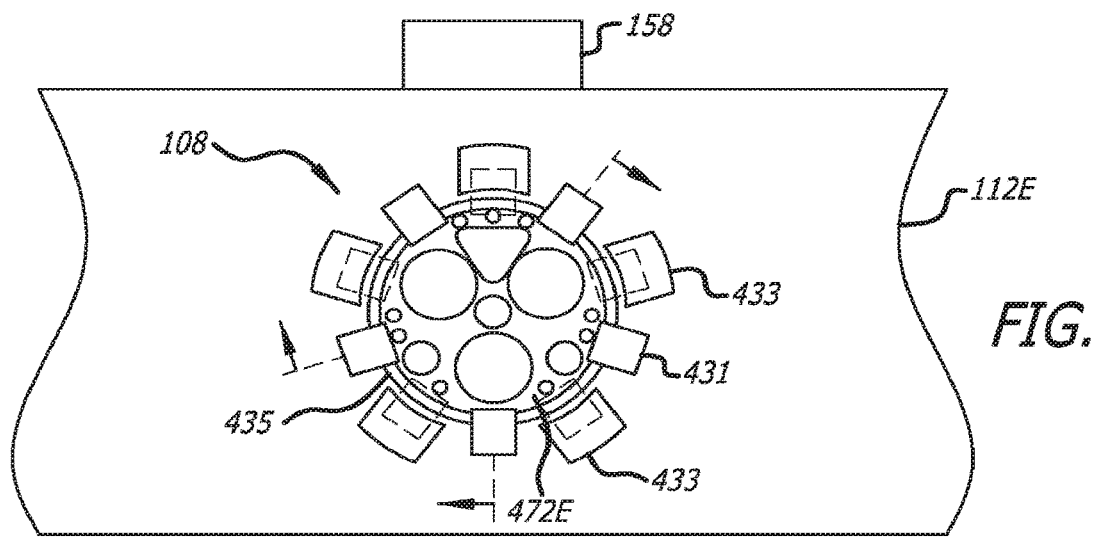
Figure 4F:
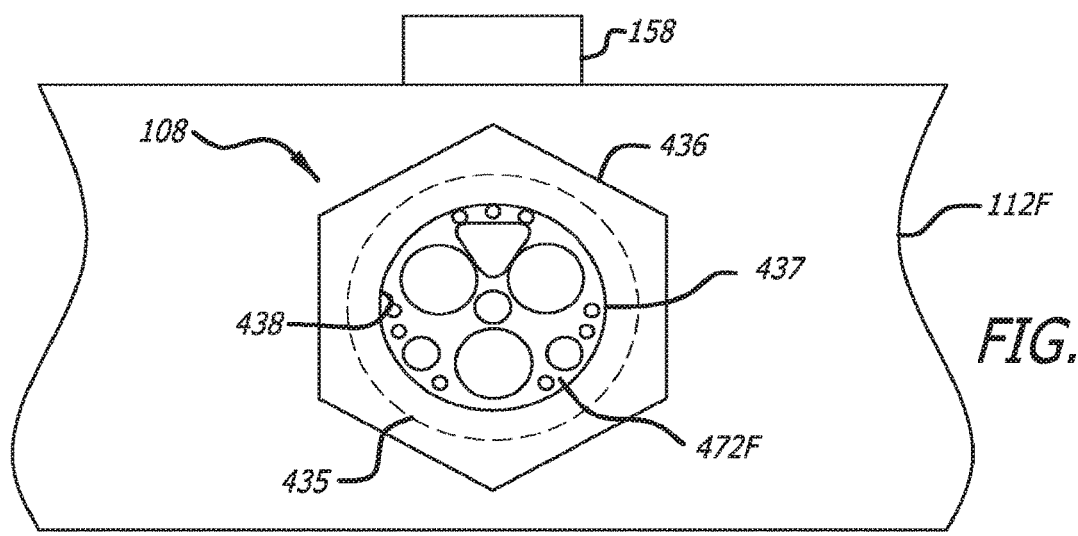

Referring now to FIG. 4C, an exploded view of vertebrae 472-475 of the entry guide 108A are illustrated without any steering or locking cables. Each of the vertebrae 472-475 include a plurality of openings 415A-415E that when flexibly assembled together form the lumens 405A-405E. Each of the vertebrae 472-475 includes a plurality of cable guide openings 421 through which the control cables may be inserted. The edges of the openings 415A-415E may be shaped to maximize the radii of curvature of the surfaces which contact the steering and locking cables when the entry guide is articulated to minimize friction and wear between the cables and the vertebrae.

The vertebrae 472 is at the proximal end of the entry guide and may include a fastening means 430 to couple to the platform 112. The fastening means 430 may be tabs as shown for a bayonet mount or a lip around outer edge with an engagement mechanism to couple the proximal end of the entry guide 108A to the platform 112. The vertebrae 472 has a pair of bottom gear segments 425 to mate with a pair of upper gear segments 426 of another vertebrae. The vertebrae 472 further has one or more alignment openings 422 on opposing sides to mate with respective one or more alignment pins 423 to keep adjacent vertebrae in alignment.

The vertebrae 473-474 are used between the proximal end and the distal end of the entry guide 108A. Each of the vertebrae 473-474 includes a pair of top gear segments 426 on a top surface and a pair of bottom gear segments 425 on a bottom surface. The top and bottom gear segments may be aligned with each other as shown by vertebrae 474 or they may be turned by ninety degrees, or another angular increment, as shown by vertebrae 473. Each of the vertebrae 473-474 may include one or more opposing alignment pins 423 in a top side to mate with openings of another vertebrae and one or more opposing alignment openings 422 in a bottom side to mate with pins of another vertebrae to prevent axial translation along the pivot line of one vertebra relative to the next.

The vertebrae 473-474 may be of the same thickness for uniformity or differing thickness. For example, the vertebrae 474 may have a greater thickness in order to vary the bend characteristics of the entry guide along its length.

An end vertebrae 475 is at the distal end of the entry guide 108A and may have one or more robotic surgical tools extend from it into the surgical site through openings 415A-415D, 415E'. However, the vertebrae 475 may include one or more openings, such as opening 415E' with a top opening and a closed bottom to form a closed distal end of a lumen so that a tool, such as a camera may be integrated into the entry guide 108A. FIG. 10 illustrates a camera 1002 integrated into the distal end of an entry guide behind a lumen 405B' with a closed distal end. The vertebrae 475 has a pair of upper gear segments 426 to mate with a pair of bottom gear segments 425 of vertebrae above it. The vertebrae 475 further may have one or more alignment pins 423 on opposing sides to mate with one or more alignment openings 422 on opposing sides in the neighboring vertebrae.

The vertebrae of the entry guide 108A are formed of metal, such as stainless steel, in accordance with an aspect of the invention. Alternate embodiments of the entry guide 108 may be formed of other materials such as composite materials, e.g. carbon-epoxy composite, high strength plastics, e.g. acetal, polycarbonate, PolyEtherEtherKetone (PEEK), or the like.

Figure 4G:
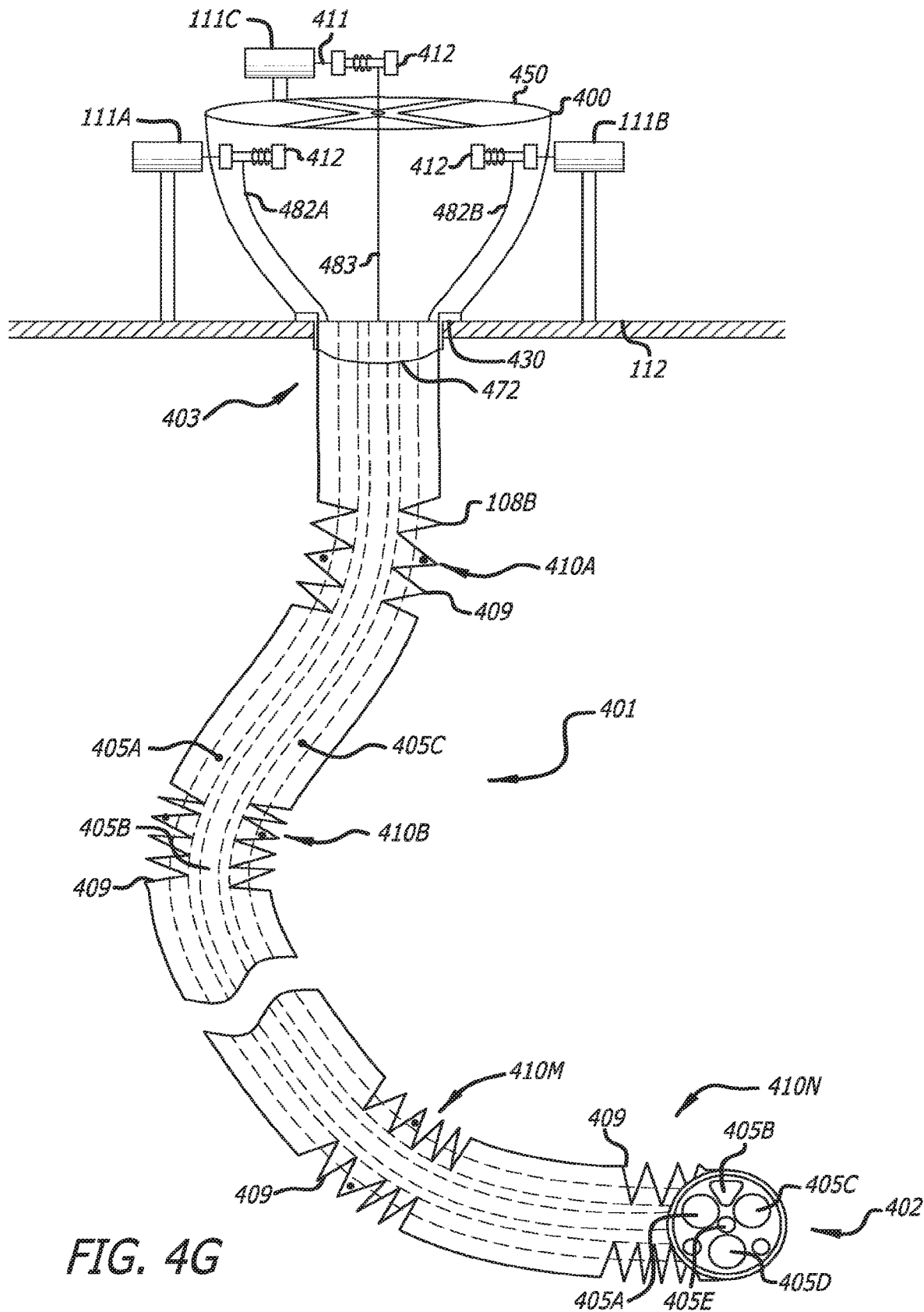

Referring now to FIG. 4G, a perspective view of an entry guide 108B, an alternate embodiment of the entry guide 108, is shown. The entry guide 108B may have similar elements and features of the entry guide 108A, such as the lumens 405A-405E. However instead of being formed of metallic vertebrae, the entry guide 108B is formed of a high performance flexible plastic (e.g., polycarbonate, acetal, or a linear aromatic polymer such as PolyEtherEtherKetone (PEEK)), high durometer natural or synthetic rubber, or other flexible material. The entry guide 108B may be periodically notched with a series of linear notches 409 near a plurality of steering points 410A-410N so that it may sufficiently flex to make turns as it is inserted into a body cavity. The linear notches 409 are v-shaped grooves. The linear notches 409 may alternatively be corrugation. A flexible sheath or sleeve 408 (see FIG. 4A may hide from view the linear notches or corrugation 409 as well as keep debris from the notches as the entry guide is inserted into a body cavity. The corrugation 409 may be circular corrugation or non-circular corrugation in one embodiment of the invention. The high performance flexible material may be less expensive to manufacture and assemble into an entry guide 108B. An entry guide 108B formed of inexpensive materials may be used once and disposed of afterwards without having to undergo a sterilization process. Devices disclosed herein may provide additional stiffness to ease insertion of the flexible entry guide 108B.

FIGS. 4D-4F illustrate top views of different embodiments of how the entry guide 108 may be supported and mounted to the platform 112. FIGS. 4D-4F illustrate platforms 112D-112F respectively supporting the entry guide 108 with different proximal vertebrae 472D-472F.

In FIG. 4D, the platform 112D is formed of two parts, a back portion 112B that is coupled to the robotic arm 158 and a front portion 112A that couples to the back portion 112B. A plurality of fasteners 439 may be used to hold the front portion 112A and the back portion 112B coupled together. The front portion 112A may be detached from the back portion 112B so that the entry guide 108 may be readily mounted to and dismounted from the platform 112D within the opening 435. The proximal vertebrae 472D may include may include a lip 433 around its upper outer edge to support the entry guide 108. The proximal vertebrae 472D may include one or more engagement devices (e.g., tabs) 431 around its perimeter that may be fastened to the platform 112D by fasteners 432. The platform 112D may include threaded openings below the tabs 431 to receive a threaded bolt (fastener) 432.

In FIG. 4E, a bayonet type mounting may be used to couple the proximal end of the entry guide 108 to the platform 112E. The proximal vertebrae 472E may include one or more tabs 431 around its perimeter that when rotated may be fastened to the platform 112D by locking receptacles 433 around the opening 435. The platform 112E may be formed of one piece or two pieces and coupled to the robotic arm 158. The distal end of the entry guide 108 may be inserted first into the opening 435.

In FIG. 4F, a lock nut 436 may be used to couple the proximal end of the entry guide 108 to the platform 112E. The proximal vertebrae 472F may include a threaded exterior 437 around its perimeter that may be inserted up through opening 435 with the control cables, if any. One or more lock nuts 436 include an internal threaded opening 438 that may engage the threaded exterior 437 of the proximal vertebrae 472F to mount the entry guide to the platform 112F. The platform 112F may be formed of one piece or two pieces and coupled to the robotic arm 158. In an alternate embodiment, the lock nut 436 may instead be a clamping device that can open to release and close to engage and clamp around the vertebrae 372F to mount the entry guide 108 to the platform 112F.

To reduce the diameter of the entry guide the number of cables used to shape the entry guide during insertion into a patient may be reduced in number or eliminated entirely. Instead, the lumens may be used by devices to shape or assist in shaping the entry guide as it is inserted through an opening or orifice of a body or patient to a surgical site. After the entry guide is locked in position, flexible steering devices may be removed from the instrument lumens. The one or more open lumens may then be used to guide one or more robotic surgical tools through the opening in the body to the surgical site to perform the surgery. In one embodiment of the invention, the instrument lumens may also be used to make the entry guide rigid or stiff so as to lock its position within the body so that a surgery may be performed in a surgical site. After surgery is completed, a lumen may also be used to assist in the release of the rigidity or stiffness in the entry guide so that it may be removed from the patient through the opening from which is was inserted.

In an alternate embodiment of the invention, the entry guide itself includes a locking mechanism so that one or more cables may be used to make the entry guide rigid or stiff.

Instrument Guidance of the Entry Guide Tube

In one embodiment of the invention, the robotic surgical tools or instruments 101 themselves may be inserted into the lumens of the entry guide 108 and used to steer the entry guide around body tissue obstructions and towards a surgical site.

Referring now to FIGS. 5A-5C, a schematic view of a minimally invasive surgical instrument assembly 500 is illustrated. The surgical instrument assembly 500 illustrates that two or more surgical instruments that may run longitudinally through entry guide 504 in individual channels or lumens 506A, 506B, respectively from a proximal end to at or near a distal end thereof. The surgical instruments 502A, 502B may be, for example, snap-fitted into non-rotating sockets within the lumens 506A, 506B to maintain position within the entry guide 504. Other types of retention, locking, or attachment means, such as inflatable bladders (e.g., inflatable balloon or inflatable cylinder) around the perimeter of a distal section of the instrument, or deployment of mechanically expandable cams, collars or spring latches, may alternatively be employed to secure the distal portion of the instrument at one or more specific locations within the lumen of the entry guide. An inflatable bladder expands between the wall of the lumen and the outside surface of the surgical tool. The entry guide 504 may have other channels (not shown) through which, e.g., irrigation or suction may be provided to a surgical site, in addition to channels associated with active control mechanisms (e.g., cables for steering or locking).

End effectors 508A, 508B may each be coupled to the distal ends of instruments 502A, 502B respectively. The surgical instruments 502A, 502B represent at least two of the robotic surgical tools 101. The end effectors 508A-508B may or may not be gripping tools to help assist in steering or guiding the entry guide to a surgical site. The end effectors 508A-508B may be sharp surgical tools, such as scissors for example. The surgical instruments 502A-502B may be coupled to the lumen walls in the lumens 506A-506B by the retention, locking, or attachment means such that the instrument tips of the end effectors are safely inside the entry guide and cannot harm tissue when the entry guide is being steered to the surgical site by pushing and/or pulling on the instruments 502A-502B.

Instrument assembly 500's cross section may be circular, elliptical, or other shape (e.g., rounded rectangle or other polygon). Various combinations of surgical instruments 502A, 502B and entry guide 504 may be rigid, passively flexible, and actively flexible, as well as lockable, and each instrument or entry guide may be composed along its length of multiple different constructions.

The entry guide 504 may include an optional imaging system 511 (e.g., one or more image capture chips with associated optics and electronics) positioned at its distal end. The imaging system 511 has a field of view that may be used to assist advancing guide tube 504 and that allows a surgeon to view end effectors 508A, 508B working at a surgical site. Imaging system 511 may be coupled to an articulatable structure attached to the entry guide 504 to provide independent motion of the imaging system in one or more degrees of freedom. Alternately, the imaging system may itself be coupled to the end of an instrument assembly which may be inserted through one of the lumens in the entry guide to provide imaging at the distal end. Such an imaging instrument assembly may also be used to provide a steering or locking function.

The instrument assembly 500 may be inserted into a patient via a cannula, a natural orifice, or an incision. In some instances, a cannula-type guide may be used to assist insertion via natural orifice. Cannula-type guides may be straight or curved to facilitate insertion (e.g., for entry into the esophagus via the mouth and throat).

Instrument assembly 500 may be initially inserted in a rigidized or locked state. The instrument assembly 500 may be flexible in an unlocked state and actively steered during insertion in order to reach a target surgical site.

In some embodiments, the instruments 502A, 502B may each be locked axially into the tip of the entry guide 504, or at another chosen location along the length of the lumens of the entry guide 504. The tip of the entry guide may then be steered by pushing on the proximal end of one instrument while simultaneously pulling on the proximal end of the other instrument.

FIGS. 5D and 5E are diagrammatic perspective views that illustrate aspects of a removable instrument 548 that is held in place within a lumen 540 of the entry guide 504. The distal end 542 of the entry guide 540 has an opening 544 though which the distal end of the instrument passes. The opening 544 is optionally made non-round to prevent the instrument from rolling within entry guide 540. An optional fitting 546 (e.g., a spring that snaps into a detent, etc.) holds the instrument's end effector 548 in position to keep the instrument from translating through the lumen and the entry guide. A round opening 544 allows the instrument to roll while fitting 546 keeps the instrument from translating. When the fitting 546 releases the instrument (e.g., when sufficient pulling force is applied), the instrument may be withdrawn from the entry guide. The roll prevention configuration and the fitting are illustratively shown at the distal end of the entry guide but may be placed at various positions (e.g., at the insertion end of the entry guide). The roll prevention configuration and the fitting can be used in the various aspects for other instrument and guide tube combinations.

Alternatively, the instruments 502A, 502B may be left to slide freely in the entry guide 504, but may be articulated individually or in concert to alter the shape of the entry guide at its proximal end or anywhere along its length. In some aspects, two or more instruments may be inserted each individually in different lumens to different depths within the entry guide to provide articulation of the entry guide along a significant portion of its length.

In some aspects, the instruments 502A, 502B and entry guide 504 may be alternatively coaxially advanced. Both instruments may be advanced and held in a fixed position while the entry guide is advanced over both instruments and locked in the position imposed by the instruments. By repetition of this process, the entry guide may be progressed in steps from the point of insertion to the surgical site. In another aspect, a first instrument is advanced and held or locked, the entry guide is advanced over the first instrument, and then the second instrument is advanced and held or locked so the that entry guide can be advanced over it. For example, instrument 502A may be actively steered (only the distal section of the instrument (or guide tube) need be actively steerable) part way along the trajectory to the surgical site and then locked. The more proximal sections of the instrument may be passive or may use curve propagation as the instrument (or guide tube) advances. Curve propagation is disclosed in, e.g., Ikuta, K. et al., "Shape memory alloy servo actuator system with electric resistance feedback and application for active endoscope," 1988 IEEE International Conference on Robotics and Automation, Apr. 24-29, 1988, Vol. 1, pages 427-430, which is incorporated by reference. The entry guide 504 may then be passively advanced to the distal end of instrument 502A and locked to support further advancement of instruments. The coaxial alternating advancing and locking continues until the surgical site is reached along the desired trajectory.

Alternatively, the whole body or just the distal section of entry guide 504 is actively steerable and lockable, and instruments 502A, 502B are passively advanced inside the entry guide until the surgical site is reached. If both the surgical instruments 502A, 502B and the entry guide 504 are actively steerable, then they may "leapfrog" each other as they coaxially advance and lock along the trajectory to the surgical site. Such coaxial insertion may also be used with any combination of one or more instruments and a guide tube.

Referring now to FIGS. 5F-5H, a plurality of robotic surgical tools 502A-502B may be used to influence the behavior of an entry guide 504. The shape and behavior of the entry guide 504 may be influenced by the insertion of at least two instruments inserted into two lumens with their distal ends adjacent to the distal end of the entry guide and fixed or locked in place. That is, the distal ends of the instruments (end effectors 508A-508B) are aligned with the distal end of the entry guide 504 and locked there together. With the at least two tools 502A-502B opposed (e.g., left lumens and right lumens) to one another in lumens radially spaced apart equally, they can actuate the entry guide.

Steering the entry guide 504 with a plurality of robotic surgical tools is advantageous because it uses the same actuation mechanism as the instrument, and minimizes required instrument changes. The entry guide 504 can be loaded up with the required robotic surgical instruments or tools, installed and steered to surgical site, and the used to efficiently operate on tissue in the surgical site without instrument changes or minimizing the time consuming instrument changes.

In FIGS. 5F-5H, the distal ends or other part of the tools 502A-502B may be locked within lumens of the entry guide 504 by a retention, locking, or attachment device, such as described with reference to FIGS. 5D-5E. When locked within the lumens to the entry guide 504, the shafts or instrument bodies of the instruments may be used liked cables. In one aspect of the invention, the pair of tools 502A-502B may have their shafts alternatively pushed and pulled or conjunctively pushed or pulled to shape the entry guide as illustrated by the arrowheads 517A-517F.

During surgery, the locking device may rotationally lock an instrument to the entry guide within a lumens to prevent tensional wind-up of a long flexible instrument shaft in response to a torque on the instrument tips. If the shaft of the tool is not locked within the lumens during surgery, the instrument may roll near the distal end of the entry guide when attempting to manipulate tissue by movement of the instrument tips in an X or Y direction. Without locking a shaft of the tool to the entry guide within the lumens, the tip may remain stationary while the shaft twists inside lumen of the entry guide.

In FIG. 5F, the tools 502A-502B are pushed with the same force together as illustrated by arrowheads 517A-517B to steer the distal end of the entry guide straight further into a body cavity.

In FIG. 5G, to steer the entry guide to the right, tool 502A may be pushed along its insertion axis as indicated by arrow 517C and tool 502B may be pulled along its insertion axis as indicated by arrow 517D.

In FIG. 5H, to steer the entry guide to the left, tool 502A may be pulled along its insertion axis as indicated by arrow 517E and tool 502B may be pushed along its insertion axis as indicated by arrow 517F.

In another aspect of the invention, the tools 502A-502B may be individually shaped with their own control cables to impart a similar shape to the entry guide 504. As shown in FIG. 5I, each tool 502A-502B may have a steerable tip portion 522A-522B coupled to a passive body portion 523A-523B that may be locked to hold its shape. Moreover, the tools 502A-502B may be used in series and independently steered or bent to actuate the entry guide 504 without being locked thereto.

In FIG. 5I, the cables 515A-515B and 516A-516B respectively control the orientation of the steerable tip portions 522A-522B of the shafts of the tools 502A-502B. With the cables held in a steady state with the tool shafts being steered straight, the distal end of the entry guide 504 may be steered straight as it is inserted into a body cavity. Additionally, the tools 502A-502B may be staggered in series along a path to a surgical site with the entry guide 504 being pushed over their shapes. The tools 502A-502B may slide within the respective lumens 506A-506B and leap-frog in front of each other in series towards the surgical site with the entry guide 504 being pushed over each. For example, tool 502B may have its passive body portion 523B rigidly locked and its steerable tip portion held in steady state by its cables 516A-516B so that the tool 502A and the entry guide 504 may advance forward and take on the shape of tool 502B.

In FIG. 5J, some cables 515D, 516C are paid out while other cables 515C, 516D are pulled in to steer the steerable tip portions 522A-522B of the shafts of the respective tools 502A-502B in opposite directions to steer the entry guide 504 through a pair to turns forming an S shape.

In FIG. 5K, some cables 515E, 516E are pulled in while other cables 515F, 516F are paid out to steer the steerable tip portions 522A-522B of the shafts of the respective tools 502A-502B in the same direction so that the entry guide 504 may follow along in the same direction.

While FIGS. 5I-5K illustrate an independent serial progression of tools 502A-502B within the lumens to shape the entry guide, the tools may alternatively be extended and in front of the entry guide and operated in parallel together out of the lumens to steer and shape it towards a surgical site.

FIGS. 5I-5K illustrate robotic surgical tools 502A-502B being progressively used to steer and shape an entry guide. FIGS. 5D-5E illustrate a retention, locking or attachment mechanism to couple a portion of a tool to a lumen wall of the entry guide. However, specialized steering instruments may be used instead to progressively lock and steer the entry guide to influence its shape. Similar to tools 508A-508B illustrated in FIGS. 5F-5H, the specialized steering tools may lock in attachment to the lumen wall near the distal portion of the entry guide and steer it by pushing and/or pulling on the shafts of the specialized steering instruments. The steering instruments are removed from the lumens and replaced with surgical instruments after the entry guide has reached the surgical site. Similar to tool 508B illustrated in FIGS. 5I-5K, the specialized steering instruments need not be inserted fully into the lumens of the entry guide to steer and control intermediate portions of the entry guide. The steering instruments may be locked to the lumen wall at intermediate positions between the proximal and distal ends of the entry guide. The lumen walls of the entry guide may have internal ridges along its length so that the steering instruments (or surgical instruments) can attach to the lumen wall at particular depths when inserted.

The shaft of these steering instruments may have a smaller diameter than a surgical instrument but for a lumen locking mechanism. The shaft of these steering instruments may be as simple as a cable with a collar or expandable pins at a distal end to lock to the lumen wall at various positions along its length. As the shaft of the steering instruments may be smaller in diameter, a plurality of steering/shaping instruments may be inserted into the same lumen of an entry guide. Each of the plurality of steering instruments in the same lumen may be inserted to different depths and attach to different sections of the entry guide. In this manner, the entry guide has a complex but removable cable control system along its length that can steer more than one portion of the entry guide.

With more than one steering instrument is a single lumen, the instrument cross section is much smaller than the lumen and may not support compression without buckling. Thus, the shafts of the steering instruments in this case are under tension. In order to steer the entry guide, instruments at same depth are placed in other lumens. The retention, locking, or attachment mechanism is designed to avoid filling the entire cross-section of the lumen so that more distal instruments can pass by it in the same lumen. The retention, locking, or attachment may consist of a pair of opposing extendable pins to engage the internal ridges in the lumen wall of a lumen.

Referring now to FIGS. 9A-9F, an entry guide system 900 is illustrated including a plurality of robotic surgical tools 902A-902B and an entry guide 504. The plurality of robotic surgical tools 902A-902B are operated in parallel together to steer and shape the entry guide 504 towards a surgical site. Steerable tip portions 522A-522B of the respective robotic surgical tools 902A-902B are flexible (see shaft 106 of tool 101 illustrated in FIG. 3A), extend out of the lumens 506A-506B in front of the entry guide 504, and may be steered in unison. To further steer and shape the entry guide 504, the proximal ends of the tools 902A-902B may also be alternatively or conjunctively pushed and pulled so as to maximize the forces applied to the distal end of the entry guide 504. The proximal ends of the steerable tip portions 522A-522B are locked or attached to the lumen walls near the distal end of the entry guide 504.

The plurality of robotic surgical tools 902A-902B may each include an end effector 932A-932B. The end effectors 932A-932B may or may not be gripping tools to help assist in steering or guiding the entry guide to a surgical site. Instead, the end effectors 932A-932B may be sharp tools for surgical procedures, such as scissors for example. One or more soft nosecones may be provided, such as on a camera tool, so that the sharp instrument ends of the end effectors 932A-932B can tuck into the one or more nosecones and avoid injuring tissue as the steerable tip portions 522A-522B are steered in front of the distal end of the entry guide. With the plurality of instruments 902A-902B being steerable devices for the entry guide, the entry guide system 900 is analogous to an endoscope with a steerable tip and a pushable body, However, the entry guide may be made rigid (lockable) by various locking devices.

The entry guide 504 may be a passive entry guide with minimal or no means to steer or influence its shape. However, the entry guide 504 may be lockable with locking cables or other locking means described herein. Because the entry guide 504 may be a passive entry guide without its own means to steer, a substantial portion of the cross section of the flexible entry guide may be made available for instrument lumens, allowing for a substantial increase in performance of the tools 902A-902B with respect to an active entry guide with its own steering capability.

The robotic surgical tools 902A-902B may respectively include sensors 930A-930B adapted to allow the robotic control system to determine the respective three dimensional tool shape in space. Various known shape sensing systems may be used. As one non-limiting example, information from encoders coupled to actuating motors that steer the tool (e.g., with steering cables that extend to various positions on the flexible tool) may be used to determine the tool shape in three dimensional space. As another non-limiting example, three dimensional tool shape information may be obtained from one or more fiber optic shape sensors extending the length of the instrument or tool (one such fiber optic shape sensing system is available from Luna Innovations Corporation, Roanoke, Va.). Fiber optic shape sensors are further described in U.S. patent application Ser. No. 11/491,384, entitled ROBOTIC SURGERY SYSTEM INCLUDING POSITION SENSORS USING FIBER BRAGG GRATINGS, filed on Jul. 20, 2006 by inventors David Q. Larkin, et al (U.S. Pat. App. Publ. No. US 2007/0156019 A1), which is incorporated herein by reference. Various other shape sensing systems include sensors (e.g., to sense space between links in the tool, to sense triangulation information from external transmitters, etc.) placed along the tool. Shape information may be used to control the tool's shape.

A computer, such as computer 151 in the surgeon's console 150 illustrated in FIG. 1C, may include a tool control and tracking software system 184 responsive to the sensors 930A-930B. The tool control system 184 is capable of controlling the steerable tip portions 522A-522B so that each has substantially the same shape as the others as they are articulated towards a surgical site.

Figure 9A:
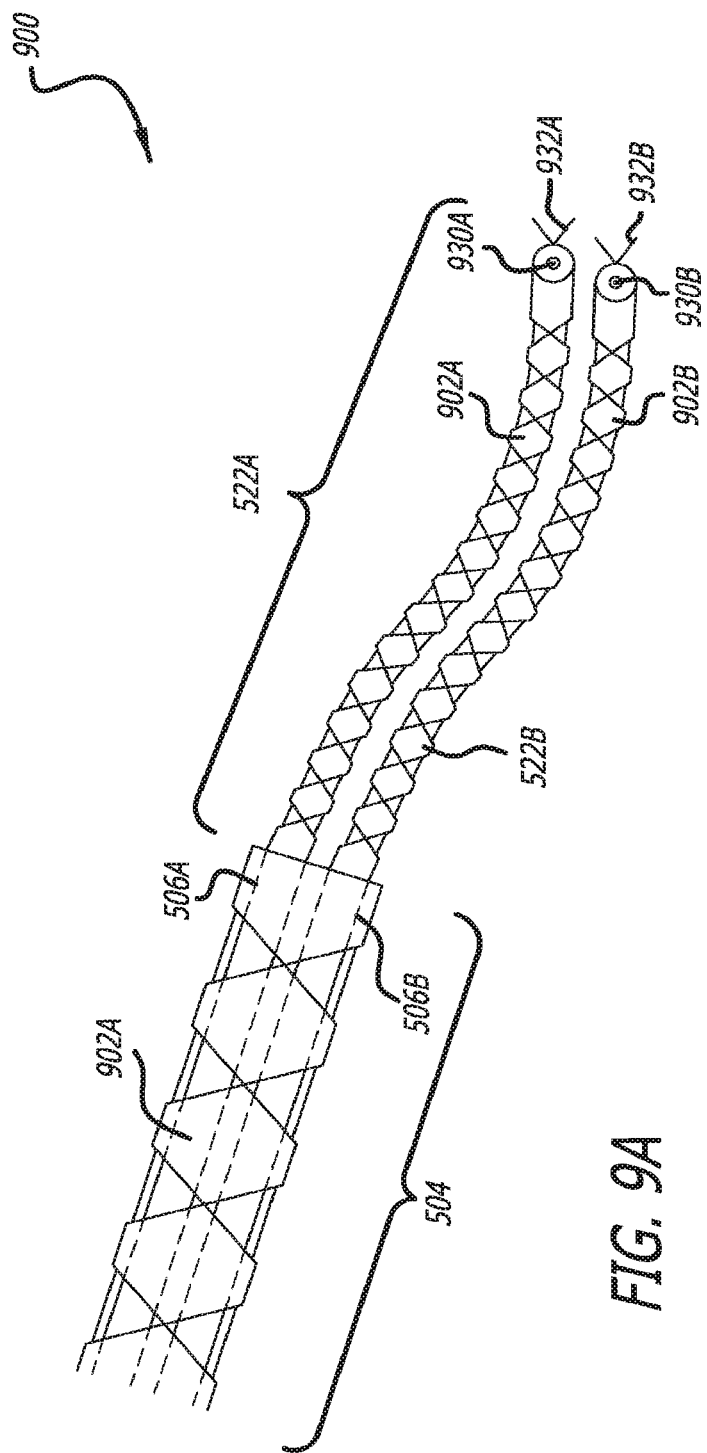
Figure 9B:
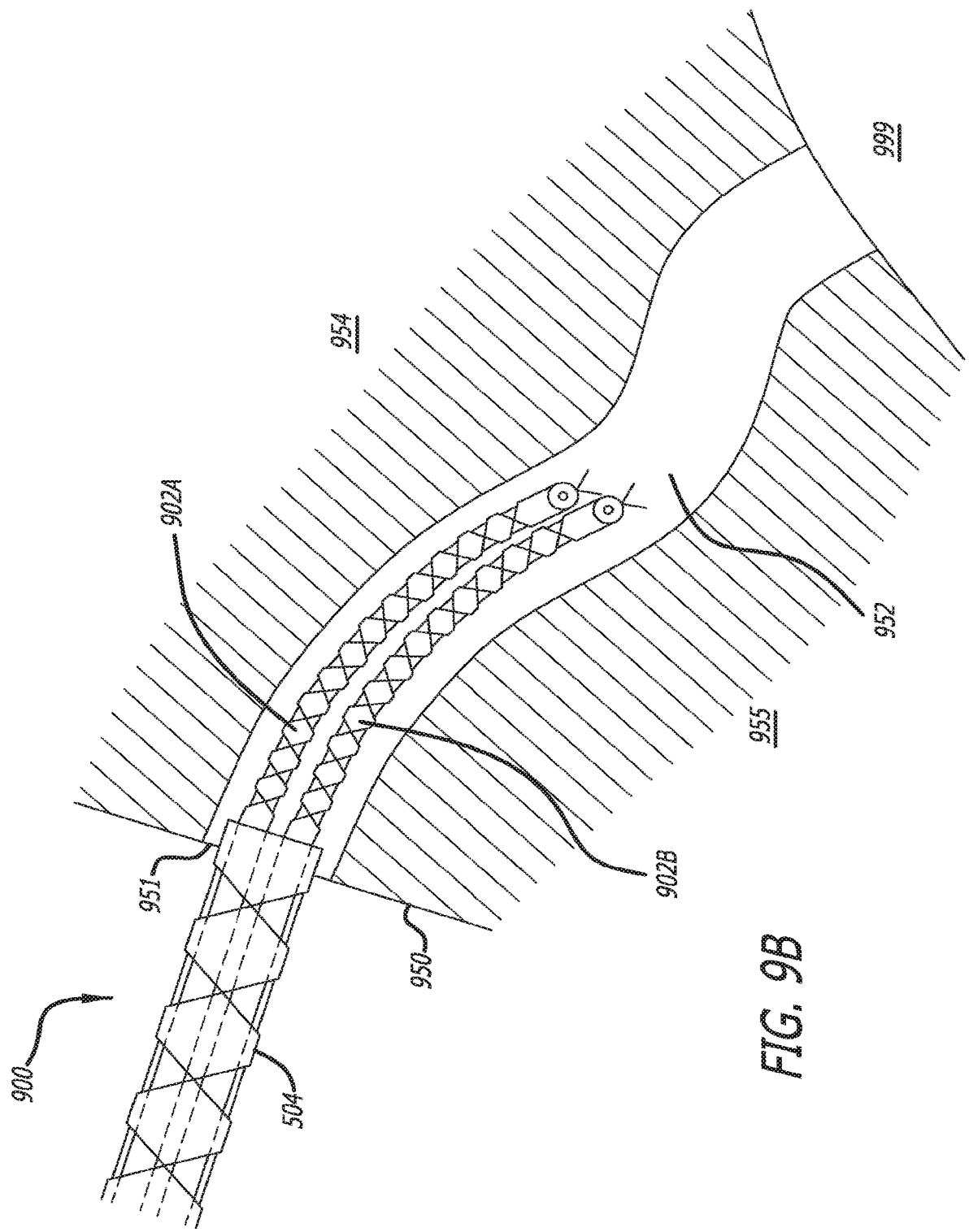

In FIG. 9B, the entry guide system 900 is inserted through an opening 950 into a body 950 and extended towards a surgical site 999. The robotic surgical tools or instruments 902A-902B with their respective steerable tip portions 522A-522B of their shafts are steered substantially as a group to follow a path 952 between tissue 954-955 to the surgical site 999. As the robotic surgical tools 902A-902B are not locked into the entry guide 504, they may extend further in length out of the lumens, beyond a surgical working length that may be used during surgery. The entry guide 504 follows along in the path 952 behind the robotic surgical tool tip portions 522A-522B.

Figure 9C:
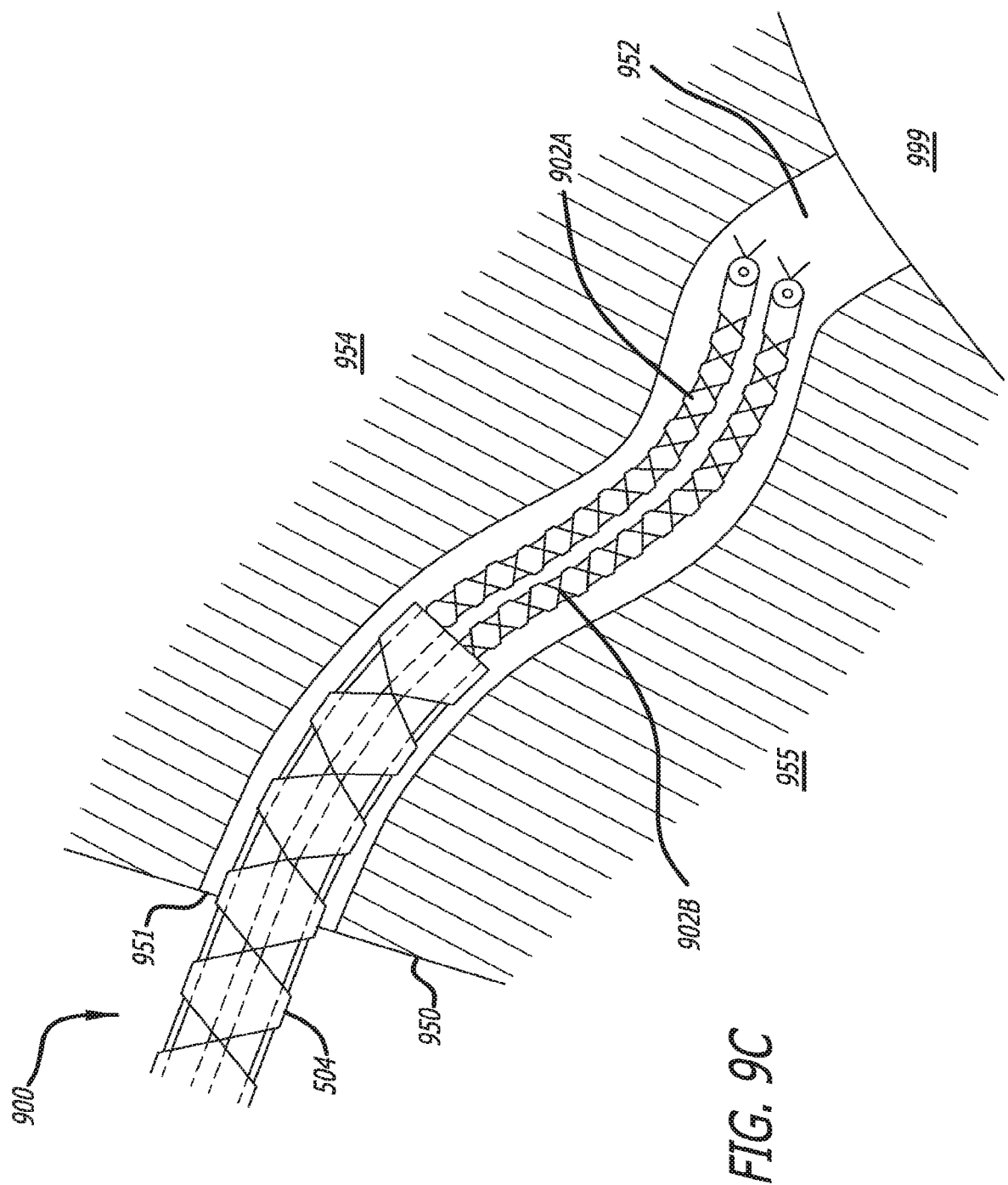

In FIG. 9C, the entry guide system 900 may generally be pushed and guided further along the path 952 under remote control of the surgeon's console. The steerable tip portions 522A-522B of the robotic surgical tools 902A-902B may be steered and shaped by actuators under remote instrument control of the surgeon's console. The entry guide 504 may be pushed and steered along the path 952 by actuators under remote entry guide control of the surgeon's console. The entry guide 504 is flexible but sufficiently stiff to receive a pushing force outside of the patient's body 950 so that it may follow the shape of the path 952 made by the robotic surgical tool tip portions 522A-522B.

Figure 9D:
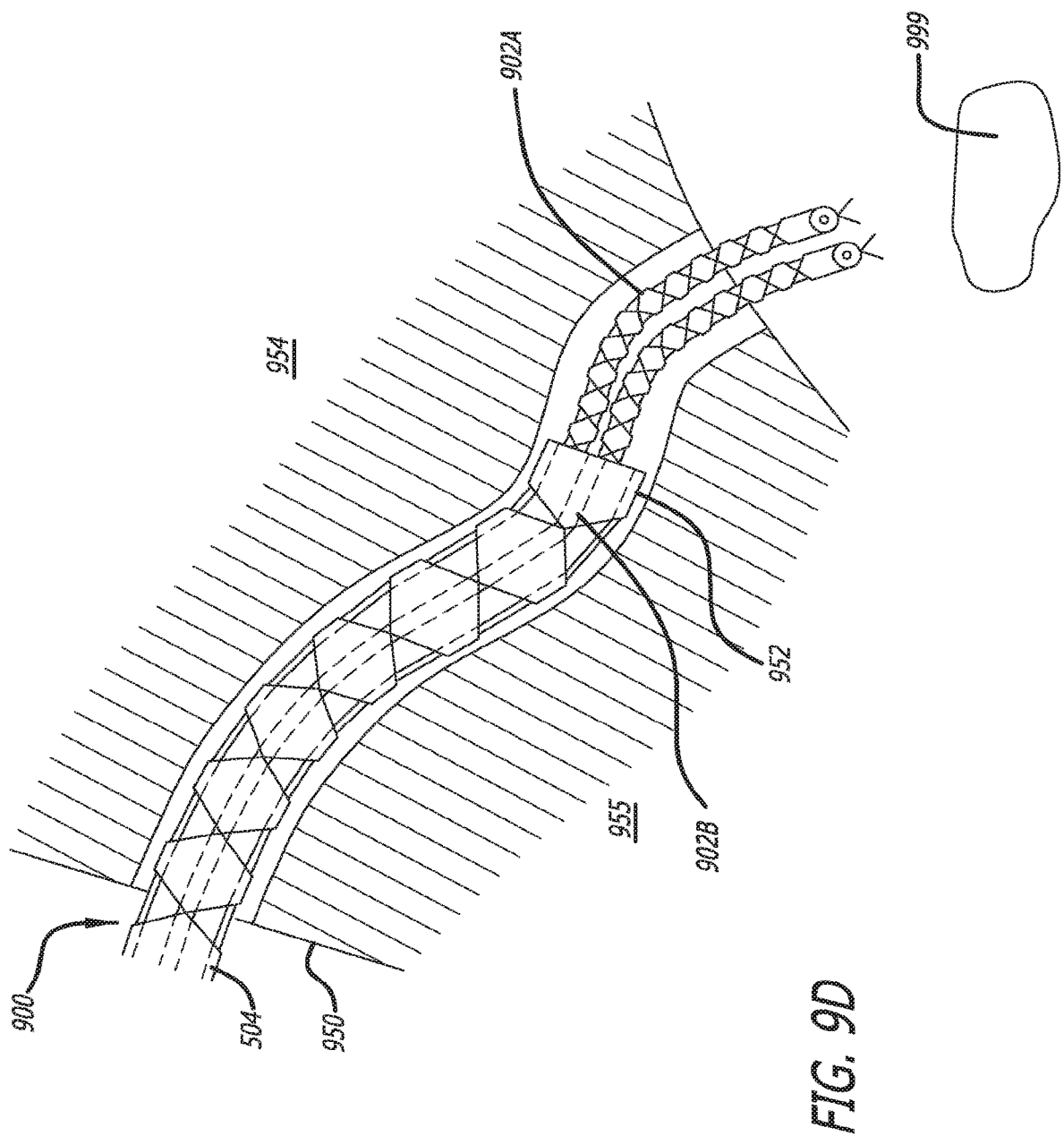

In FIG. 9D, the entry guide system 900 is further inserted into the body along the curved path 952 with the robotic surgical tools 902A-902B reaching towards the surgical site 999.

Figure 9E:
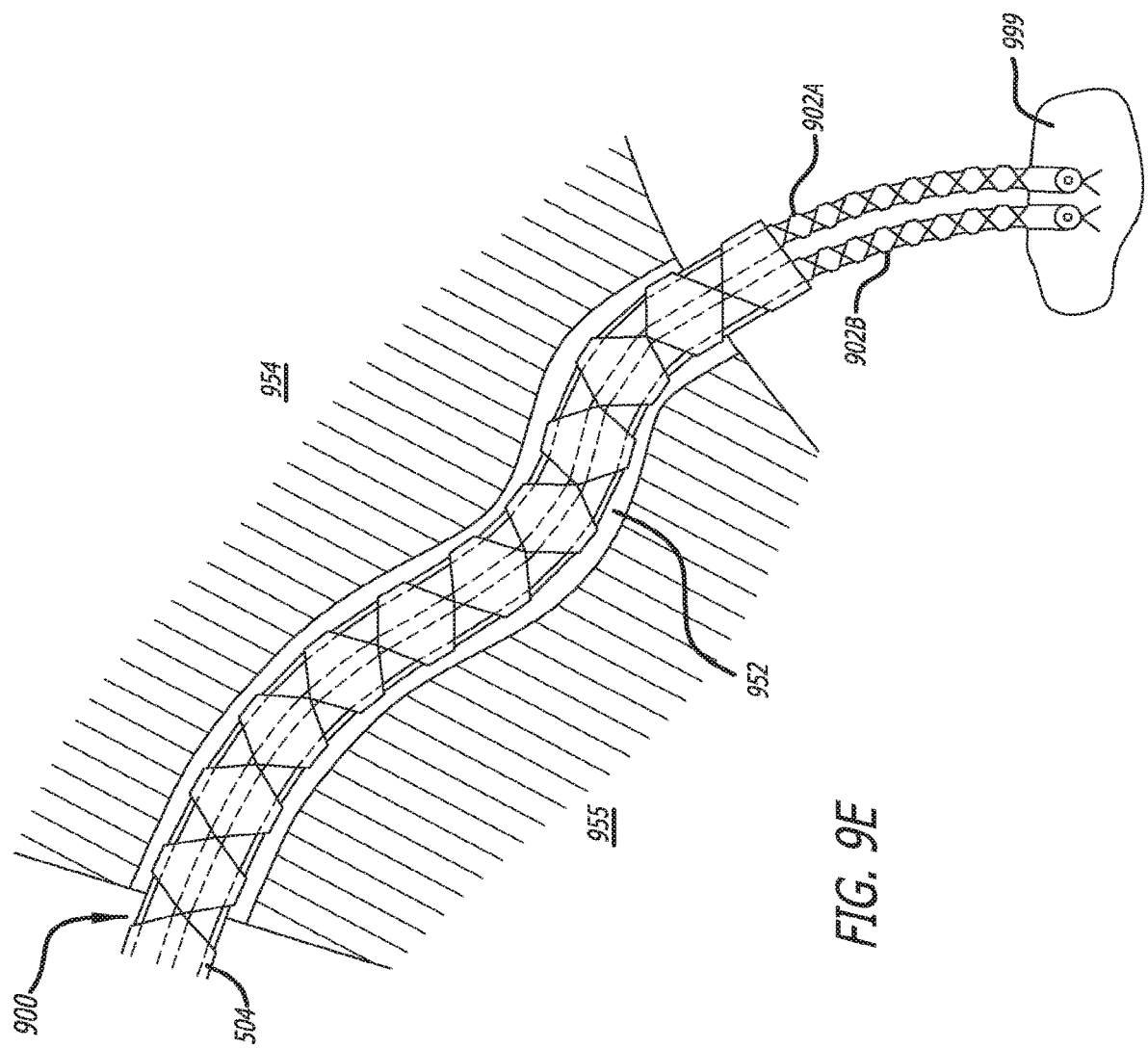

In FIG. 9E, the distal ends of the robotic surgical tools 902A-902B of the entry guide system 900 have reached the surgical site together. However, the entry guide system 900 may be further inserted into the body along the curved path 952 prior to performing surgery.

Figure 9F:
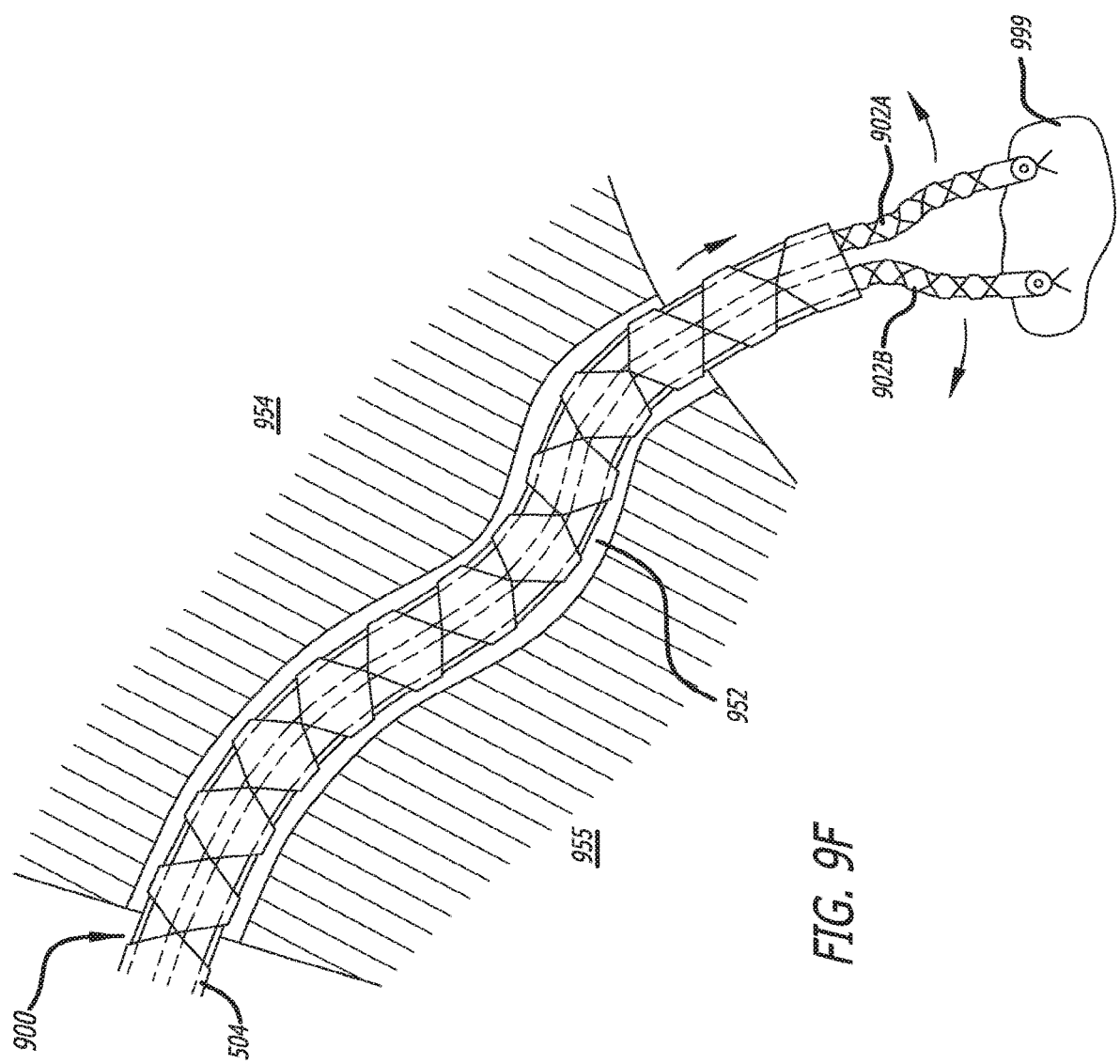

In FIG. 9F, the entry guide system 900 may be further inserted into the body along the curved path 952. The entry guide 504 may be advanced over the robotic surgical tools 902A-902B to provide support for them closer to the surgical site 999. The entry guide 504 or portions thereof near the surgical site 999 may then be locked substantially in place to resist movement so as to support the robotic surgical tools 902A-902B during surgery. Upon reaching the surgical site 999, the robotic surgical tools 902A-902B may be deployed, spreading out away from their positions used during insertion to guide the entry guide 504 down the path 952. The deployment of the robotic surgical tools 902A-

902B provides a working separation to perform a surgical procedure at the surgical site 999.

Described previously with reference to FIGS. 9A-9F, a plurality of robotic surgical tools 502A-502B extending out from the lumens of an entry guide 504 were operated in parallel together to guide it along a path to a surgical site. Alternatively, a plurality of robotic surgical tools extending from the lumens may be operated in a serial fashion with alternating advancement to guide a locking entry guide along a path to a surgical site.

Referring now to FIGS. 7A-7C, a schematic diagram of an entry guide system is illustrated including an entry guide 108 and a plurality of robotically controlled steering tools 700A-700C. The shafts 701A-701C of the respective plurality of robotically controlled steering tools 700A-700C may be used to shape and influence the behavior of the entry guide 108 as it is inserted into the patient P's body. The shafts 701A-701C of the respective plurality of robotically controlled steering tools 700A-700C are significantly longer than the length of the entry guide 108 so that they may extend out beyond the distal end of the entry guide. The entry guide 108 may slide over the shafts 701A-701C of the respective plurality of robotically controlled steering tools 700A-700C and follow their shape along a path to a surgical site. The distal end of one or more shafts 701A-701C may respectively include a camera 704A-704C to capture images to steer the steerable end portions of the shaft within the body towards a surgical site.

In FIG. 7A, prior to initial insertion of the entry guide 108 into the body, the steering tools 700A-700C with their extended shafts may be first inserted first. With the lumens 405A-405C over the shafts 701A-701C respectively, the entry guide 108 may then be slid over the shafts towards the surgical site to follow their shapes for guidance to the surgical site. The first steering tool 700A has its shaft 701A initially extended out farthest away from the distal end of the entry guide 108.

In FIG. 7B, the entry guide 108 has been inserted into the body over the shafts 701A-701C. The steering tool 700C is made flexible and can be steered out further from the distal end of the entry guide 108 towards the surgical site. The steering tool 700C may be advanced further along the path than the other tools 700A-700B in a serial fashion. The entry guide 108 may then be inserted further into the body over the shafts 701A-701C of the tools 700A-700C towards the surgical site.

In FIG. 7C, the entry guide 108 has been inserted still further into the body over the shafts 701A-701C with its distal end located near the surgical site. Note that the distal end of the entry guide 108 may extend out over the distal ends of one or more of the shafts 701A-701B.

After positioning the distal end of the entry guide 108 with the steering tools, it may be rigidized to keep its shape so that all the steering tools 700A-700C may be removed to allow robotic surgical tools to be inserted into the lumens 405A-405C.

In an alternative embodiment of the invention, a single non-locking camera/grasping instrument may be used to navigate an entry guide system to a surgical site. The single non-locking camera/grasping instrument can be steered and capture images to provide vision while it is inserted. The single non-locking camera/grasping tool can grasp tissue to anchor its distal portion. The entry guide may then be slide over the tool following its shape and path to the surgical site. The entry guide may then be rigidified so that other instruments may be inserted into other available lumens. The non-locking camera/grasping tool may maintain its grasp on tissue to hold it anchored during surgery and use its camera to provide images of the surgical site.

Robotically Controlled Steering Tool for Entry Guide Shaping

A single special tool, a robotically controlled steering tool, such as the tool 101 illustrated in FIGS. 3A-3C but without an end effector 348 may be used to influence the shape and behavior of the entry guide 108. Any cables that might have been used to actuate an end effector are instead used to steer the shaft. The tool 101 includes the flexible/steerable/lockable shaft 106 that is inserted into an instrument lumen of the entry guide 108. The flexible/steerable/lockable shaft 106 is a cable-articulated snake mechanism controlled by one or more actuators. The flexible/steerable/lockable shaft 106 may be formed with the vertebrae 372-376 shown in FIG. 3C.

Greater actuating (steering) forces may be applied by a robotically controlled steering tool to shape and influence the behavior of the entry guide, or alternatively reduce the cross-sectional dimensions of the entry guide by eliminating some or all of the steering control cables of the entry guide 108 while providing similar actuating (steering) forces.

Pre-Curved Stiffening Rods for Entry Guide Shaping

Another means of influencing the behavior and shape of the entry guide 108 is by insertion of a preformed device into one or more of the instrument lumens of the entry guide. Such a device may be a pre-curved stiffening rod or tube that is inserted into the instrument lumens to shape and influence the behavior (e.g., increase stiffness or alter shape) in all or portions of the entry guide. Such a pre-curved stiffening rod or tube may additionally have a varying cross-section along its length to alter its bending stiffness as needed to provide the desired bend profile. Moreover, the end position of a stiffening rod may be moveable to change its behavior during insertion. For example, a short stiff tip with a small bend radius and limited total bend angle may be used to navigate down a lumen. Altering the end position, a longer, more flexible tip with a large total bend angle may be formed in the stiffening rod for traversing open space.

Referring now to FIGS. 8A-8F, schematic diagrams of an entry guide system is illustrated including an entry guide 108 coupled to the platform 112 and a plurality of pre-curved stiffening rods 800A-800N. In this system, the plurality of pre-curved stiffening rods 800A-800N may be used to shape and influence the behavior (e.g., increase stiffness or alter shape) in all or portions of the entry guide 108. The pre-curved stiffening rods 800A-800N have a stiffness that is tailored so that its stiffness level is low enough to allow it to be forced to take the shape of the entry guide when inserted, but high enough so that a significant portion of the force available in the entry guide actuation means is needed to overcome the shape of the pre-curved stiffening rod. The difference between these two forces is the amount of force available to bias the shape of the entry guide in the direction of the inserted stiffening rod. Alternatively, an actuation force to overcome the stiffness of the stiffening rods may be derived from an external support such as an overtube to keep the entry guide 108 in its desired position.

The stiffening rods 800A-800N include a curved portion 801A-801N, respectively, that may differ from each. The curved portion 801A-801N of the stiffening rods 800A-800N may be non-circular so that they do not twist inside the lumens 405A, 405B', 405C (generally referred to as lumens 405) of the entry guide 108. The stiffening rods 800A-800N may allow for the application of additional actuation force in a pre-determined direction to the section of the entry guide 108 that is occupied by the curved portion 801A-801N of the stiffening rods.

The length of the stiffening rods 800A-800N may be longer than the length of the entry guide 108 so that they can extend out from the proximal end of the entry guide and can be inserted to a chosen depth relative to specific anatomic features. With a stiffening rod 800A-800N inserted into a lumen, the entry guide may be further inserted using the curved portion 801A-801N of the stiffening rod as a guide. The stiffening rods 800A-800N may be interchanged to obtain different bend angles to help bend the entry guide, such as through the throat of a patient during trans-oral insertion, or traversing the peritoneum during procedures requiring significant retroflex ion of the entry guide, such as trans-gastric cholysystectomy. To determine where to position stiffening rods, the entry guide 108 may have a camera 820 at its distal end to view how it should be steered with the stiffening rods as it is inserted into the body cavity.

Figure 8A:
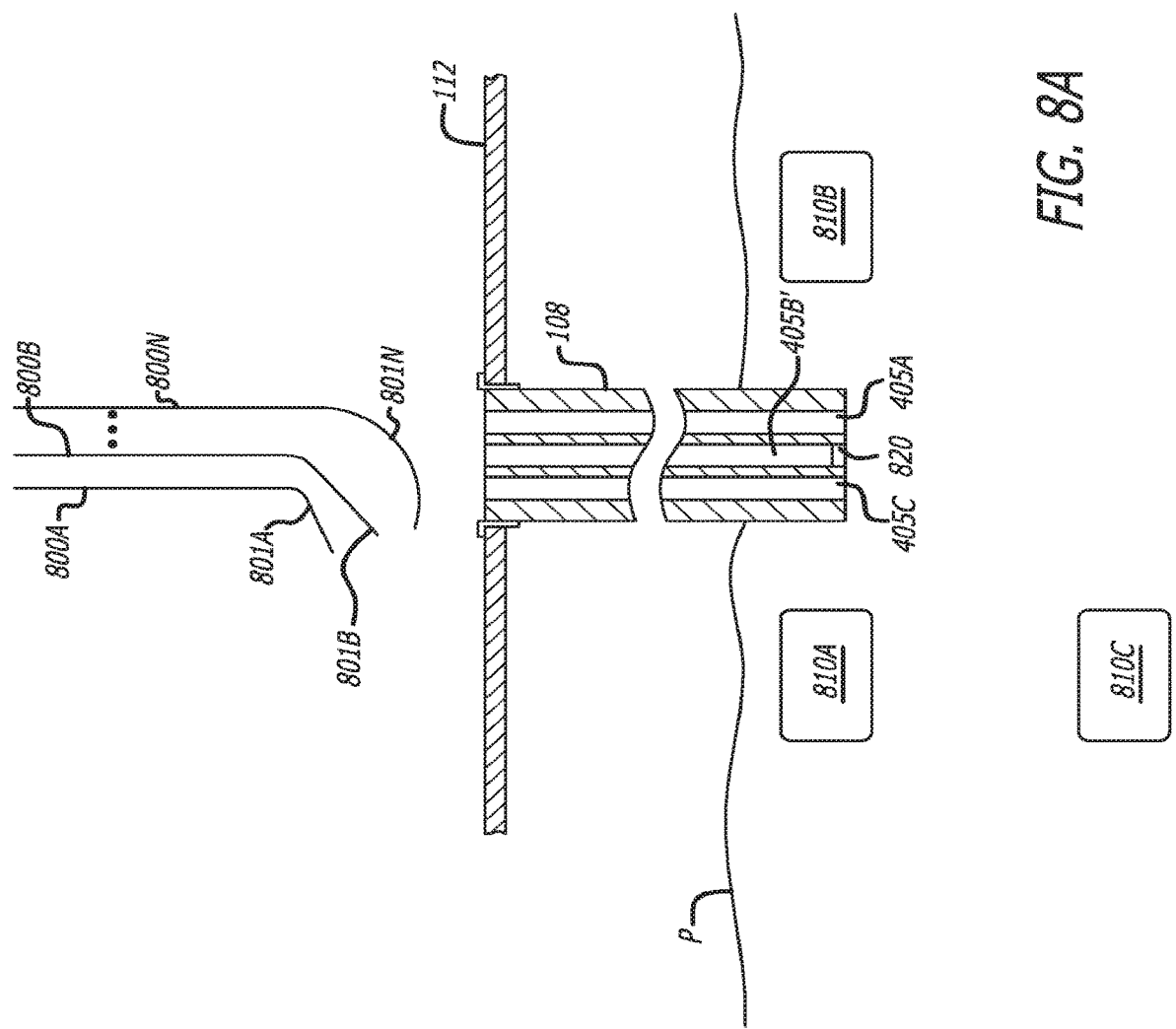

In FIG. 8A, the stiffening rods 800A-800N have yet to be inserted into a lumen 405A-405C of the entry guide 108 to assist in steering and/or shaping it. Alternatively, a stiffening rod 800A-800N may be inserted into each of the lumens 405A, 405B', 405C prior to the initial insertion of the entry guide 108 into a patient. The initial insertion of the entry guide 108 was straight ahead between obstructions 810A-810B with little bending. The proximal end of the entry guide 108 may be lowered by the platform 112 so as to insert the distal end of the entry guide into the patient's body P.

Figure 8B:
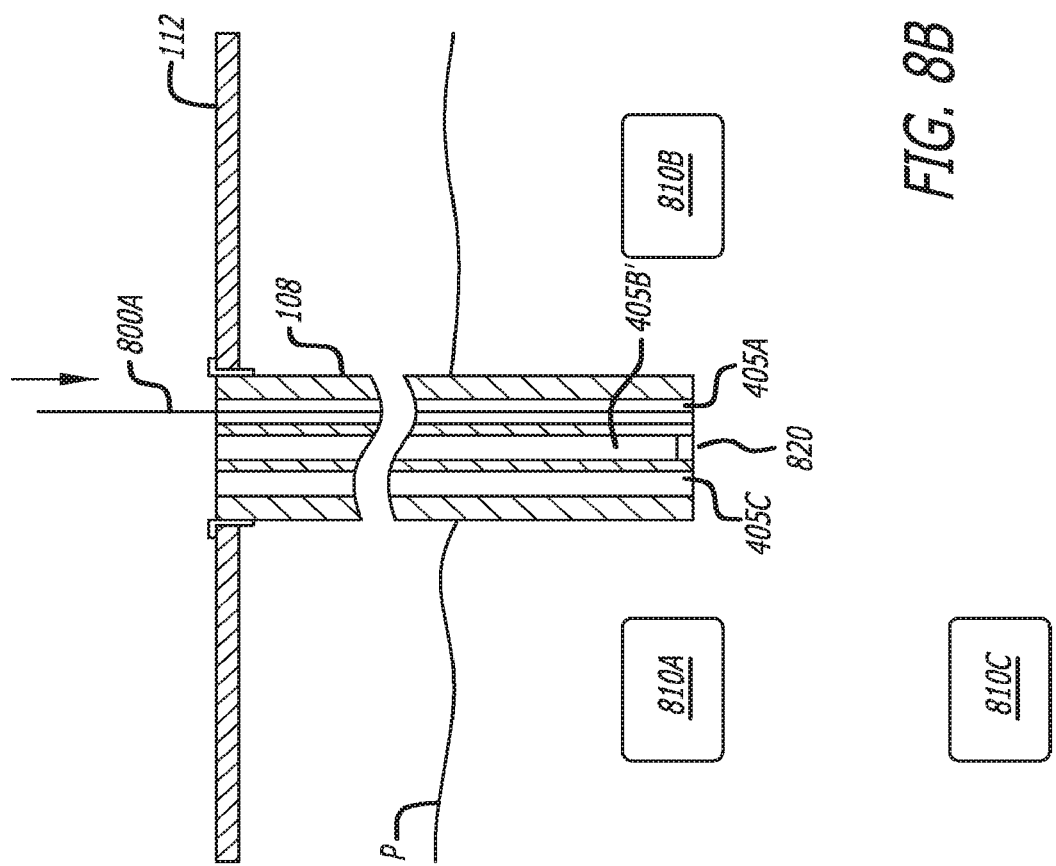

In FIG. 8B, a first pre-curved stiffening rod 800A is inserted into a first instrument lumen 405A to assist in steering and/or shaping the entry guide 108 between the obstructions 810A and 810C of the body cavity. The curved portion 801A of the stiffening rod 800A initially conforms to the shape of the entry guide 108.

In FIG. 8C, a second pre-curved stiffening rod 800B is inserted into a second instrument lumen 405C to assist in steering and/or shaping the entry guide 108 between the obstructions 810A and 810C of the body cavity. With the added actuation force of the second stiffening rod 800B, the curved portions 801A-801B of the stiffening rods 800A-800B may turn a portion of the entry guide 108 to steer the distal end between the obstructions 810A-801B. The entry guide 108 may be further inserted into the body cavity.

Figure 8D:
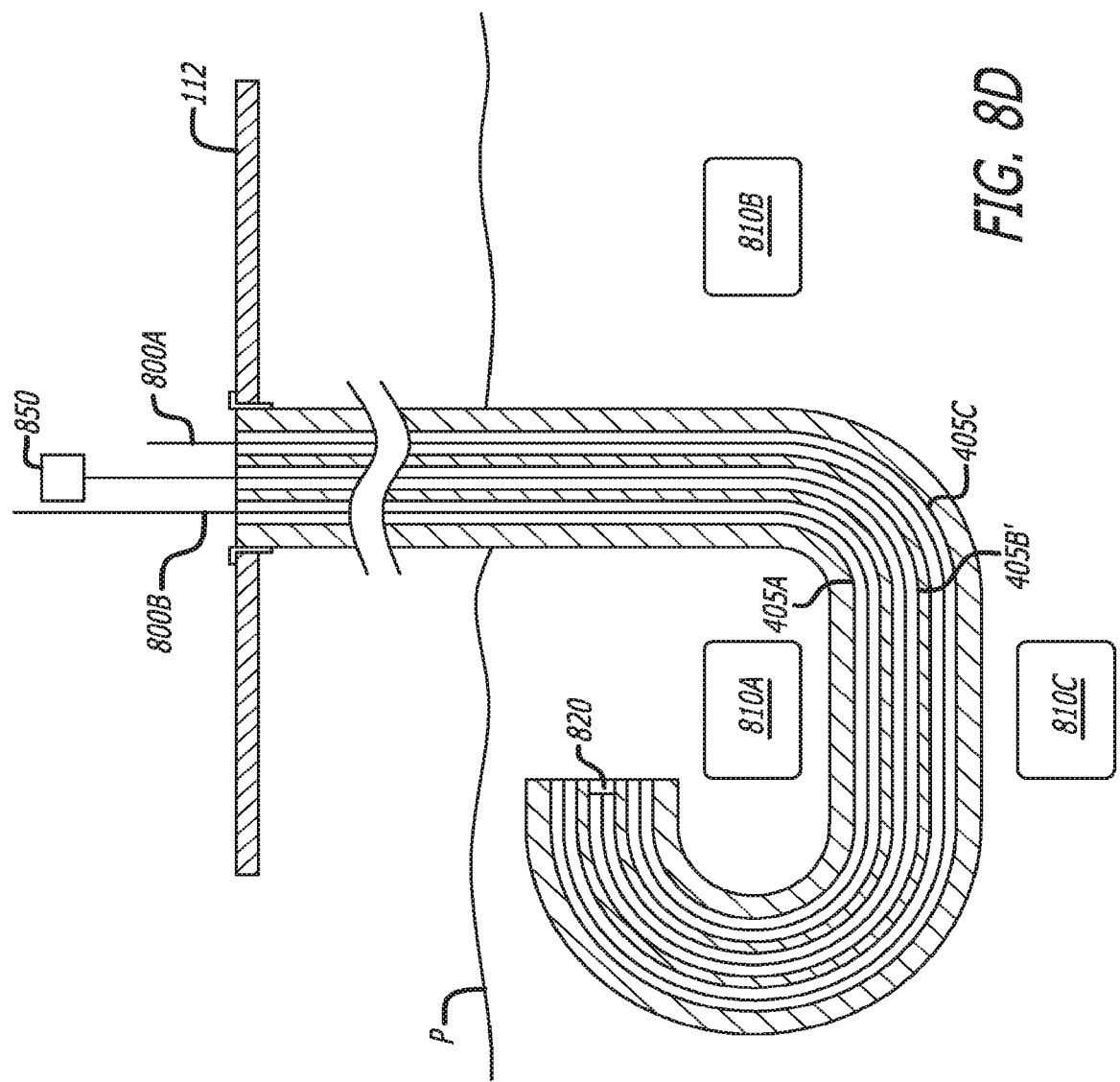

In FIG. 8D, the entry guide 108 is further inserted into the body cavity between obstructions 810A and 810C such that the distal end of the entry guide is located in the surgical site. The curved portions 801A-801B of the stiffening rods 800A-800B continue to turn the distal end of the entry guide around obstruction 810A.

In FIG. 8D, a locking device 850 is inserted into the lumen 405B' to rigidize the entry guide 108 so that the stiffening rods 800A-800B may be removed and tools inserted. Alternatively, the entry guide 108 may have an integrated locking device to rigidize itself to hold its shape and position during surgery without requiring an instrument lumen to be used for this purpose.

Figure 8E:
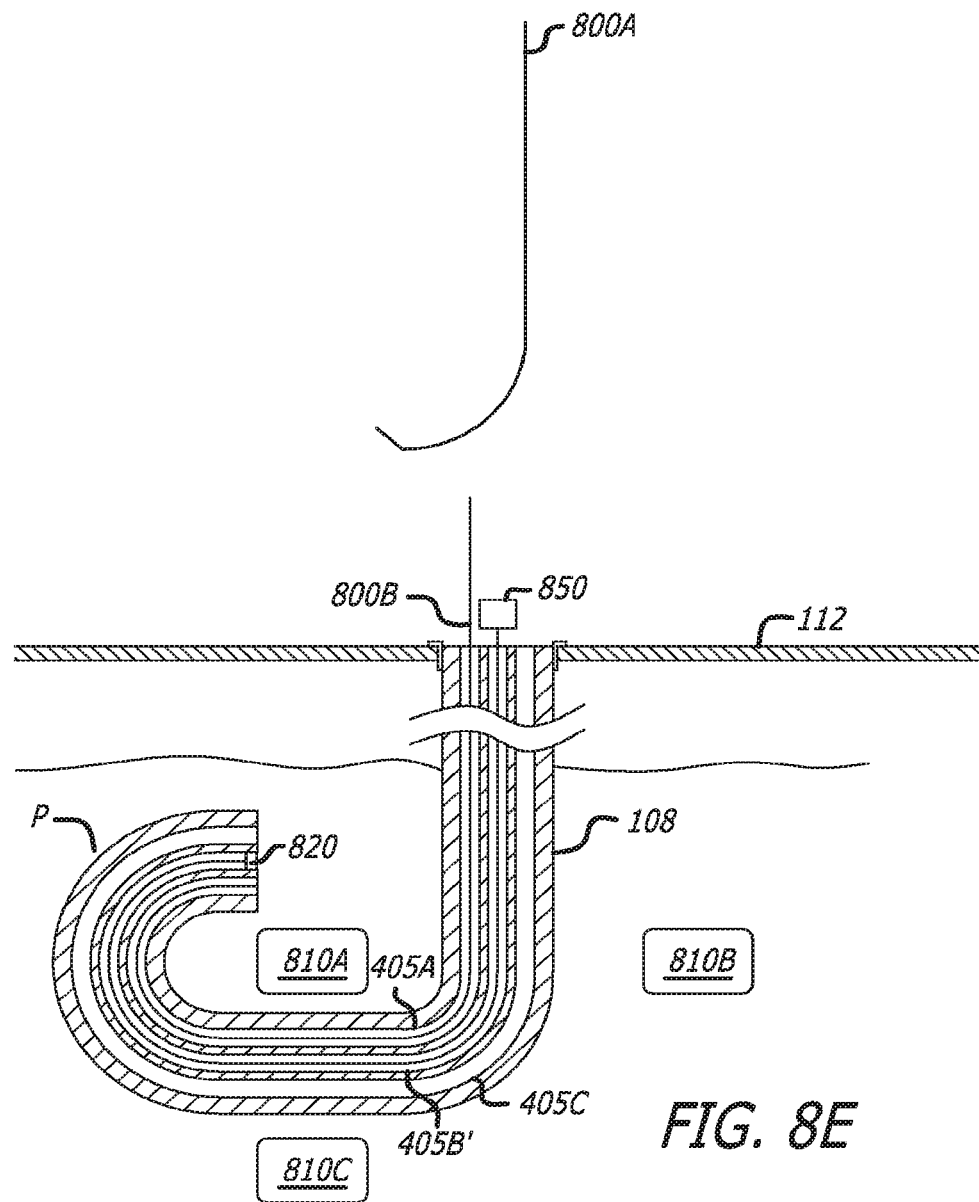

In FIG. 8E with the entry guide 108 being rigid in a locked mode from the locking device 850, the first pre-curved stiffening rod 800A may be removed from the first instrument lumen 405A. This vacates the lumen 405A so that a robotic surgical tool may be inserted.

In FIG. 8F with the entry guide 108 being rigid in a locked mode from the locking device 850, the second pre-curved stiffening rod 800B has been removed from the second instrument lumen 405C. With both instrument lumens 405A, 405C vacant, robotic surgical tools 101A, 101B may be respectively inserted into these lumens and the entry guide 108 so that a robotic surgical procedure may be performed near the distal end of the entry guide 108.

Upon completion of the surgical procedure, the robotic surgical tools 101A, 101B are removed from the lumens of the entry guide 108. The locking device 850 is unlocked so as to make the entry guide flexible and may be removed from the lumen 405B'. The entry guide 108 may then be pulled at the proximal end by the platform 112 so as to remove it from the patient's body.

Entry Guide with Integrated Instrument Head

As described herein, a lumen may be closed at one end, such as lumen 405B' described with reference to FIGS. 8A-8E. In this case, a fixed instrument may be included in the distal end of the entry guide 108 in alignment with longitudinal axis of the lumen. For example, the fixed instrument may be a camera at the distal end of the entry guide, such as the camera 820 described with reference to FIGS. 8A-8E. This leaves the proximal portion of the lumen behind the head substantially empty and available to use with an actuating means.

Referring to FIG. 10, a cross section of a distal end 402 of the entry guide 108 is illustrated. The distal end 402 of entry guide includes a camera 1002 mounted in the closed lumen 405B' with the closed end 1005. The camera 1002 is substantially aligned with the cross section of the closed lumen 405B'.

The camera 1002 may be hermetically sealed to avoid body fluids from seeping therein so that it can be readily sterilized and reused. One or more electrical cables 1066A-1066B may couple to the camera 1002 so that power can be coupled to an image sensor 1051 and digital data of the captured images may be transferred from the image sensor to the video displays of the surgical system. One of the one or more electronic interface connectors (not shown) at the proximal end of the entry guide 108 may couple to the electrical cables 1066A-1066B.

The camera 1002 includes an image sensor 1051 (e.g., charge coupled device array), one or more lenses 1052A-1052B, and a transparent cover 1061 aligned together along an optical axis 1060 by a housing 1062. The image sensor 1051 captures images from light passing through the transparent cover. The one or more lenses 1052A-1052B may collimate the light parallel to the optical axis and then focus it into the image sensor 1051. The transparent cover 1061 may be hermetically sealed to the camera housing 1062 and/or the distal end of the entry guide 108. The camera 1002 may further include a filter 1054 aligned to the optical axis 1060 by the housing 1062 before the light rays reach the image sensor 1051. The camera may be adapted to provide stereo vision by providing multiple imaging sensors, lens arrays, etc, or by other known stereo imaging means.

The camera 1002 or other instrument at the end of the lumen 405B' allows another device (e.g., stiffening, locking, or steering device) to be inserted into the lumen 405B' behind the camera up to the closed end 1005 to shape and influence the behavior of the entry guide and thus mitigates the loss of instrument function that might result by dedicating the full length of the lumen to the camera function.

While a camera 1002 has been shown and described, other tools may be integrated into the distal end 402 of the entry guide 108 substantially aligned with the cross section of the closed lumen 405B' to provide another tool to efficiently use an entry guide system.

Locking Devices to Rigidize the Entry Guide

The stiffening rods described previously with reference to FIGS. 8A-9D may hold the shape of the flexible entry guide on their own if left inserted within the lumen. However, they may need to be removed to allow insertion of a robotic surgical tool. Moreover, flexible devices or tools inserted into the instrument lumens may require a different mechanism to lock the entry guide into a rigid state so that its position and shape to the surgical site is substantially held.

A simple means of influencing the entry guide behavior by insertion of a flexible locking device into one of the instrument lumens. The flexible locking device is initially a flexible device that is inserted into the instrument lumens. The flexible locking device is sized to fit tightly within the instrument lumen. After insertion, the flexible locking device may be rigidized so that the shape of the entry guide may be held during surgery, for example.

Aspects of locking devices are shown and described in the following U.S. patents which are all incorporated herein by reference: U.S. Pat. No. 3,096,962, entitled LOCKING DEVICE FOR A MEASURING APPARATUS OR THE LIKE, issued to P. J. Meijs on Jul. 9, 1963; U.S. Pat. No. 3,546,961, entitled VARIABLE FLEXIBILITY TETHER, issued to T. Marton on Dec. 15, 1970; U.S. Pat. No. 4,949,927, entitled ARTICULABLE COLUMN issued to Madocks et al. on Aug. 21, 1990; U.S. Pat. No. 5,251,611, entitled METHOD AND APPARATUS FOR CONDUCTING EXPLORATORY PROCEDURES, issued to Zehel et al. on Oct. 12, 1993; U.S. Pat. No. 5,759,151, entitled FLEXIBLE STEERABLE DEVICE FOR CONDUCTING EXPLORATORY PROCEDURES, issued to Robert H. Sturges on Jun. 2, 1998; and U.S. Pat. No. 5,899,425, entitled ADJUSTABLE SUPPORTING BRACKET HAVING PLURAL BALL AND SOCKET JOINTS, issued to Corey Jr. et al. on May 4, 1999.

Generally, when cylinders and spheres of a flexible locking tool, are loosely constrained by the locking cables such that the frictional forces between them are small. In this case the respective flexible lockable shaft flexes easily. When a cable or rod is tensioned at an actuating base the end cylinder is pulled with a force towards a first cylinder such that the cylinders and spheres are compressed together thereby increasing the friction between the contacting surfaces and effectively locking the shaft into a rigid shape.

Upon releasing the tension in the locking cables, mating surfaces may naturally separate if a sufficient force is present to sufficiently stretch the cable. Otherwise, springs may be added to the flexible locking tools to separate the mating surfaces to reduce the friction and allow the shafts to flex. Alternatively, an unlocking tool or stiffening rod may be inserted into an adjacent lumen to stretch the entry guide and the shaft of the locking tool.

While the shape of the entry guide may be held rigid by an instrument inserted into a lumen, a locking device may be incorporated to be an integral part of the entry guide. For example, a locking device may be inserted in a center lumen and formed as an integral part of the entry guide. Alternatively, the locking device may be incorporated as part of a flexible sleeve around the entry guide.

Referring now to FIGS. 6A-6C, a cutaway view of an entry guide system 1300 is illustrated. The entry guide system 1300 includes the flexible entry guide 108 surrounded by a flexible lockable sleeve 1301. The entry guide 108 is coaxial to the flexible lockable sleeve 1301 and is inserted and steered with the sleeve into a patient's body. A proximal end of the entry guide 108 and sleeve 1301 are coupled to the platform 112. The distal end of the sleeve 1301 extends down to be near the distal end of the entry guide 108.

The flexible lockable sleeve 1301 is formed of a plurality of lockable rings 1310. A plurality of locking cables 1320 are routed through channels 1312 in each of the locking rings 1310. A curved convex surface 1324 of each lockable ring 1310 may slide against a curved concave surface 1326 in a neighboring lockable ring.

A plurality of actuators 1350A-1350C may be coupled to the locking cables 1320 to robotically control the entry guide system 1300 and the flexible lockable sleeve 1301. Upon substantial equal tensioning in the cables 1320, the flexible lockable sleeve 1301 may be locked into a rigid position so that the coaxial entry guide 108 is constrained in its shape in a rigid position. In this locked position, robotic surgical tools 101 may be inserted into the plurality of lumens 405 in the entry guide to perform a robotic surgery near the distal end of the entry guide system 1300.

Releasing the Entry Guide Shape

Upon completion of the minimally invasive surgical procedure, the robotic surgical instruments and the entry guide may be removed. However if the tools and/or the entry guide are locked in shape, they should be released from their rigid shapes (rigid mode) to become a flexible shape (flexible mode) prior to the withdrawal of the entry guide.

For those devices with a cable locking mechanism, the cable tension is initially released so that the rigid shaped form of the tool/entry guide may become released. The release of the cable and the force on the platform to remove the entry guide may be sufficient to release the entry guide from its rigid shape. However, various devices may be used to assist in releasing the friction between joints in a flexible tool/entry guide.

For example, the tool/entry guide may have springs between joints or vertebrae which may expand and release the friction. A non-compressible shaft may be inserted into a closed base lumen of the entry guide. The non-compressible shaft presses outward on the last joint of flexible shaft while the platform pulls outward on the entry guide to assist in releasing the friction between joints.

Transluminal Surgery

Transluminal surgery with a flexible entry guide system may use a combination of the apparatus and methods described herein. The entry guide may first be steered through intermediate tissue or through a natural body lumen (e.g., down esophagus to stomach). The entry guide may generally be steered with one or more instruments having a flexible steerable shaft, such as tools 502A-502B described with reference to FIGS. 5A-5C. Alternatively, the entry guide may be steered with one or more instruments with shafts having a portion locked to the entry guide within the lumens, such as tools 502A-502B described with reference to FIGS. 5F-5H. The instruments within the lumens may be extended out beyond the entry guide to operate on a patient lumen (e.g., stomach) to create an opening in which to install a port management device to a wall (e.g., stomach wall). The port management device may be an entry guide overtube that allows for management of insufflation of the stomach or other body cavity. The entry guide may be inserted through the port management device and steered towards a surgical site.

Upon reaching the surgical site, the entry guide may be rigidized. The entry guide may be rigidized by its own locking tool or an insertable locking tool. The instruments within the entry guide may be extended outward from the entry guide and spread to operate on tissue at the surgical site. With the entry guide inserted to the surgical site, its position may be adjusted by various steering devices, including an instrument with a portion of its shaft coupled to a lumen wall of the entry guide. The entry guide may then be steered to the portion of the body cavity (e.g., abdomen) of interest and the instrument unlocked from the lumen wall so that it may be used to operate on the tissue.

Conclusion

The embodiments of the invention have now been described with some detail. The embodiments of the invention may shape and steer an entry guide at points where the entry guide may be only passively flexible. The embodiments of the invention may actuate an entry guide with greater force, or avoid applying greater instrument forces to reach a distant surgical cite without increasing its diameter. Conversely, the embodiments of the invention may reduce the diameter of the entry guide by reducing or eliminating its control cables without reducing the force that can be applied thereto. Less cross-section of the entry guide may be devoted to a dedicated entry guide actuation mechanism with the embodiments of the invention to minimize the diameter of the entry guide. Cross section of the entry guide devoted to delivering and actuated instruments (the instrument lumens) previously used to actuate the entry guide may be reused to steer, guide, and influence the shape of the entry guide. The embodiments of the invention may simplify the actuation of the entry guide actuation without reducing its functionality. Moreover, the embodiments of the invention allow the entry guide to assume shapes that may allow traversal of body lumens or cavities that otherwise may not have been possible with the entry guide alone, or by an endoscope alone.

While certain exemplary embodiments have been described and shown in the accompanying drawings, it is to be understood that such embodiments are merely illustrative of and not restrictive on the broad invention, and that the embodiments of the invention not be limited to the specific constructions and arrangements shown and described, since various other modifications may become apparent after reading this disclosure. For example, some embodiments of the invention have been described with reference to a single instrument or device being used in a single lumen of the entry guide. However a plurality of the locking devices and guide devices described previously may be used in multiple lumens of the entry guide. Each of the plurality may be positioned to influence the shape of a different portion of the length of the entry guide. Instead, the embodiments of the invention should be construed according to the claims that follow below.

What is claimed is:

1. A robotic medical system, comprising:
   a flexible entry guide tube comprising at least one rigidizing cable being actuatable to rigidize a shape of the flexible entry guide tube in place within a body cavity, the at least one rigidizing cable being further actuatable to steer the flexible entry guide tube as the flexible entry guide tube is guided toward a medical site;
   a flexible tool insertable into an instrument lumen of the flexible entry guide tube, the flexible tool configured to perform a medical procedure while the shape of the flexible entry guide tube is rigidized by the at least one rigidizing cable;
   one or more processors; and
   a memory comprising machine readable instructions that cause the one or more processors to:
      receive, via a user input device, a command to drive the flexible tool or the flexible entry guide tube; and
      control co-articulation of the flexible entry guide tube and the flexible tool while the robotic medical system is in a first drive mode, wherein the co-articulation in the first drive mode includes steering of a distal portion of the flexible entry guide tube to cause an articulation in the distal portion of the flexible entry guide tube, wherein the steering of the distal portion of the flexible entry guide tube causes steering of a steerable portion of the flexible tool such that the steerable portion of the flexible tool has an articulation that corresponds with the articulation of the distal portion of the flexible entry guide tube.

2. The robotic medical system of claim 1, wherein the machine readable instructions further cause the one or more processors to control movement of the flexible tool to extend a distal end of the flexible tool beyond a distal end of the flexible entry guide tube while the robotic medical system is in a second drive mode.

3. The robotic medical system of claim 1, wherein the machine readable instructions further cause the one or more processors to, while the robotic medical system is in a second drive mode, control steering of the flexible entry guide tube while the flexible tool remains passive.

4. The robotic medical system of claim 3, wherein the machine readable instructions further cause the one or more processors to control movement of the flexible entry guide tube to extend a distal end of the flexible entry guide tube beyond a distal end of the flexible tool while the robotic medical system is in the second drive mode.

5. The robotic medical system of claim 3, wherein in the second drive mode, the flexible entry guide tube is configured to be advanced or retracted while the flexible tool remains stationary.

6. The robotic medical system of claim 1, wherein in the first drive mode, the flexible entry guide tube and the flexible tool are each configured to advance or retract.

7. The robotic medical system of claim 1, further comprising a manipulator configured to control movement of the flexible entry guide tube and movement of the flexible tool.

8. The robotic medical system of claim 7, wherein the machine readable instructions further cause the one or more processors to:
   receive, via the user input device, an advancement instruction to advance the flexible entry guide tube when the robotic medical system is in the first drive mode; and
   in response to receiving the advancement instruction, advance the flexible entry guide tube via the manipulator.

9. The robotic medical system of claim 7, wherein the machine readable instructions further cause the one or more processors to:
   receive, via the user input device, an advancement instruction to advance the flexible tool when the robotic medical system is in the first drive mode; and
   in response to receiving the advancement instruction, advance the flexible tool via the manipulator.

10. The robotic medical system of claim 7, wherein the machine readable instructions further cause the one or more processors to:
   receive, via the user input device, an advancement instruction to advance the flexible tool when the robotic medical system is in a second drive mode, wherein in the second drive mode, the machine readable instructions further cause the one or more processors to control movement of the flexible tool to extend a distal end of the flexible tool beyond a distal end of the flexible entry guide tube; and
   in response to receiving the advancement instruction, advance the flexible tool via the manipulator.

11. The robotic medical system of claim 1, wherein the flexible tool comprises an imaging device, the imaging device configured to capture image data as the flexible entry guide tube is guided toward the medical site.

12. The robotic medical system of claim 1, wherein flexible tool comprises:
   the steerable portion; and
   a steering cable extending within the flexible tool to enable independent steering of the steerable portion.

13. The robotic medical system of claim 7, wherein the manipulator is coupled to the flexible entry guide tube.

14. The robotic medical system of claim 1, wherein the co-articulation in the first drive mode further includes steering of the steerable portion of the flexible tool to cause an articulation in the steerable portion of the flexible tool, wherein the steering of the steerable portion of the flexible tool causes steering of the distal portion of the flexible entry guide tube such that the distal portion of the flexible entry guide tube has an articulation that corresponds with the articulation of the steerable portion of the flexible tool.

* * * * *

UNITED STATES PATENT AND TRADEMARK OFFICE
CERTIFICATE OF CORRECTION

| | |
|---|---|
| PATENT NO. | : 12,042,120 B2 |
| APPLICATION NO. | : 17/190936 |
| DATED | : July 23, 2024 |
| INVENTOR(S) | : Theodore W. Rogers and David Q. Larkin |

It is certified that error appears in the above-identified patent and that said Letters Patent is hereby corrected as shown below:

In the Specification

Column 1, under "Cross-Reference to Related Applications" should read as follows:
-- This non-provisional United States (U.S.) patent application is a continuation of U.S. Patent Application No. 15/660,673, filed July 26, 2017, which is a divisional application of and claims the benefit of U.S. patent application Ser. No. 12/165,633, entitled "METHODS AND APPARATUS TO SHAPE FLEXIBLE ENTRY GUIDES FOR MINIMALLY INVASIVE SURGERY," filed on June 30, 2008, now U.S. Patent No. 9,962,066, which in turn claims the benefit of and is a continuation-in-part of U.S. patent application Ser. No. 11/762,165, entitled "MINIMALLY INVASIVE SURGICAL SYSTEM," filed on June 13, 2007, now U.S. Patent No, 9,060,678, and also claims the benefit of and is a continuation-in-part of U.S. patent application Ser. No. 11/491,384, entitled "ROBOTIC SURGERY SYSTEM INCLUDING POSITION SENSORS USING FIBER BRAGG GRATINGS," filed on July 20, 2006, now U.S. Patent No. 7,930,065, all of which are incorporated herein by reference in their entirety. U.S. Patent Application No. 11/762,165 further claims priority to and the benefit of U.S. Provisional Patent Application Nos. 60/813,075, 60/813,207, 60/813,198, 60/813,173, 60/813,125, 60/813,030, and 60/813,029, all filed on June 13, 2006, of which this patent application also claims the benefit, and all of which are incorporated herein by reference in their entirety. U.S. Patent Application No. 11/491,384 further claims the benefit of U.S. Provisional Patent Application No. 60/755,157, filed on December 30, 2005, of which this application also claims the benefit, and which is incorporated herein by reference in its entirety. --

Signed and Sealed this
Twenty-second Day of October, 2024

Katherine Kelly Vidal
*Director of the United States Patent and Trademark Office*